(12) United States Patent
Power et al.

(10) Patent No.: US 10,201,558 B2
(45) Date of Patent: *Feb. 12, 2019

(54) COMPOSITIONS OF SELENOORGANIC COMPOUNDS AND METHODS OF USE THEREOF

(71) Applicant: Alltech, Inc., Nicholasville, KY (US)

(72) Inventors: Ronan Power, Lexington, KY (US); Zi-Jian Lan, Lexington, KY (US)

(73) Assignee: Alltech, Inc., Nicholasville, KY (US)

( * ) Notice: Subject to any disclaimer, the term of this patent is extended or adjusted under 35 U.S.C. 154(b) by 253 days.

This patent is subject to a terminal disclaimer.

(21) Appl. No.: 14/855,065

(22) Filed: Sep. 15, 2015

(65) Prior Publication Data
US 2016/0082033 A1 Mar. 24, 2016

Related U.S. Application Data

(63) Continuation-in-part of application No. PCT/US2014/029542, filed on Mar. 14, 2014.

(51) Int. Cl.
| | |
|---|---|
| A61K 31/28 | (2006.01) |
| A61K 38/05 | (2006.01) |
| A61K 38/28 | (2006.01) |
| C07D 473/34 | (2006.01) |
| A61K 31/7076 | (2006.01) |
| A61K 31/7135 | (2006.01) |
| A61K 31/706 | (2006.01) |
| A61K 31/7064 | (2006.01) |

(52) U.S. Cl.
CPC .......... *A61K 31/7135* (2013.01); *A61K 31/28* (2013.01); *A61K 31/7076* (2013.01); *A61K 38/05* (2013.01); *A61K 38/28* (2013.01); *C07D 473/34* (2013.01); *A61K 31/706* (2013.01); *A61K 31/7064* (2013.01)

(58) Field of Classification Search
CPC .............. C07D 473/34; A61K 31/7076; A61K 31/7135; A61K 31/28; A61K 38/05; A61K 38/28
See application file for complete search history.

(56) References Cited

U.S. PATENT DOCUMENTS

| | | | |
|---|---|---|---|
| 8,796,241 B2* | 8/2014 | Lubin | A61K 31/7076 435/375 |
| 8,865,763 B2 | 10/2014 | Lyons et al. | |
| 9,642,874 B2* | 5/2017 | Power | A61K 31/7076 |
| 9,833,486 B2* | 12/2017 | Power | A61K 36/06 |
| 2006/0093684 A1 | 5/2006 | Takeda et al. | |
| 2006/0198906 A1 | 9/2006 | Majeed et al. | |
| 2007/0077238 A1 | 4/2007 | Teo et al. | |
| 2007/0122491 A1 | 5/2007 | Lyons et al. | |
| 2008/0107755 A1 | 5/2008 | Lyons et al. | |
| 2012/0094947 A1 | 4/2012 | Lubin et al. | |
| 2015/0057243 A1 | 2/2015 | Zhou et al. | |
| 2016/0045533 A1 | 2/2016 | Power et al. | |
| 2016/0082033 A1 | 3/2016 | Power et al. | |
| 2016/0090397 A1 | 3/2016 | Zhou et al. | |
| 2016/0113977 A1* | 4/2016 | Power | A61K 31/198 424/93.51 |
| 2016/0361338 A1* | 12/2016 | Power | A61K 31/7076 |

FOREIGN PATENT DOCUMENTS

| | | |
|---|---|---|
| WO | 2013151975 A1 | 10/2013 |
| WO | 2014144776 A1 | 9/2014 |
| WO | 2015137983 A1 | 9/2015 |

OTHER PUBLICATIONS

International Search Report and the Written Opinion for International Patent Application PCT/US15/50490 dated Jan. 27, 2016.
Preud'homme, H., et al., "Large Scale identification of selenium metabolites by online size-exclusion-reversed phase liquid chromatography with combined inductively coupled plasma (ICP-MS) and electrospray ionization linear trap-Orbitrap mass spectrometry (ESI-MS(n))", Metallomics, May 2012, vol. 4 (5), pp. 422-432.
Pieczenik, S. R., et al., "Mitochondrial dysfunction and molecular pathways of disease", Experimental and Molecular Pathology, 2007, vol. 83, pp. 84-92.
Pinto, A., et al., "Supranutritional selecnium induces alterations in molecular targets related to energy metabolism in skeletal muscle and visceral adipose tissue of pigs", Journal of Inorganic Biochemistry, 2012, vol. 114, pp. 47-54.
Amaudguilhem, C., et al., "Selenium metabolomics in yeast using complementary reversed-phase/hydrophilic ion interaction (HILIC) liquid chromatography-electrospray hybrid quadrupole trap/Orbitrap mass spectrometry", Anal. Chim. Acta., Dec. 13, 2012 (757), pp. 26-38.
Ouerdane, L., et al., "Comprehensive speciation of low-molecular weight selenium metabolites in mustard seeds using HPLC-electrospray linear trap/Orbitrap tandem mass spectrometry", Metallomics, Sep. 2013, 5 (9), pp. 1294-1304.
Bierla, K, et al., "Comprehensive speciation of selenium in selenium-rich yeast", Trends in Analytical Chemistry, Dec. 2012, vol. 41, pp. 122-132.
Duclos, R. I., et al., "Synthesis and characterization of Se-adenosyl-L-selenohomocysteine selenoxide", J Sulphur Chem., Apr. 2015, 36(2), pp. 135-144.
Kogami, M., et al., "An efficient method for the synthesis of selenium modified nucleosides: its application in the synthesis of Se-adenosyl-L-selenomethionine (SeAM)", Organic & Biomolecular Chemistry, Aug. 2015, 13(36), pp. 9405-9417.
Bothwell, I. R., et al., "Large-Scale, Protection-Free Synthesis of Se-Adenosyl-L-selenomethionine Analogues and Their Application as Cofactor Surrogates of Methyltransferases", Org. Lett., May 2014, 16(11), pp. 3056-3059.

(Continued)

*Primary Examiner* — Lawrence E Crane
(74) *Attorney, Agent, or Firm* — Choate, Hall & Stewart LLP; Brenda Herschbach Jarrell

(57) ABSTRACT

The present application relates to compositions comprising selenium compounds, such as 5'-Methylselenoadenosine, a compound of Formula (I), and combinations thereof, and methods of using the same for inhibiting β amyloid aggregation, ApoE4 expression, p38 or Tau protein phosphorylation, or increasing Neprilysin and Insulin Degrading Enzyme expression.

8 Claims, 23 Drawing Sheets
(6 of 23 Drawing Sheet(s) Filed in Color)

(56) References Cited

OTHER PUBLICATIONS

Singh, S., et al., "Facile Chemoenzymatic Strategies for the Synthesis and Utilization of S-Adenosyl-(L)-Methionine Analogues", Angew. Chem. Int. Ed., Mar. 2014, 53 (15), pp. 3965-3969.
SciFinder, "Kogami_2015_Org_Bio_Chem_Structures", ACS, 2015, structure 31, 1805788-83-3, 8 pages.
International Search Report for International Patent Application PCT/US2014/US2014/029542 dated Jul. 31, 2014, 3 pages.
U.S. Appl. No. 14/855,128, filed Sep. 15, 2015, Ronan Power et al.
U.S. Appl. No. 15/121,412, filed Aug. 25, 2016, Ronan Power et al.
International Search Report and the Written Opinion for International Patent Application PCT/US2015/050476 dated Dec. 17, 2015.
Brennan, K. M. et al., Effects of organic and inorganic dietary selenium supplementation one gene expression profiles in oviduct tissue from broiler-breeder hens, Animal Reproduction Science, 125(180-188 (2011).
Can, B. et al., Selenium Treatment Protects Diabetes-Induced Biochemical and Ultrastructural Alterations in Liver Tissue, Biological Trace Element Research, 105:135-150 (2005).
Lowell, B. and Shulman, G., Mitochondrial Dysfunction and Type 2 Diabetes, Science, 307:384-387 (2005).

\* cited by examiner

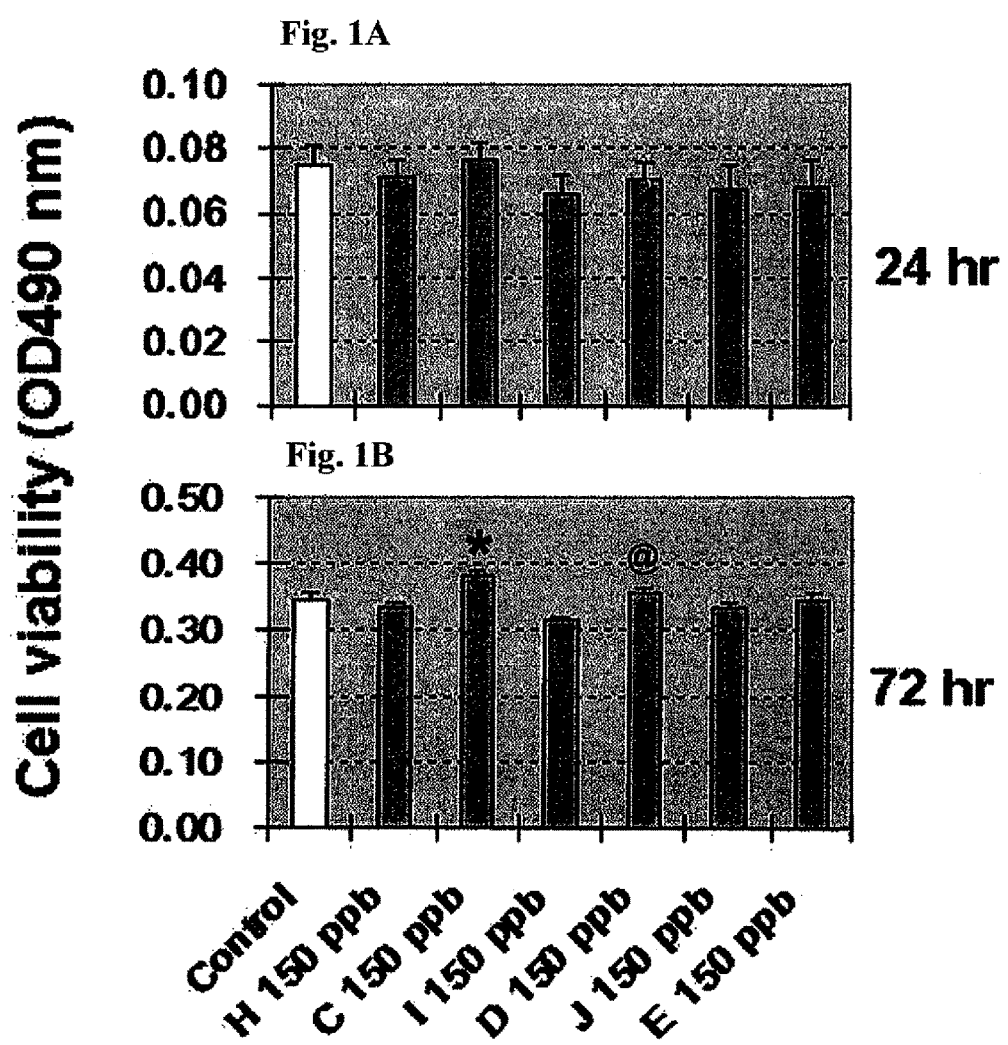

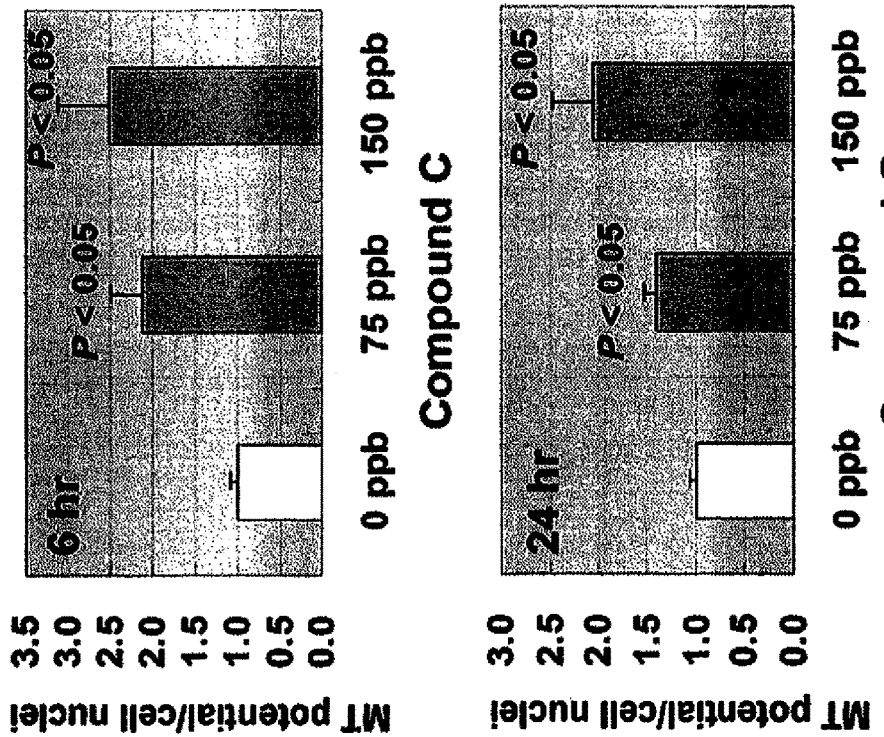
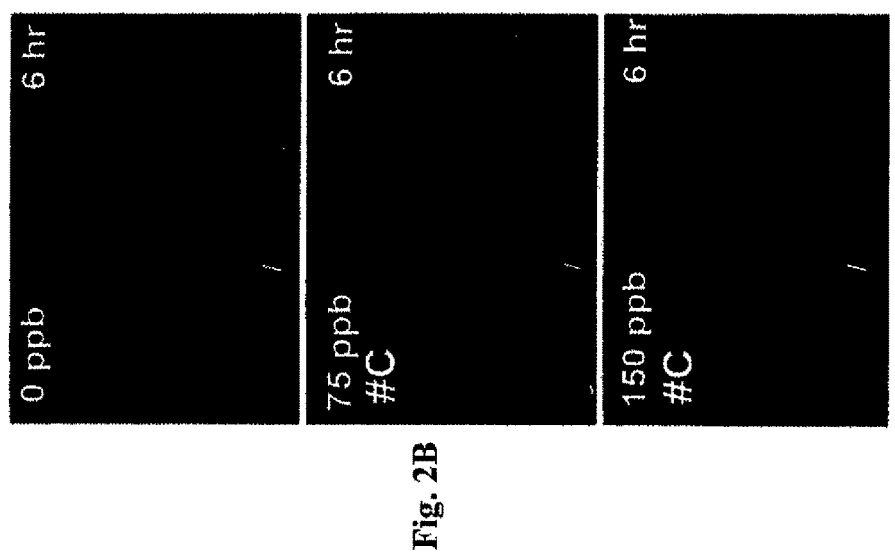
Fig. 2A  Fig. 2B  Fig. 2C  Fig. 2D  Fig. 2E

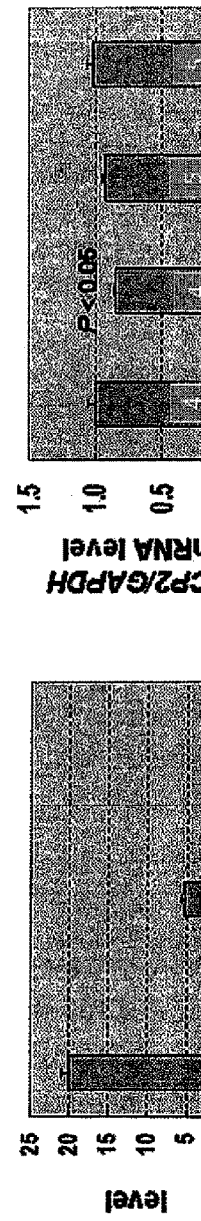
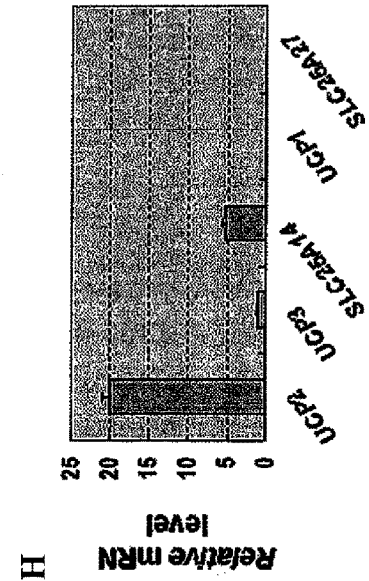
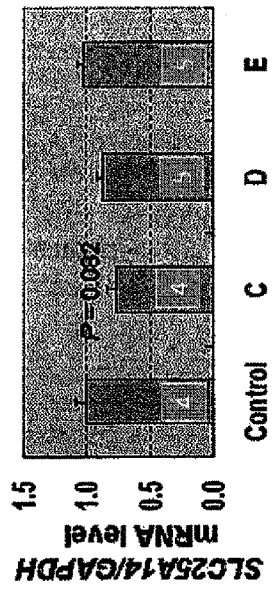
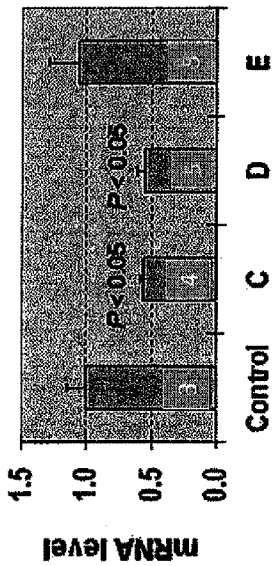

Fig. 5A
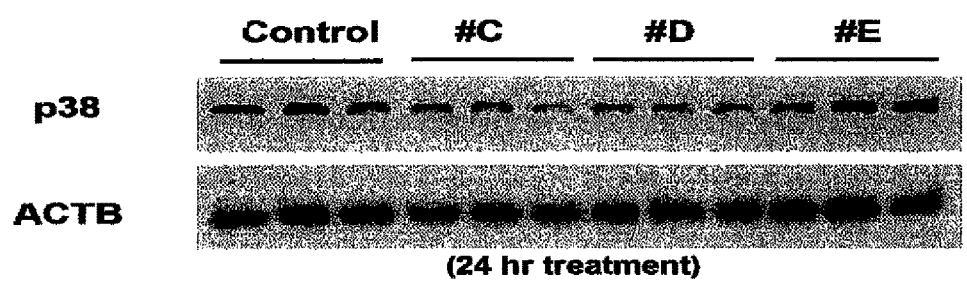
(24 hr treatment)
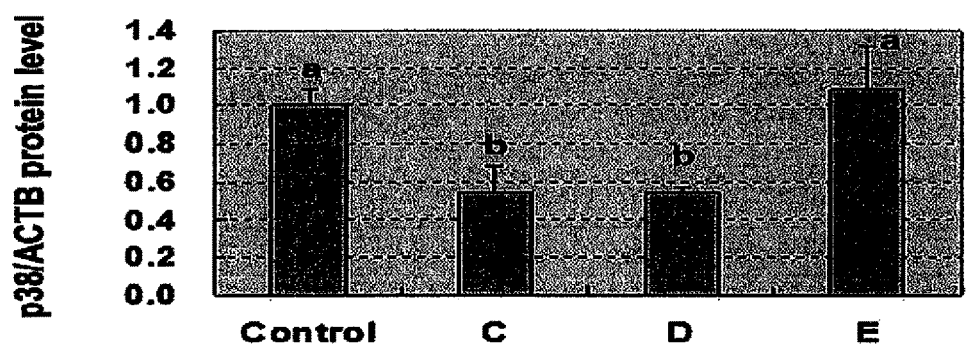
Fig. 5B (24 hr treatment)

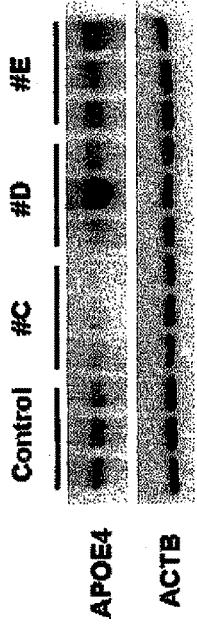
Fig. 7A
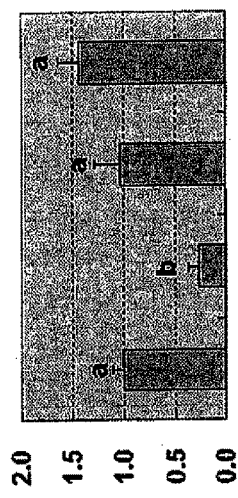
Fig. 7B
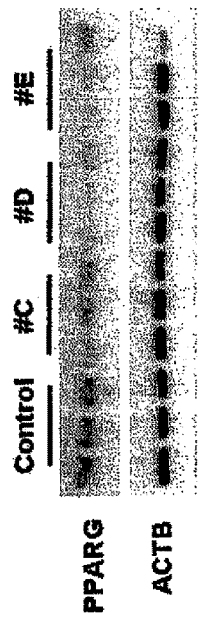
Fig. 7C (6 hr treatment)
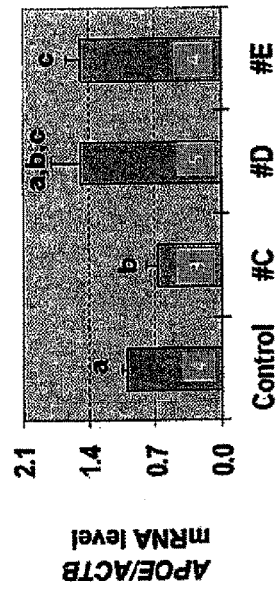
Fig. 7D
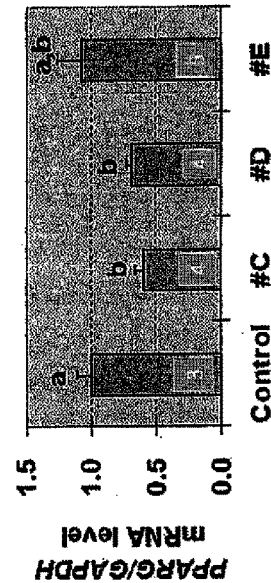
Fig. 7E
Fig. 7F (24 hr treatment)

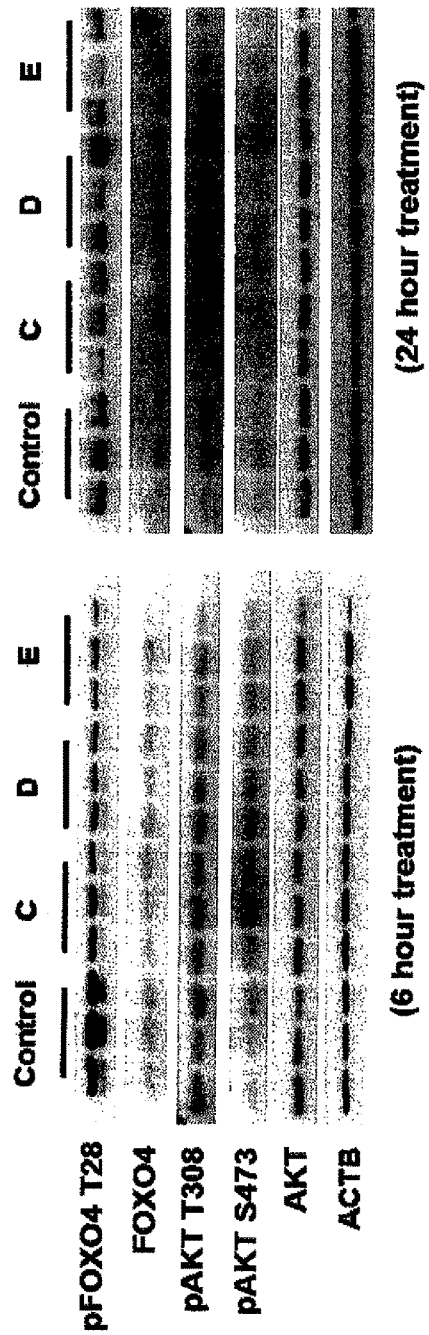
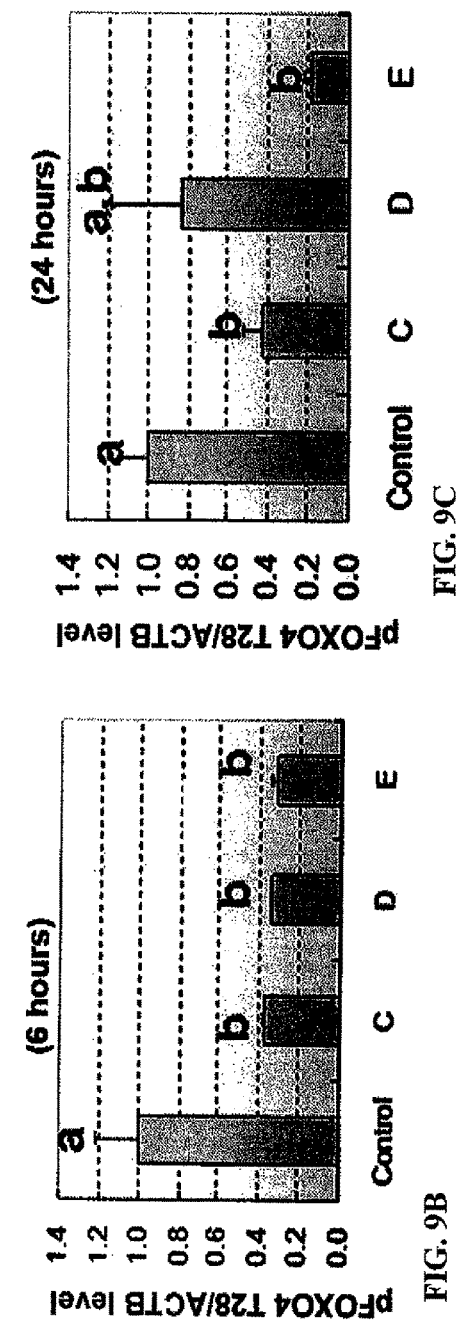
FIG. 9A
FIG. 9B
FIG. 9C

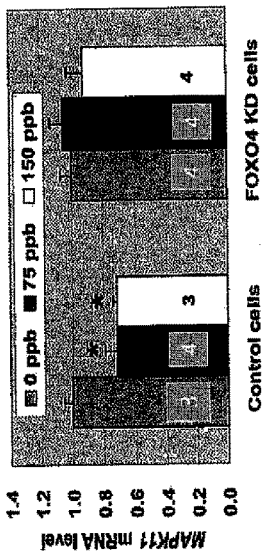
FIG. 13B
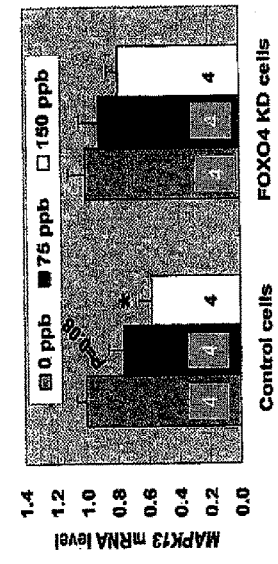
FIG. 13D
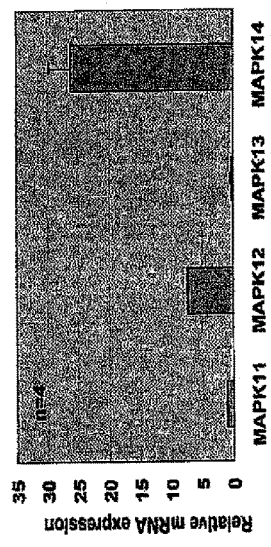
FIG. 13A
FIG. 13C
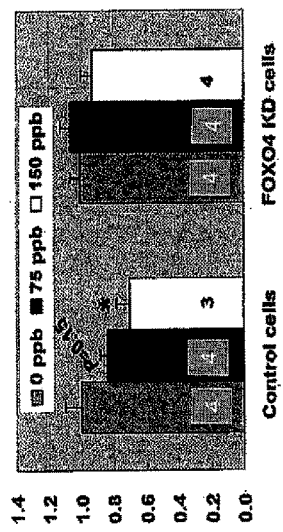
FIG. 13E

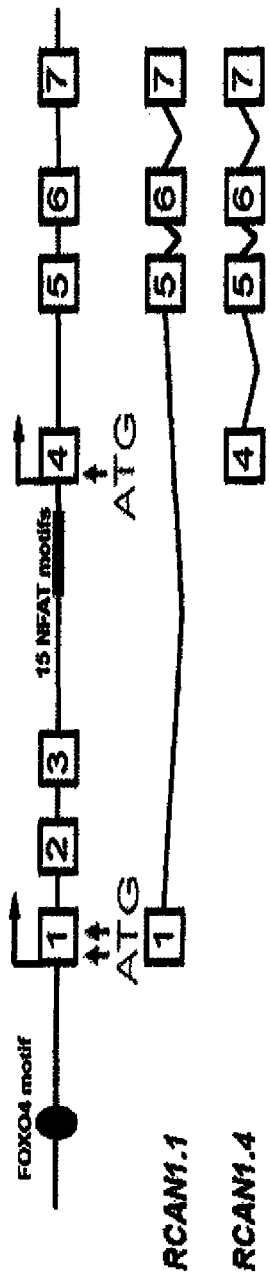
FIG. 14A
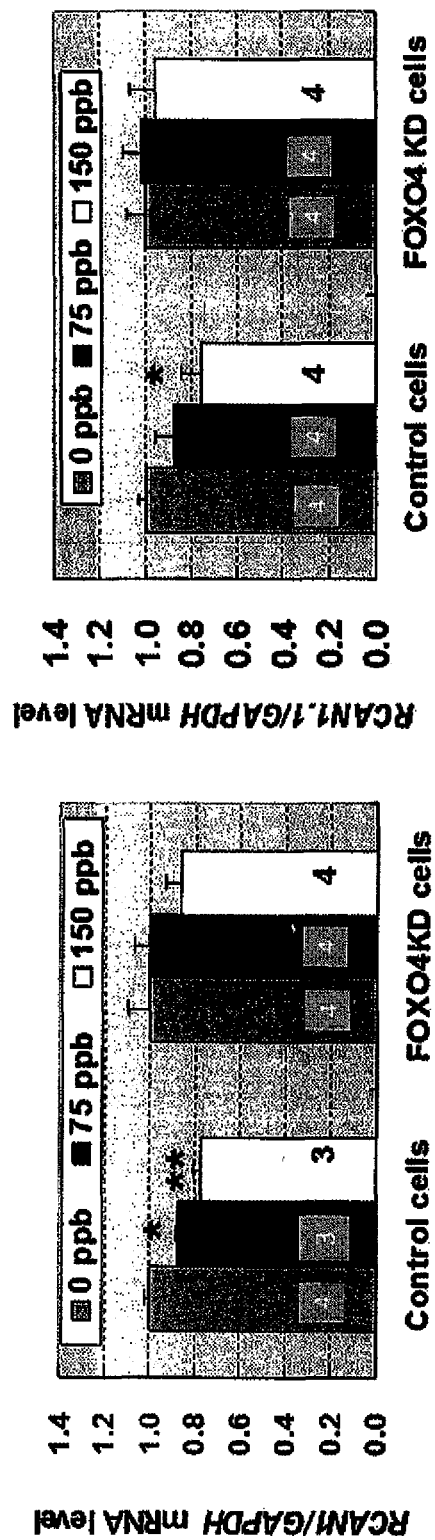
FIG. 14B
FIG. 14C

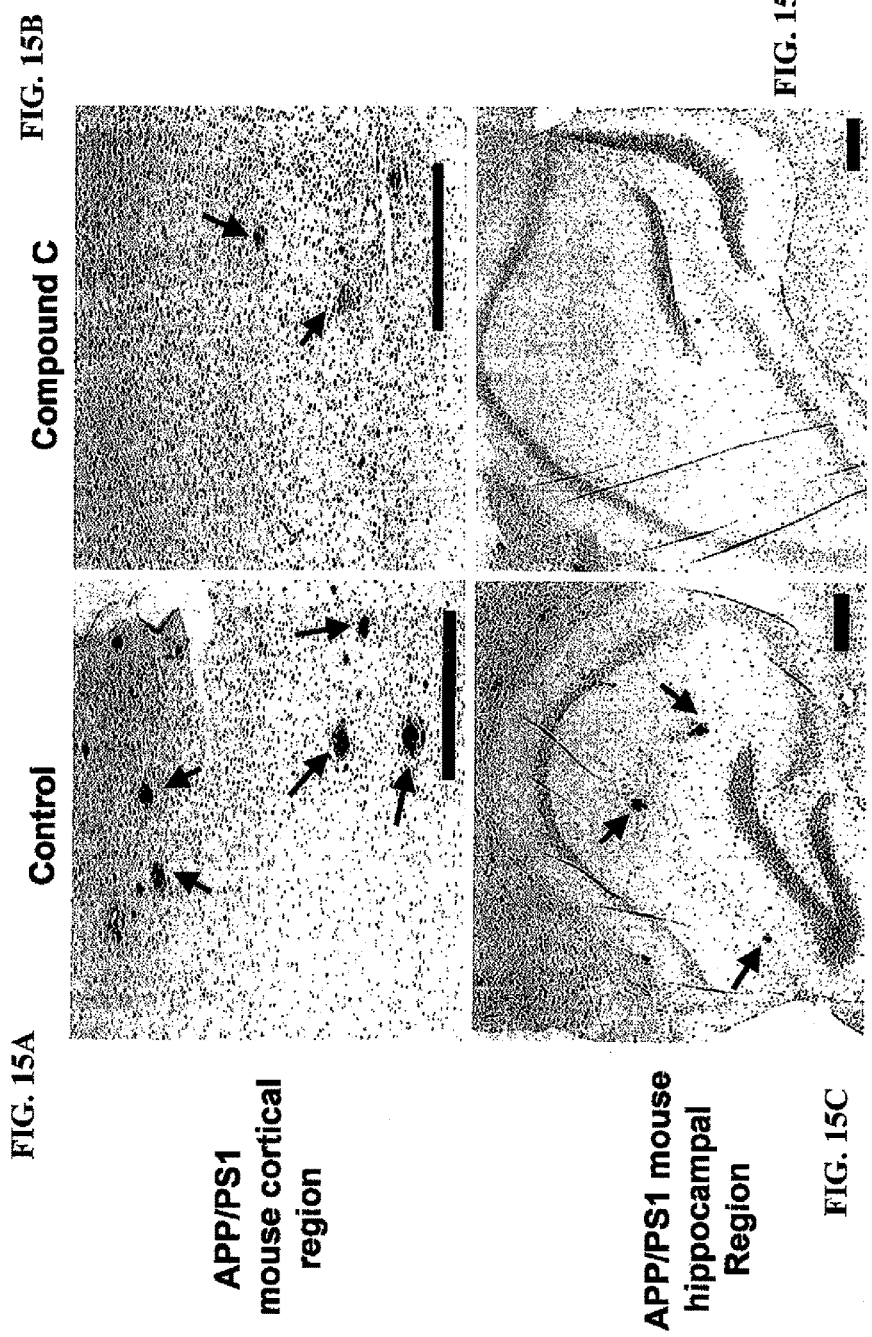

Fig. 17A
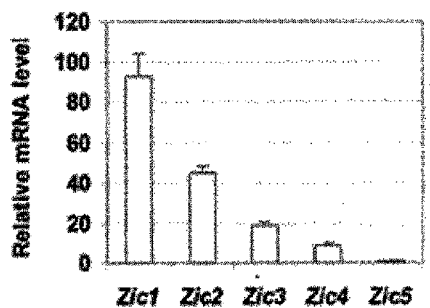
Fig. 17B
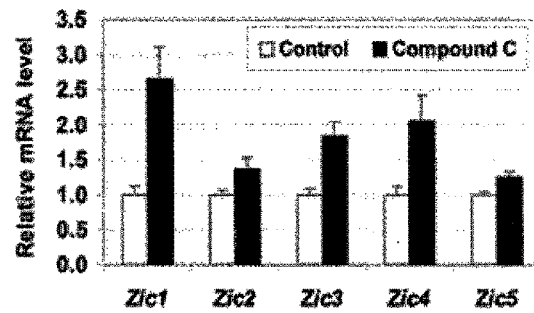
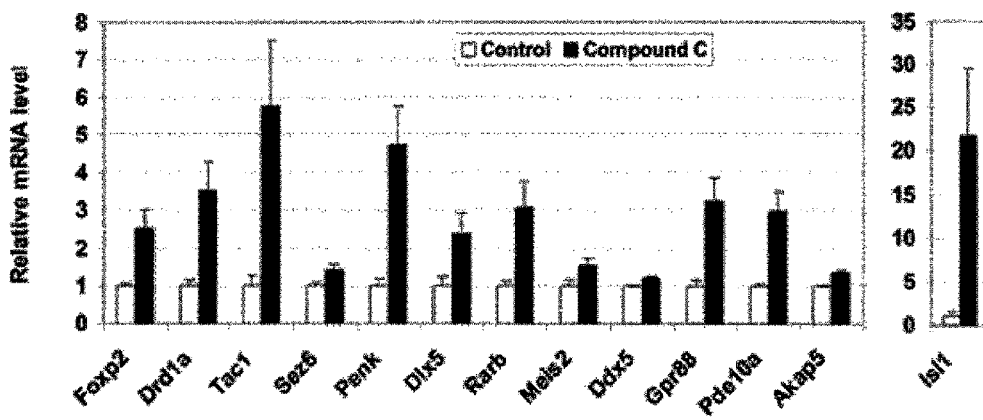
Fig. 17C

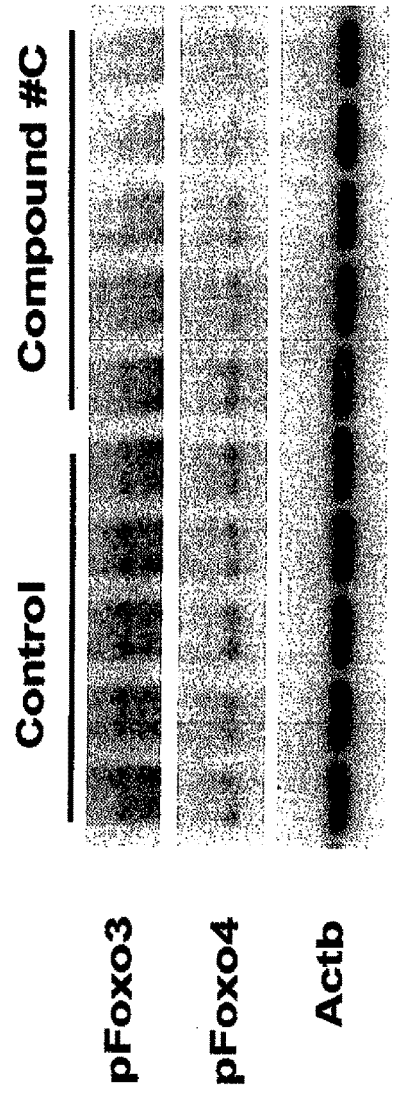
FIG. 18A
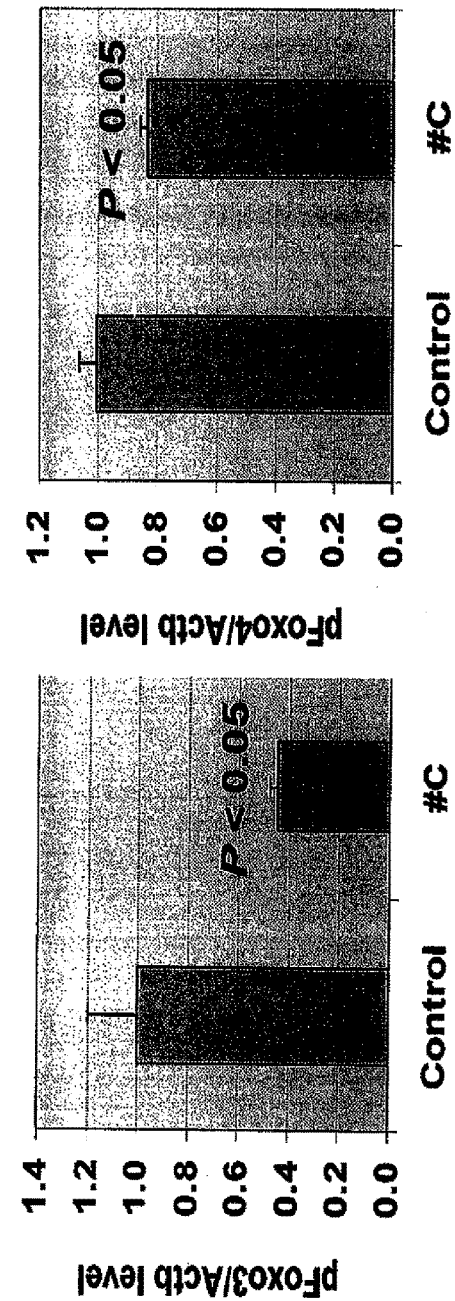
FIG. 18B
FIG. 18C

COMPOSITIONS OF SELENOORGANIC COMPOUNDS AND METHODS OF USE THEREOF

CROSS-REFERENCE TO RELATED APPLICATION

This patent application is a continuation-in-part of International Patent Application Serial No. PCT/US2014/029542, filed 14 Mar. 2014, which application is incorporated by reference herein.

FIELD OF THE PRESENT APPLICATION

The present application relates to compositions of selenoorganic compounds and methods for their use to inhibit β amyloid aggregation, ApoE4 expression, p38 or Tau protein phosphorylation, or to increase Neprilysin and Insulin Degrading Enzyme expression.

BACKGROUND

Selenium (Se) is an essential trace element that plays a critical role in many biological processes, such as reproduction, thyroid hormone metabolism, DNA synthesis, and protection from oxidative damage and infection. Selenium is incorporated at the catalytic site of various selenium dependent enzymes such as glutathione peroxidase (GPx), thioredoxin reductases, and one methionine-sulfoxidereductase. These selenoenzymes contribute to regulation of metabolic activity, immune function, antioxidant defense, intracellular redox regulation, and mitochondrial function.

Results in the literature indicate that different chemical forms of selenium have different bioactivities. For example, a selenozolidine was more effective at reducing the number of lung tumors than selenomethionine. (Poerschke et al, J Biochem Molecular Toxicology 2012 26:344). Barger et al. showed that mice fed different sources of selenium, for example, selenium methionine, sodium selenite and selenized yeast, had differential effects on gene expression and on specific functional pathways of mitochondrial structure and function. (Barger et al, Genes and Nutrition 2012 7:155). Selenized yeast contains many selenium and sulfur compounds but not all of the selenium compounds in selenized yeast impact biological processes. In addition, a mixture of selenium and sulfur compounds in selenized yeast have been shown to be inhibitory to each other, to negatively impact biological processes, or be toxic to cells.

Alzheimer's Disease is the sixth leading cause of death in the United States of America, and is the most common form of dementia. Currently, Alzheimer's Disease ("AD") is estimated to affect 5.1 million people in America. There are two types of AD; Early-Onset AD, which occurs before the age of 65, and Late-Onset AD, which occurs after the age of 65. Late- and Early-Onset AD are histopathologically characterized by two types of brain lesions, senile plaques and Neurofibrillary Tangles or NFTs.

The Amyloid Beta protein (Abeta or Aβ) is the main component of senile plaques, which are often referred to as Aβ plaques. The Aβ protein is 36-43 amino acids of the larger Amyloid Precursor Protein (APP). Plaques are formed when APP is aberrantly processed by two enzymes, β-secretase and γ-secretase, resulting in the formation of the Aβ peptide. Neprilysin is an amyloid-degrading enzyme that may be regulated by APP.

NFTs are composed of hyper-phosphorylated forms of the microtubule-associated protein, Tau. In particular, the p38 gene pathway is known to be involved in Tau phosphorylation associated with AD.

Literature evidence supports the idea that both Aβ plaques and NFTs are crucial partners in the pathogenesis of Alzheimer's Disease, and that they act individually and in concert to maximize cognitive impairment and neuronal loss in affected individuals. For example, mutations in Amyloid Precursor Protein (APP) are known to induce AD with 100% penetration. Familial AD (FAD)-associated mutations of APP, presenilin-I (PSEN-I) and presenilin-2 (PSEN-2), also lead to an increased level of Aβ protein generation and aggregation.

In addition, the Apolipoprotein E (APOE) gene has been associated with AD. In particular, specific alleles of the APOE gene have been associated with Late-Onset AD. For example, the presence of an APOE4 allele indicates an increased risk of developing Late-Onset AD. However, the role that the APOE4 allele plays in the AD disease process is not known.

The apparent difference in bioactivity and availability of distinct chemical forms of selenium requires identification of compounds containing selenium that positively impact biological processes. In particular, there is a need to characterize the effects of selenium on β amyloid aggregation, Tau and p38 phosphorylation, and APOE4 and Neprilysin gene expression. Further, there is a need to determine the effect of selenium compounds and their efficacy on treating and/or preventing Alzheimer's Disease.

SUMMARY OF THE INVENTION

The present disclosure provides a method of inhibiting β amyloid aggregation in a subject. The method for inhibiting β amyloid aggregation comprises administering a composition to the subject, the composition comprising at least about 0.1% (w/v) of a compound selected from the group consisting of 5'-deoxy-5'-methylselenoadenosine, a compound of Formula (I), and combinations thereof. The composition of the method may also comprise a carrier.

The present disclosure also provides a method of inhibiting ApoE4 expression in a subject. The method for inhibiting ApoE4 expression comprises administering a composition to the subject, the composition comprising at least about 0.1% (w/v) of a compound selected from the group consisting of 5'-deoxy-5'-methylselenoadenosine, a compound of Formula (I), and combinations thereof. The composition of the method may also comprise a carrier.

The present disclosure further provides a method of decreasing p38 phosphorylation in a subject. The method of decreasing p38 phosphorylation comprises administering a composition to the subject, the composition comprising at least about 0.1% (w/v) of a compound selected from the group consisting of 5'-deoxy-5'-methylselenoadenosine, a compound of Formula (I), and combinations thereof. The composition of the method may also comprise a carrier.

The present disclosure additionally provides a method of increasing Neprilysin expression in a subject. The method of increasing Neprilysin expression comprises administering a composition to the subject, the composition comprising at least about 0.1% (w/v) of a compound selected from the group consisting of 5'-deoxy-5'-methylselenoadenosine, a compound of Formula (I), and combinations thereof. The composition of the method may also comprise a carrier.

In further embodiments, a method of decreasing Beta-Secretase (BACE) expression in a subject comprises: administering a composition to the subject, the composition comprising at least 0.1% (w/v) of a compound selected from the group consisting of 5'-deoxy-5'-methylselenoadenosine, a compound of Formula (I), and combinations thereof; and a carrier.

In yet other embodiments, a method of increasing Insulin-Degrading Enzyme (IDE) expression in a subject comprises:

administering a composition to the subject, the composition comprising at least 0.1% (w/v) of a compound selected from the group consisting of 5'-deoxy-5'-methylselenoadenosine, a compound of Formula (I), and combinations thereof; and a carrier.

Embodiments of the present disclosure also include a method of decreasing the Regulator of Calcineurin 1 (RCAN1) expression in a subject comprises: administering a composition to the subject, the composition comprising at least 0.1% (w/v) of a compound selected from the group consisting of 5'-deoxy-5'-methylselenoadenosine, a compound of Formula (I), and combinations thereof; and a carrier or a method of decreasing phosphorylated Tau in a subject comprising: administering a composition to the subject, the composition comprising at least 0.1% (w/v) of a compound selected from the group consisting of 5'-deoxy-5'-methylselenoadenosine, a compound of Formula (I), and combinations thereof; and a carrier.

Methods of inhibiting β amyloid aggregation, inhibiting ApoE4 expression, decreasing p38 phosphorylation, increasing Neprilysin expression, decreasing Beta-Secretase (BACE) expression, increasing Insulin-Degrading Enzyme (IDE) expression, and decreasing the Regulator of Calcineurin 1 (RCAN1) expression, and/or decrease in phosphorylation of Tau comprise administering a composition comprising a compound, wherein the compound may be synthetic or purified. The compound may also be a compound of Formula (I). The compound of Formula (I) may be a selenoglycoside. In further embodiments, the composition comprises 5'-deoxy-5'-methylselenoadenosine. The 5'-deoxy-5'-methylselenoadenosine may be a selenoglycoside.

The composition of the methods may also exclude one or more of 5'-deoxy-5'-methylthioadenosine, S-Adenosyl-L-homocysteine, and Gamma-glutamyl-methyl-cysteine. In addition, the composition of the methods may be administered orally.

The present disclosure also provides for a method of treating Alzheimer's Disease by inhibiting β amyloid aggregation in a subject. The method of treating Alzheimer's Disease comprises administering a composition to the subject, wherein the composition comprises at least about 0.033% (w/v) to at least about 0.1% (w/v) of a compound selected from the group consisting of 5'-deoxy-5'-methylselenoadenosine, a compound of Formula (I), and combinations thereof. The composition of the method may also comprise a carrier.

Finally, the present application provides for a composition. The composition comprises at least about 0.033% to at least about 0.1% (w/v) of a compound according to Formula (I):

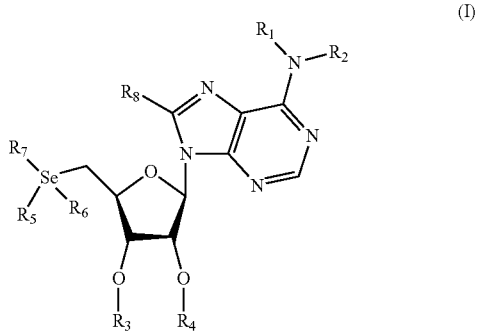

or a pharmaceutically acceptable salt, hydrate, or prodrug thereof.

$R_1$ is H, acyl, alkyl, alkenyl, alkynyl, aralkyl, carboxyl, cycloalkyl, C(O)R', of C(O)OR'. R' is alkyl, alkenyl, alkynyl, cycloalkyl, aryl, aralkyl, or heterocyclyl. $R_1$, together with $R_2$, may also form a heterocyclic ring having 4 to 8 ring members with at least one heteroatom selected from oxygen or nitrogen.

$R_2$ is H, acyl, alkyl, alkenyl, alkynyl, aralkyl, carboxyl, cycloalkyl, C(O)R', or C(O)OR'. R' is selected from alkyl, cycloalkyl, aryl, aralkyl, or heterocyclyl. $R_1$, together with $R_2$, may also form a heterocyclic ring having 4 to 8 ring members with at least one heteroatom selected from oxygen or nitrogen.

$R_3$ is H, acyl, alkyl, alkenyl, alkynyl, aralkyl, cycloalkyl, carboxyl, or C-amido. $R_3$, together with $R_4$ and the atoms to which they are attached, may also form a heterocyclic ring having 4 to 8 ring members with at least one heteroatom selected from oxygen or nitrogen.

$R_4$ is H, acyl, alkyl, alkenyl, alkynyl, aralkyl, cycloalkyl, carboxyl, or C-amido. $R_3$, together with $R_4$ and the atoms to which they are attached, may also form a heterocyclic ring having 4 to 8 ring members with at least one heteroatom selected from oxygen or nitrogen.

$R_5$ is oxo, hydroxyl, alkyl, alkenyl, alkynyl, OR', or is absent. R' is selected from alkyl, alkenyl, alkynyl, cycloalkyl, aryl, or aralkyl.

$R_6$ is oxo, hydroxyl, alkyl, alkenyl, alkynyl, OR', or is absent. R' is selected from alkyl, alkenyl, alkynyl, cycloalkyl, aryl, or aralkyl.

$R_7$ is a $C_3$-$C_{16}$ alkyl, wherein the $C_3$-$C_{16}$ alkyl is not a substituted alkyl having both a carboxyl group and an amino group. R7 may also be alkenyl, alkynyl, ketone, amino alcohol, or an amino acid selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan, OR', Se—R', S—R'. R' for OR' is selected from the group consisting of H, alkyl, cycloalkyl, aryl, aralkyl, and heterocyclyl. R' for Se—R' is selected from the group consisting of H, $C_3$-$C_{16}$ alkyl, cycloalkyl, aryl, aralkyl, and heterocyclyl. R' for S—R' is selected from the group consisting of H, $C_3$-$C_{16}$ alkyl, cycloalkyl, aryl, aralkyl, and heterocyclyl. $R_8$ is hydrogen, azido, alkyl, alkenyl, or alkynyl. The composition may also comprise a carrier.

BRIEF DESCRIPTION OF THE DRAWINGS

A brief description of the drawings is as follows. The patent or application file contains at least one drawing executed in color. Copies of this patent or patent application publication with color drawing(s) will be provided by the Office upon request and payment of the necessary fee.

FIGS. 1A-1B show the effect of 150 ppb of each of Compound C, Compound D, Compound E, Compound H, Compound I, and Compound J, respectively, on the viability of IMR-32 neuronal cells as indicated by OD490. * refers to P<0.05 when compared to control or its sulfur analog group. @ refers to P<0.05 when compared to its sulfur analog group.

FIG. 1A shows cell viability after 24 hours of incubation with the compounds.

FIG. 1B shows cell viability after 72 hours of incubation with the compounds.

FIGS. 2A-2K show enhanced mitochondrial (MT) potential, elevated PGC1a protein expression, inhibited UCP2 and UCP3 mRNA expression and a trend towards reduced UCP5

(SLC25A14) mRNA expression in human IMR-32 cells after treatment with Compound C.

FIG. 2A shows a representative fluorescence micrograph of IMR-32 cells without any treatment with Compound C.

FIG. 2B shows a representative fluorescence micrograph of IMR-32 cells treated with 75 ppb Compound C for 6 hours. Red fluorescence indicates mitochondrial potential signals while cell nuclei stain in blue color.

FIG. 2C shows a representative fluorescence micrograph of IMR-32 cells treated with 150 ppb Compound C for 6 hours. Red fluorescence indicates mitochondrial potential signals while cell nuclei stain in blue color.

FIG. 2D shows quantitative analysis of MT potential (normalized by the fluorescence intensities of stained cell nuclei) in IMR-32 cells after Compound C treatment for 6 hours, when compared to control (0 ppb) group.

FIG. 2E shows quantitative analysis of MT potential (normalized by the fluorescence intensities of stained cell nuclei) in IMR-32 cells after Compound C treatment for 24 hours, when compared to control (0 ppb) group.

FIG. 2F is a Western blot showing PGC1a protein expression in IMR-32 cells treated with control or with 150 ppb of Compound C, Compound D, or Compound E for 24 hours.

FIG. 2G is a bar graph showing quantitative analysis of PGC1a protein levels (normalized by ACTB protein level) in IMR-32 cells after treatment with Compound C, Compound D or Compound E for 24 hours shown in FIG. 2F.

FIG. 2H is a bar graph that shows the relative mRNA levels of UCP2, UCP3, UCP1, SLC25A14 (UCP5), and SLC25A27 (UCP4) expressed in normal IMR-32 cells as determined by quantitative RT-PCR (QRTPCR).

FIG. 2I is a bar graph that shows relative UCP2 mRNA levels in IMR-32 cells after treatment with 150 ppb Compound C, Compound D, or Compound E for 6 hours.

FIG. 2J is a bar graph showing relative UCP3 mRNA levels in IMR-32 cells treated with control, or 150 ppb Compound C, Compound D, or Compound E for 6 hours.

FIG. 2K is a bar graph showing relative SLC25A14 (UCP5) mRNA levels in IMR-32 cells treated with control or 150 ppb Compound C, Compound D, or Compound E for 6 hours.

FIGS. 3A-3I show the effect of Compound C, Compound D, and Compound E on mRNA expression and protein levels of γ-secretase complex genes, PSEN1 and NICASTRIN, in IMR-32 cells.

Figure 3A:
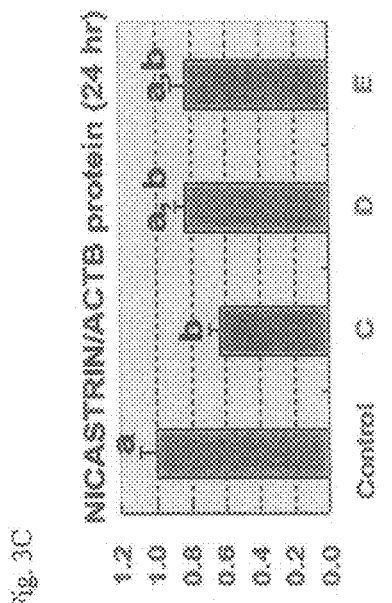

FIG. 3A is a Western blot showing proteins including PSEN1 and NICASTRIN associated with plaque formation in Alzheimer's Disease (AD) in IMR-32 cells treated with control or 150 ppb Compound C, Compound D, or Compound E for 24 hours.

Figure 3B:
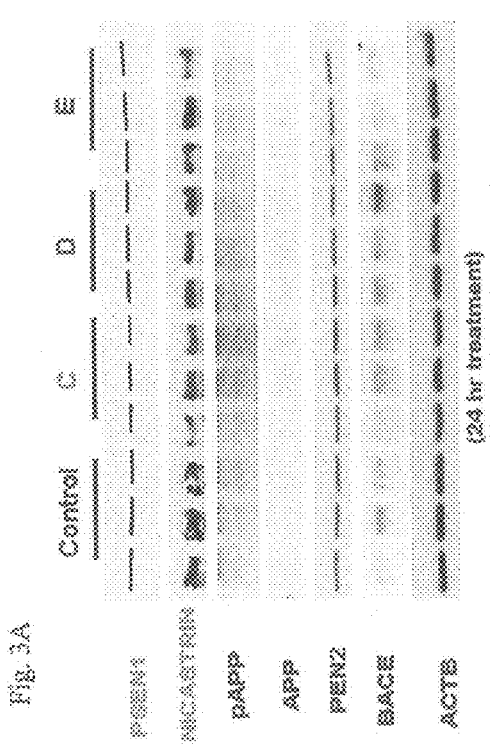

FIG. 3B is a bar graph showing quantitative analysis of PSEN1 protein levels in the gel of FIG. 3A.

Figure 3C:
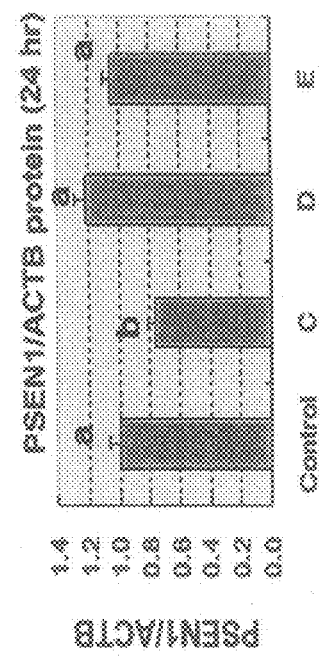

FIG. 3C is a bar graph showing quantitative analysis of NICASTRIN protein levels in the gel of FIG. 3A.

Figure 3D:
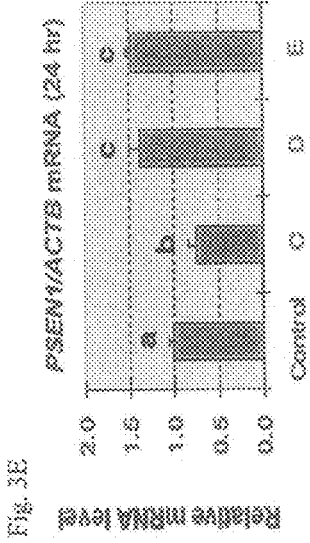

FIG. 3D is a bar graph showing relative PSEN1 mRNA levels in IMR-32 cells treated with control or 150 ppb Compound C, Compound D, or Compound E for 6 hours.

Figure 3F:
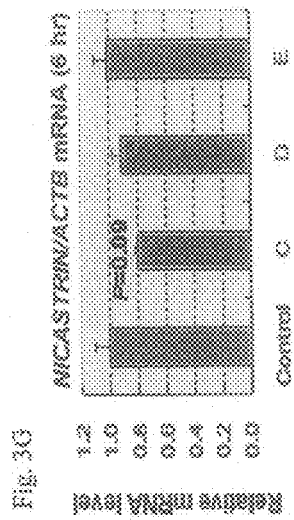
Figure 3H:
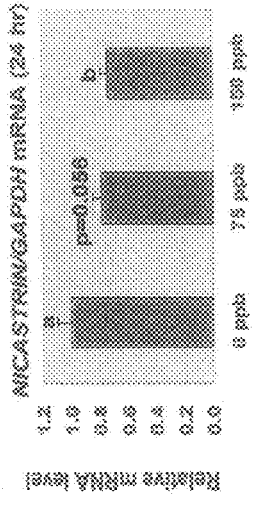
Figure 3E:
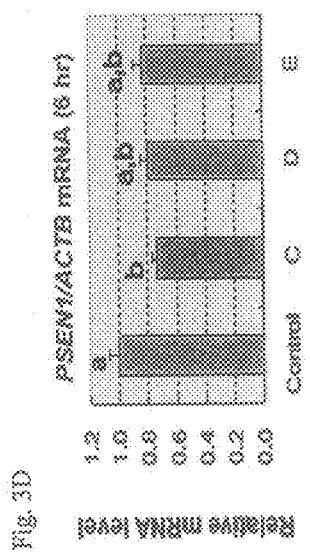

FIG. 3E is a bar graph showing relative PSEN1 mRNA levels in IMR-32 cells treated with control or Compound C, Compound D, or Compound E for 24 hours.

FIG. 3F is a bar graph showing relative PSEN1 mRNA levels in IMR-32 cells treated with 0 ppb (control), 75 ppb, or 150 ppb of Compound C for 24 hours.

Figure 3G:
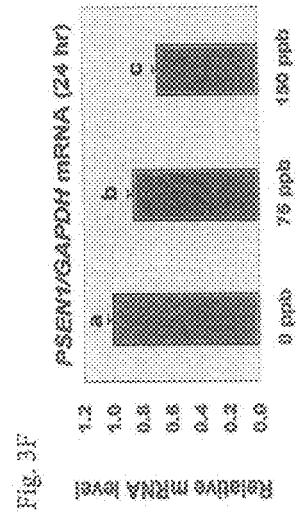

FIG. 3G is a bar graph showing relative NICASTRIN mRNA levels in IMR-32 cells treated with control or Compound C, Compound D, or Compound E for 6 hours.

FIG. 3H is a bar graph showing relative NICASTRIN mRNA levels in IMR-32 cells treated with control or Compound C, Compound D, or Compound E for 24 hours.

Figure 3I:
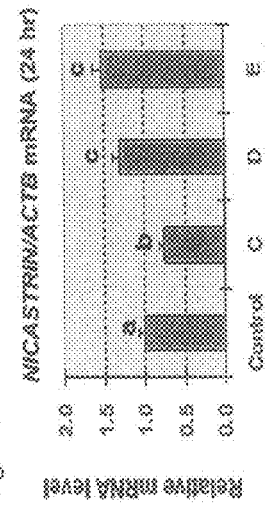

FIG. 3I is a bar graph showing relative NICASTRIN mRNA levels in IMR-32 cells treated with 0 ppb (control), 75 ppb, or 150 ppb of Compound C for 24 hours.

FIGS. 4A-4H show the effect of Compound C on phosphorylated Tau protein, and GSK3B mRNA and protein expression in IMR-32 cells.

Figure 4A:
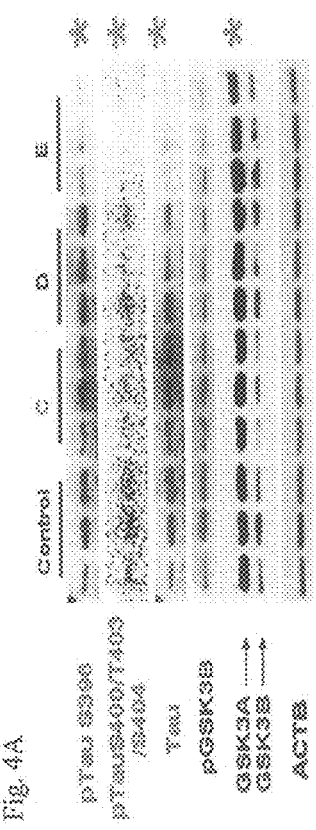

FIG. 4A is a Western blot showing the levels of proteins associated with tangle formation in Alzheimer's Disease (AD) including phosphorylated Tau and GSK3B in IMR-32 cells treated with control or 150 ppb of Compound C, Compound D, or Compound E for 24 hours.

Figure 4C:
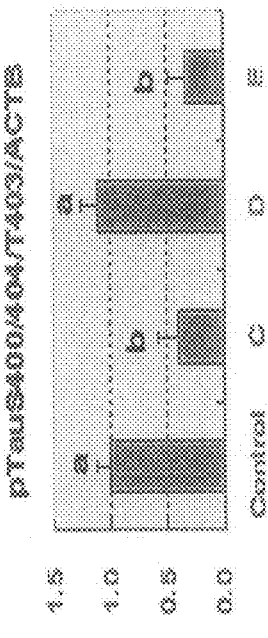
Figure 4E:
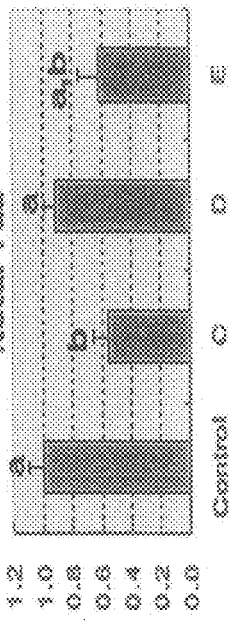
Figure 4B:
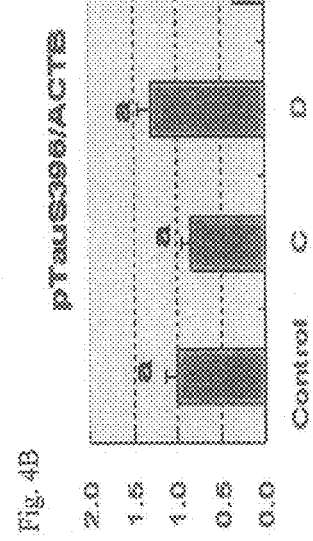

FIG. 4B is a bar graph showing quantitative analysis of phosphorylated Tau S396 (at serine 396) protein levels in the gel of FIG. 4A.

FIG. 4C is a bar graph showing quantitative analysis of phosphorylated Tau S400/S404/T403 (at serine residues 400, and 404; threonine at 403) protein levels in the gel of FIG. 4A.

Figure 4D:
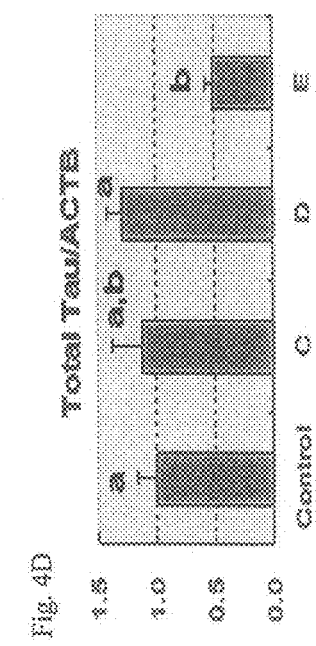

FIG. 4D is a bar graph showing quantitative analysis of Total Tau protein levels in the gel of FIG. 4A.

FIG. 4E is a bar graph showing quantitative analysis of phosphorylated Tau S396 and phosphorylated Tau S400/S404/T403 combined protein levels per Total Tau protein level in the gel of FIG. 4A.

Figure 4F:
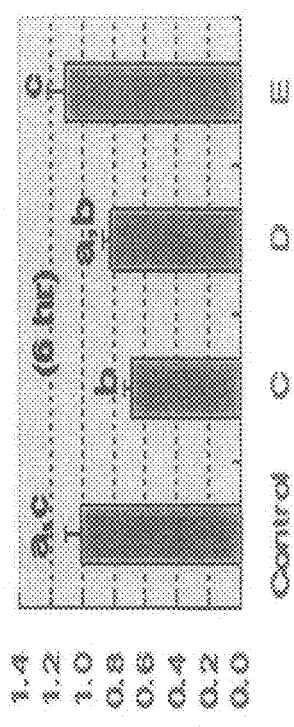

FIG. 4F is a bar graph showing quantitative analysis of GSK3B protein levels in the gel of FIG. 4A.

Figure 4G:
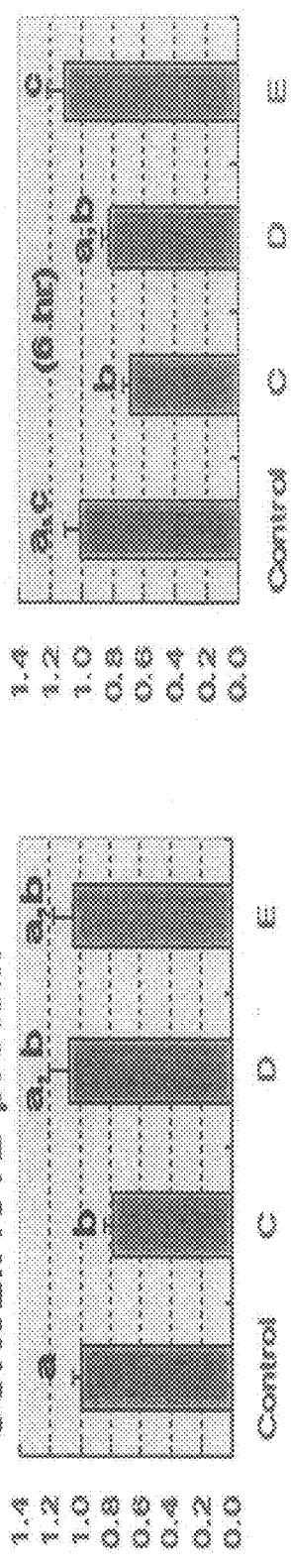

FIG. 4G is a bar graph showing relative GSK3B mRNA levels in IMR-32 cells treated with control or 150 ppb of Compound C, Compound D, or Compound E for 6 hours.

Figure 4H:
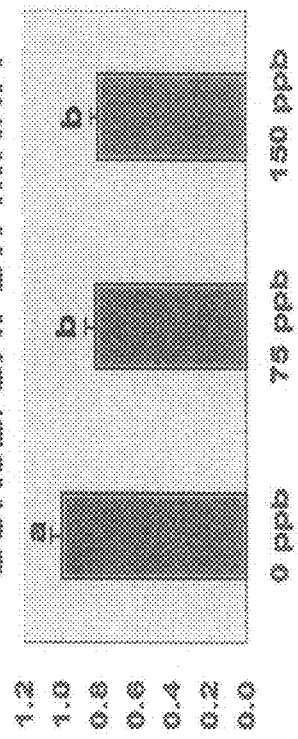

FIG. 4H is a bar graph showing relative GSK3B mRNA levels in IMR-32 cells treated with 0 ppb (control), 75 ppb, or 150 ppb of Compound C for 24 hours.

FIGS. 5A-5B the effect of Compound C, Compound D, and Compound E on p38 protein levels in IMR-32 cells.

FIG. 5A is a Western blot showing p38 protein expression in IMR-32 cells treated with control or 150 ppb of Compound C, Compound D, or Compound E for 24 hours.

FIG. 5B is a bar graph showing quantitative analysis of p38 protein levels in the gel of FIG. 5A.

Figure 6A:
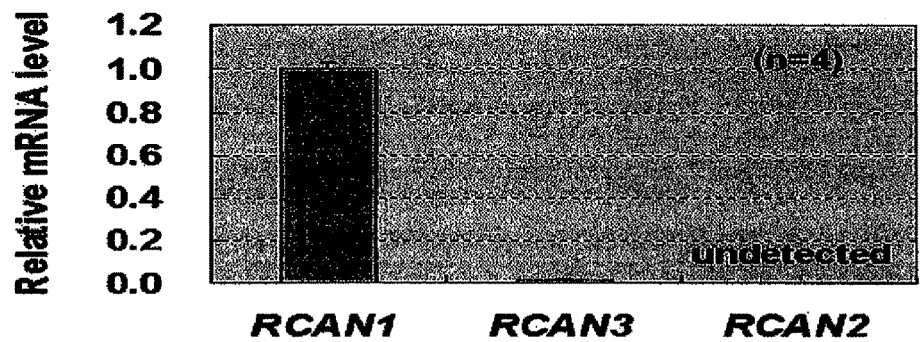
Figure 6B:
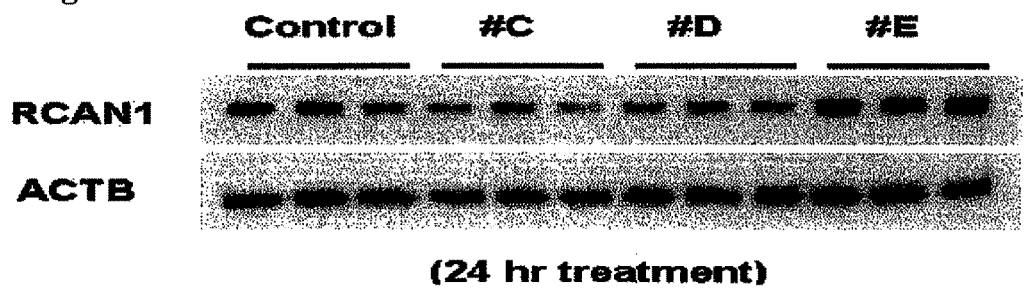
Figure 6C:
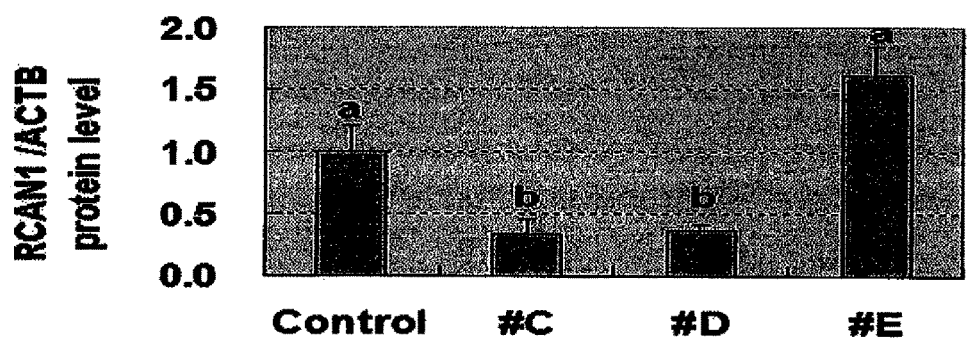

FIGS. 6A-6C show the effect of Compound C, Compound D, and Compound E on mRNA expression and protein levels of RCAN genes in IMR-32 cells.

FIG. 6A is a bar graph showing relative RCAN1, RCAN2, and RCAN3 mRNA expression levels in normal IMR-32 cells treated with a control for 24 hours.

FIG. 6B is a Western blot showing RCAN1 protein expression in IMR-32 cells treated with control or 150 ppb of Compound C, Compound D, or Compound for 24 hours.

FIG. 6C is a bar graph showing quantitative analysis of RCAN1 protein levels in the gel of FIG. 6B.

FIGS. 7A-7F show the effect of Compound C, Compound D, and Compound E on mRNA expression and protein levels of PPARG and APOE in IMR-32 cells.

FIG. 7A is a Western blot showing PPARG protein expression in IMR-32 cells treated with control or 150 ppb of Compound C, Compound D, or Compound E for 6 hours.

FIG. 7B is a bar graph showing quantitative analysis of PPARG protein levels in the gel of FIG. 7A.

FIG. 7C is a bar graph showing relative PPARG mRNA expression levels in IMR-32 cells treated with. control or 150 ppb of Compound C, Compound D, or Compound E for 6 hours.

FIG. 7D is a Western blot showing APOE4 protein expression in IMR-32 cells treated with control or 150 ppb of Compound C, Compound D, or Compound E for 24 hours.

FIG. 7E is a bar graph showing quantitative analysis of APOE4 protein levels in the gel of FIG. 7D.

FIG. 7F is a bar graph showing relative APOE mRNA expression levels in IMR-32 cells treated with control or 150 ppb of Compound C, Compound D, or Compound E for 24 hours.

FIGS. 8A-8D show the effect of Compound C, Compound D, and Compound E on the mRNA expression and protein levels of G6PC, INSR, and IGF1R genes in IMR-32 cells.

Figure 8A:
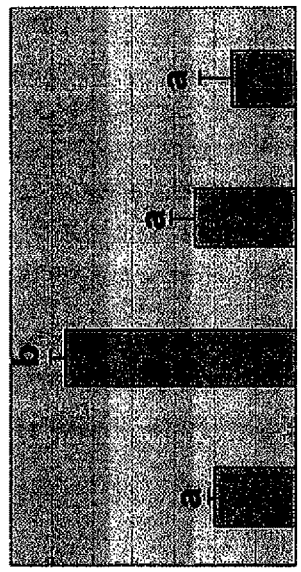

FIG. 8A is a Western blot showing G6PC protein expression in IMR-32 cells treated with control or 150 ppb of Compound C, Compound D, or Compound E for 24 hours.

Figure 8B:
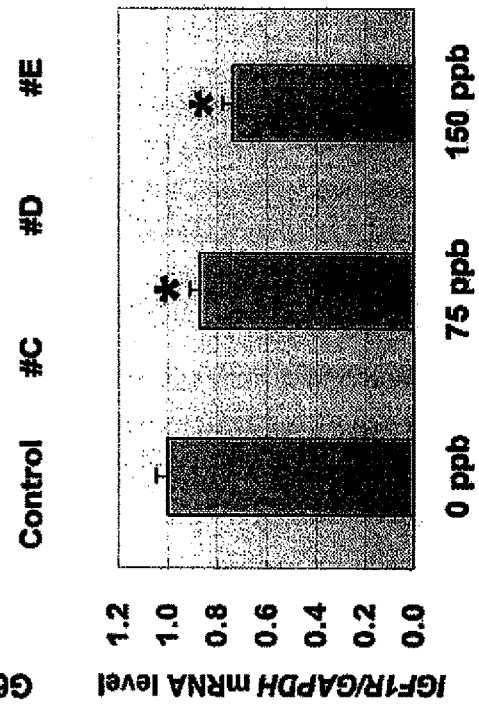

FIG. 8B is a graph showing quantitative analysis of G6PC protein levels in the gel of FIG. 8A.

Figure 8C:
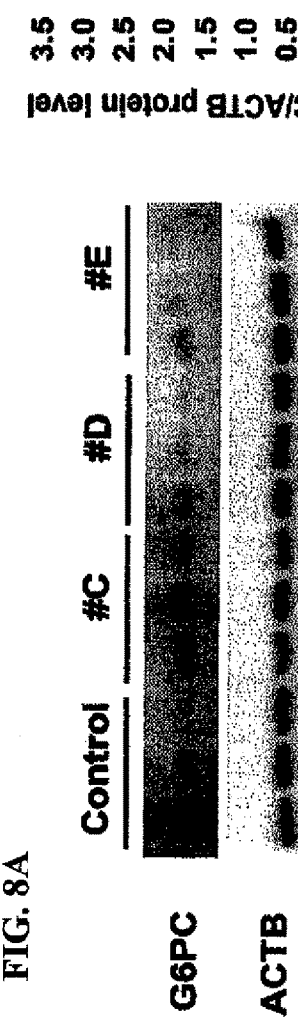

FIG. 8C is a graph showing relative INSR mRNA levels in IMR-32 cells treated with 0 ppb (control), 75 ppb, or 150 ppb of Compound C for 24 hours.

Figure 8D:
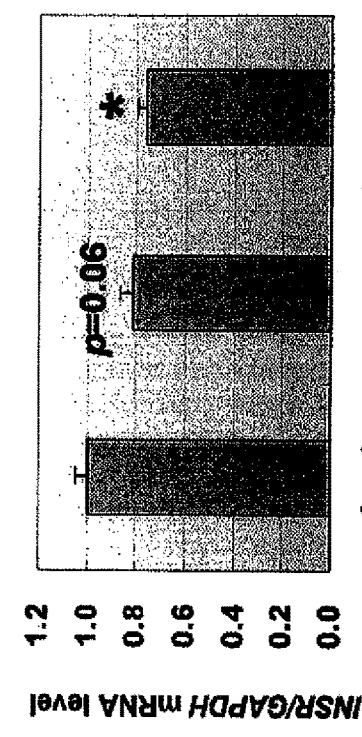

FIG. 8D is a graph showing relative IGF1R mRNA levels in IMR-32 cells treated with 0 ppb (control), 75 ppb, or 150 ppb of Compound C for 24 hours.

FIGS. 9A-9C show the effect of Compound C, Compound D, and Compound E on protein levels of phosphorylated FOXO4 in IMR-32 cells.

FIG. 9A is a Western blot showing signaling proteins in IMR-32 cells treated with control or Compound C, Compound D, or Compound E for 6 hours and 24 hours.

FIG. 9B is a bar graph showing quantitative analysis of phosphorylated FOXO4 protein levels at 6 hours in the gel of FIG. 9A.

FIG. 9C is a bar graph showing quantitative analysis of phosphorylated FOXO4 protein levels at 24 hours in the gel of FIG. 9A.

Figure 10A:
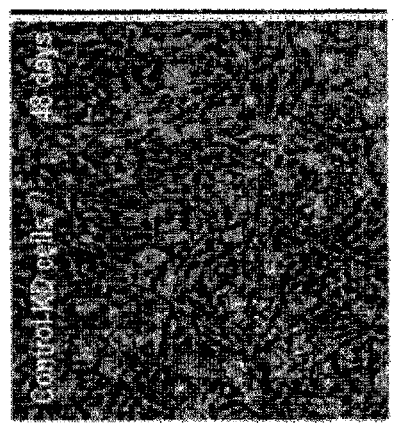
Figure 10B:
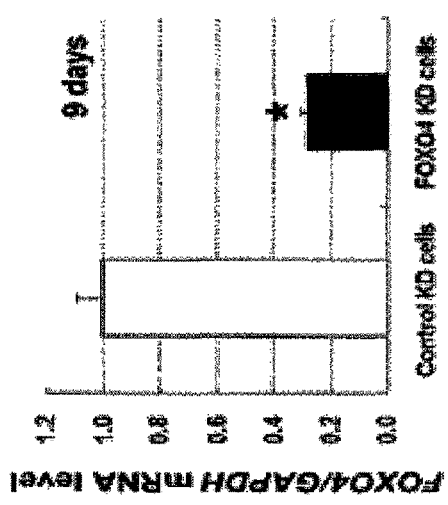
Figure 10C:
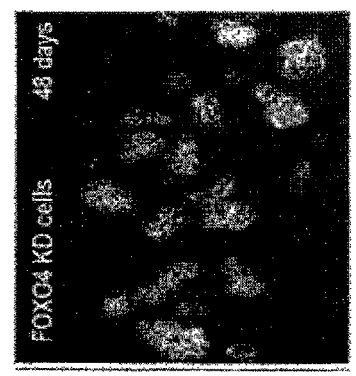

FIGS. 10A-10C show knock-down of the expression of FOXO4 gene in IMR-32 cells and the effect of the knock-down on cell viability.

FIG. 10A is a graph showing quantitative analysis of relative FOXO4 mRNA levels in control IMR-32 cells and FOXO4 knock-down (KD) IMR-32 cells cultured with control for 9 days. * $P<0.05$ when compared to control cells.

FIG. 10B is a representative photo of control IMR-32 cells after 48 days in culture.

FIG. 10C shows loss of cell viability in FOXO4 knock-down (KD) IMR-32 cells after 48 days in culture.

Figures 11A, 11B:
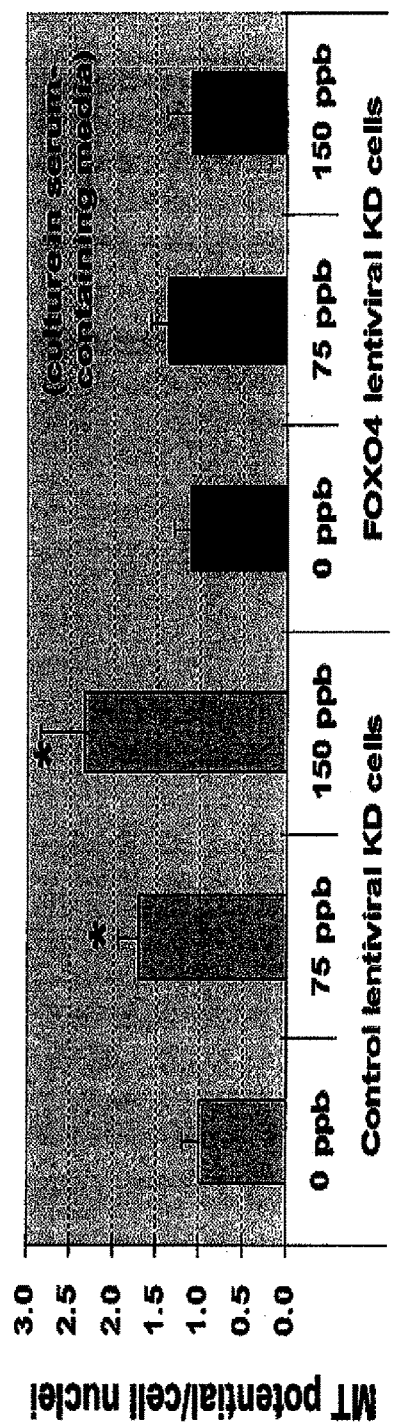

FIGS. 11A-11B show the effect of Compound C on mitochondrial potential in control IMR-32 cells and FOXO4 knock-down IMR-32 cells.

FIG. 11A is a bar graph showing a dose-dependent response to 0 ppb (control), 75 ppb, or 150 ppb of Compound C on mitochondrial potential in control IMR-32 cells and FOXO4 knock-down (KD) IMR-32 cells cultured in media with serum. * refers to $P<0.05$ when compared to control (0 ppb group in control lentiviral KD cells).

FIG. 11B is a bar graph showing a dose-dependent response to 0 ppb (control), 75 ppb, and 150 ppb of Compound C on mitochondrial potential in control IMR-32 cells and FOXO4 knock-down (KD) IMR-32 cells cultured in media without serum. * refers to $P<0.05$ when compared to control cells (0 ppb group in control lentiviral KD cells).

FIGS. 12A-12D show the effect of Compound C on mRNA expression levels of NICASTRIN, GSK3B, PPARG, and APOE genes in control IMR-32 cells and FOXO4 knock-down IMR-32 cells.

Figure 12A:
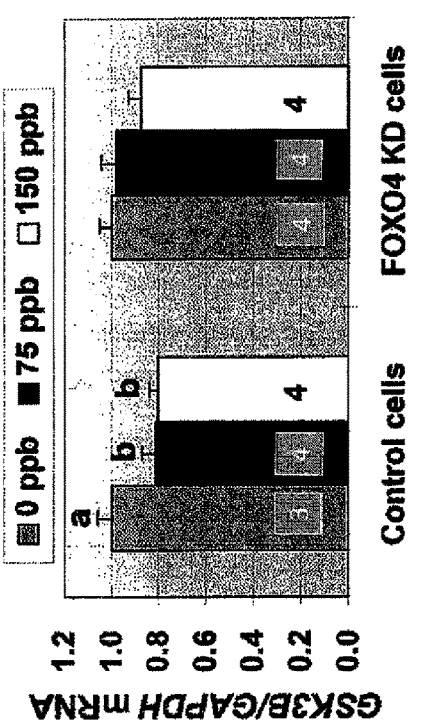

FIG. 12A is a bar graph showing response of relative NICASTRIN mRNA levels to 0 ppb (control), 75 ppb, or 150 ppb of Compound C in control IMR-32 cells and FOXO4 knock-down (KD) IMR-32 cells.

Figure 12B:
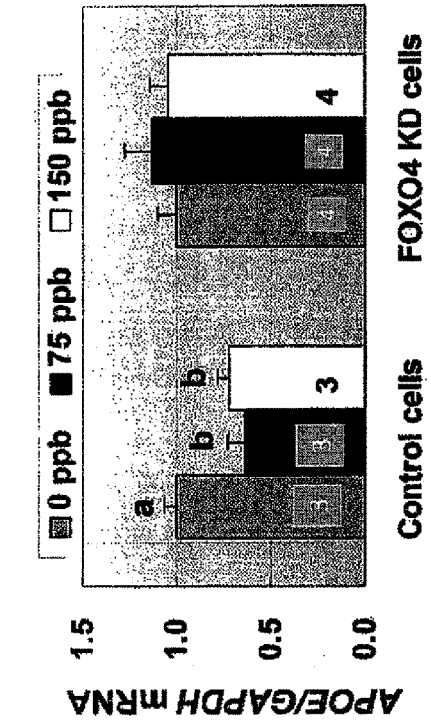

FIG. 12B is a bar graph showing response of relative GSK3B mRNA levels to 0 ppb (control), 75 ppb, or 150 ppb of Compound C in control IMR-32 cells and FOXO4 knock-down (KD) IMR-32 cells.

Figure 12C:
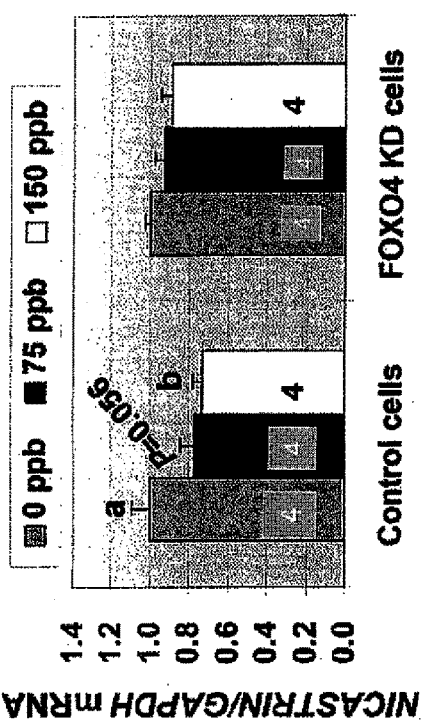

FIG. 12C is a bar graph showing response of relative PPARG mRNA levels to 0 ppb (control), 75 ppb, or 150 ppb of Compound C in control IMR-32 cells and FOXO4 knock-down (KD) IMR-32 cells.

Figure 12D:
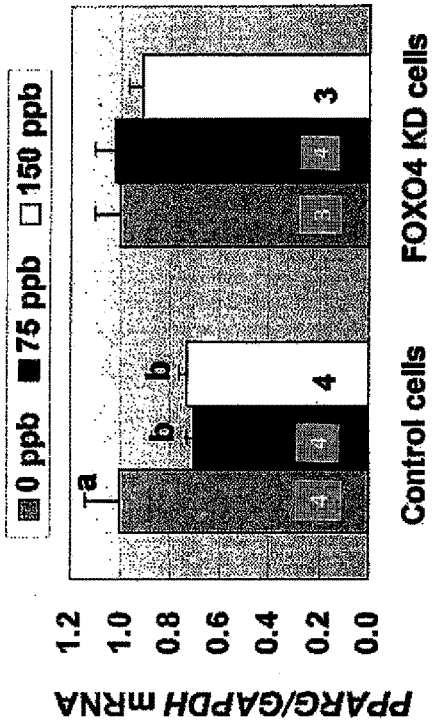

FIG. 12D is a bar graph showing response of relative APOE mRNA levels to 0 ppb (control), 75 ppb, or 150 ppb of Compound C in control IMR-32 cells and FOXO4 knock-down (KD) IMR-32 cells.

FIGS. 13A-13E show the effect of Compound C on mRNA expression levels of MAPK genes in control IMR-32 cells and FOXO4 knock-down IMR-32 cells.

FIG. 13A is a bar graph showing relative MAPK11, MAPK12, MAPK13, AND MAPK14 mRNA levels in normal control IMR-32 cells.

FIG. 13B is a bar graph showing response of relative MAPK11 mRNA levels to 0 ppb (control), 75 ppb, or 150 ppb of Compound C in control IMR-32 cells and FOXO4 knock-down (KD) IMR-32 cells. *refers to a $P<0.05$ when compared to control cells (0 ppb).

FIG. 13C is a bar graph showing response of relative MAPK12 mRNA levels to 0 ppb (control), 75 ppb, or 150 ppb of Compound C in control IMR-32 cells and FOXO4 knock-down (KD) IMR-32 cells. *refers to a $P<0.05$ when compared to control cells (0 ppb).

FIG. 13D is a bar graph showing response of relative MAPK13 mRNA levels to 0 ppb (control), 75 ppb, or 150 ppb of Compound C in control IMR-32 cells and FOXO4 knock-down (KD) IMR-32 cells. *refers to a $P<0.05$ when compared to control cells (0 ppb).

FIG. 13E is a bar graph showing response of relative MAPK14 mRNA levels to 0 ppb (control), 75 ppb, or 150 ppb of Compound C in control IMR-32 cells and FOXO4 knock-down (KD) IMR-32 cells. *refers to a $P<0.05$ when compared to control cells (0 ppb).

FIGS. 14A-14C show the effect of Compound C on mRNA expression levels of RCAN genes in control IMR-32 cells and FOXO4 knock-down IMR-32 cells.

FIG. 14A is a schematic of the RCAN1 gene structure, including a FOXO4 binding motif (oval) located in the promoter and upstream of RCAN1.1 and RCAN1.4 gene transcripts.

FIG. 14B is a bar graph showing response of relative RCAN1 mRNA levels to 0 ppb (control), 75 ppb, or 150 ppb of Compound C in control IMR-32 cells and FOXO4 knock-down (KD) IMR-32 cells. *refers to a $P<0.05$ when compared to control (0 ppb).

FIG. 14C is a bar graph showing response of relative RCAN1.1 mRNA levels to 0 ppb (control), 75 ppb, or 150 ppb of Compound C in control IMR-32 cells and FOXO4 knock-down (KD) IMR-32 cells. *refers to a $P<0.05$ when compared to control cells with vehicle treatment (0 ppb).

FIGS. 15A-15H show the effect on plaque deposits and Aβ1-42 levels, and the altered expression of key genes for Aβ production, degradation, Tau phosphorylation and neuroinflammation in the brains of APP/PS1 mice after Compound C treatment.

FIG. 15A-B Photographs showing Aβ plaque deposits (arrows) in the cortical region of (A) control and (B)

Compound C-treated APP/PS1 mouse brains by immunohistochemistry (IHC) using a specific antibody against Aβ1-42.

FIG. 15C-D Photographs showing Aβ plaque deposits (arrows) in the hippocampal regions of (C) control and (D) Compound C-treated APP/PS1 mouse brains by immunohistochemistry (IHC) using a specific antibody against Aβ1-42.

Figure 15E:
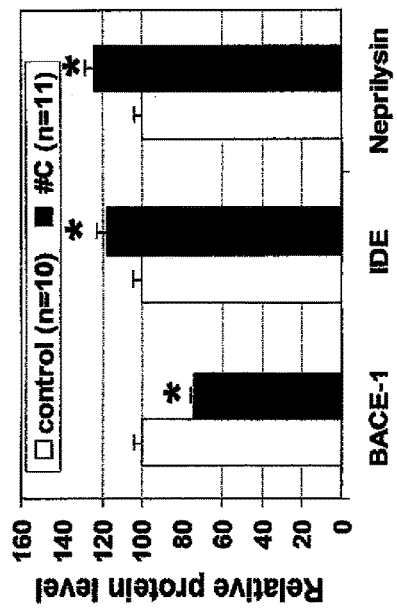

FIG. 15E ELISA of insoluble [Formic Acid (FA)-soluble] Aβ1-42 levels in the brains of control and Compound C-treated APP/PS1 mice. * refers to P<0.05 when compared to control group.

Figure 15F:
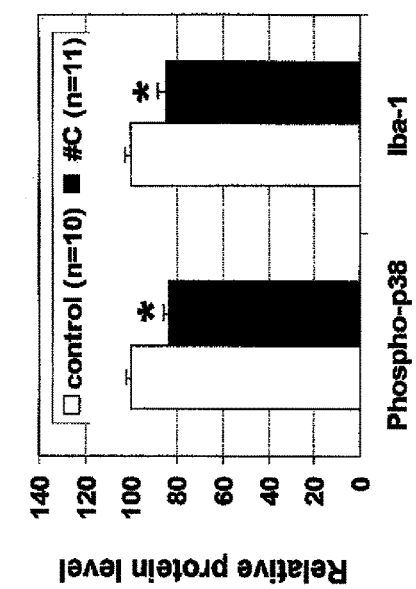

FIG. 15F Quantitative analysis of Western blots showing the reduced BACE1 and increased insulin degrading enzyme (IDE) and Neprilysin protein expression in the brains of control and Compound C-treated APP/PS1 mice. * refers to P<0.05 when compared to control group.

Figure 15G:
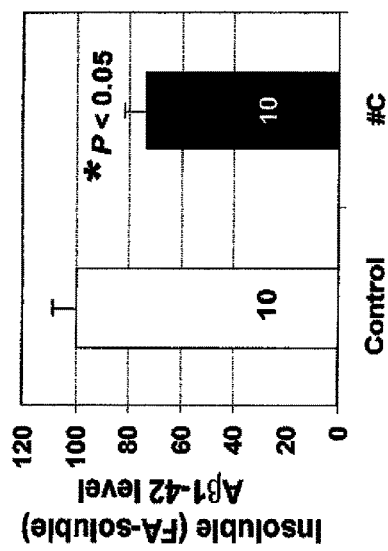

FIG. 15G Neprilysin mRNA expression in the brains of control and Compound C-treated APP/PS1 mice. * refers to P<0.05 when compared to control group.

Figure 15H:
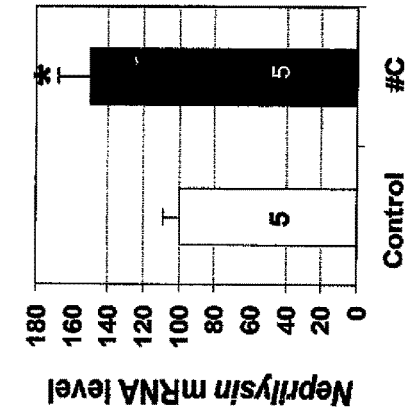

FIG. 15H Quantitative analysis of Western blots showing the reduced phosphorylated-p38 and ionized calcium binding adaptor molecule 1 (Iba-1) proteins in the brains of Compound C-treated APP/PS1 mice. * refers to P<0.05 when compared to control group.

Figure 16:
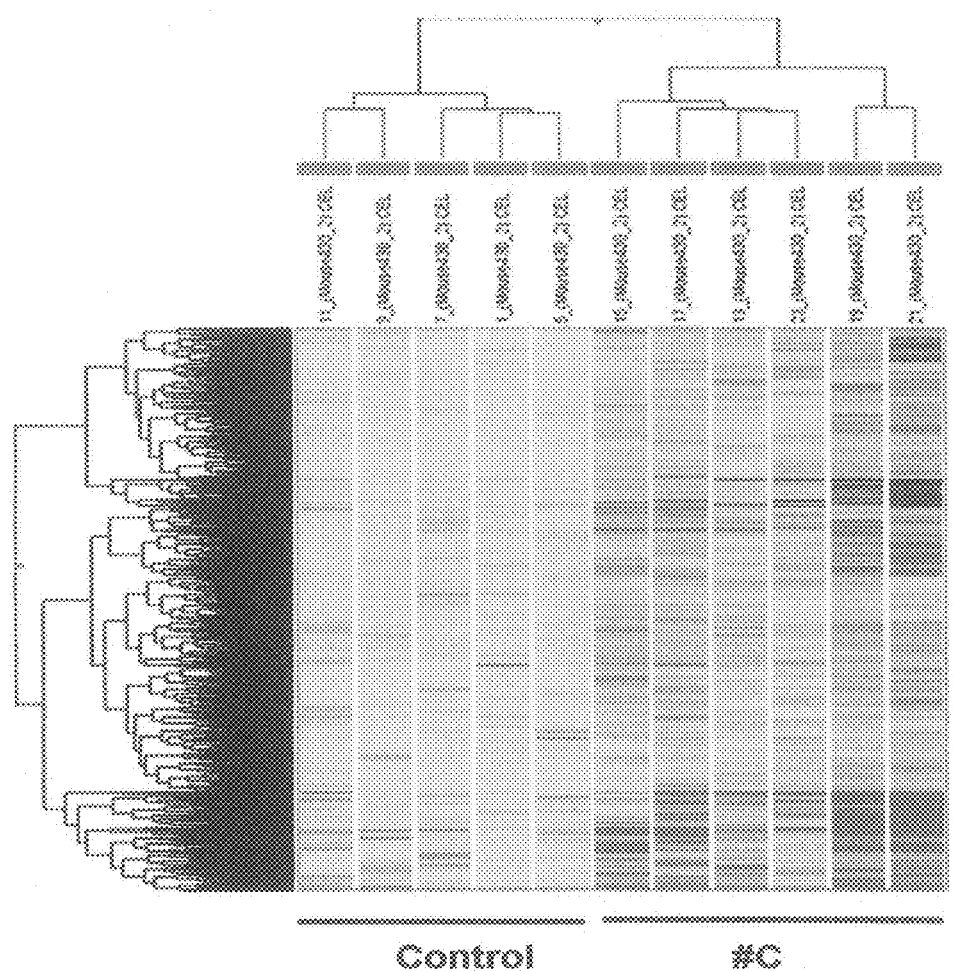

FIG. 16 shows the heatmap of 2217 significantly altered gene transcripts in the brains of APP/PS1 mice after Compound C treatment by microarray analysis followed by unsupervised hierarchical clustering analysis.

FIGS. 17A-17C show the effect of Compound C on relative mRNA expression levels of Zic genes and various genes involved in brain development and neuronal functions, including Foxp2, Drd1a, Tac1, Sez6, Penk, Ddx5, Rarb, Meis2, Ddx5, Gpr88, Pde10a, Akap5 and Isl1 in mice brains after mice were fed a control diet or a diet containing Compound C.

FIG. 17A is a bar graph showing relative mRNA expression levels of Zic1-5 genes in normal mice brains.

FIG. 17B is a bar graph showing relative mRNA expression levels of Zic1-5 genes in APP/PS1 mice brains after mice were fed a control diet or a diet containing Compound C.

FIG. 17C is a bar graph showing relative mRNA expression levels of various genes involved in brain development and neuronal functions, including Foxp2, Drd1a, Tac1, Sez6, Penk, Ddx5, Rarb, Meis2, Ddx5, Gpr88, Pde10a, Akap5 and Isl1 in APP/PS1 mice brains after mice were fed a control diet or a diet containing Compound C.

FIGS. 18A-18C show the inhibition of Foxo3 and Foxo4 phosphorylation in the brains of APP/PS1 mice after Compound C treatment.

FIG. 18A is a Western blot showing phosphorylated Foxo3 (pFoxo3) and phosphorylated Foxo4 (pFoxo 4) protein expression in brain tissue of APP/PS1 mice after Compound C treatment.

FIG. 18B is a bar graph showing quantitative analysis of phosphorylated Foxo3 protein levels in the gel of FIG. 18A.

FIG. 18C is a bar graph showing quantitative analysis of phosphorylated Foxo4 protein levels in the gel of FIG. 18A.

Figure 19:
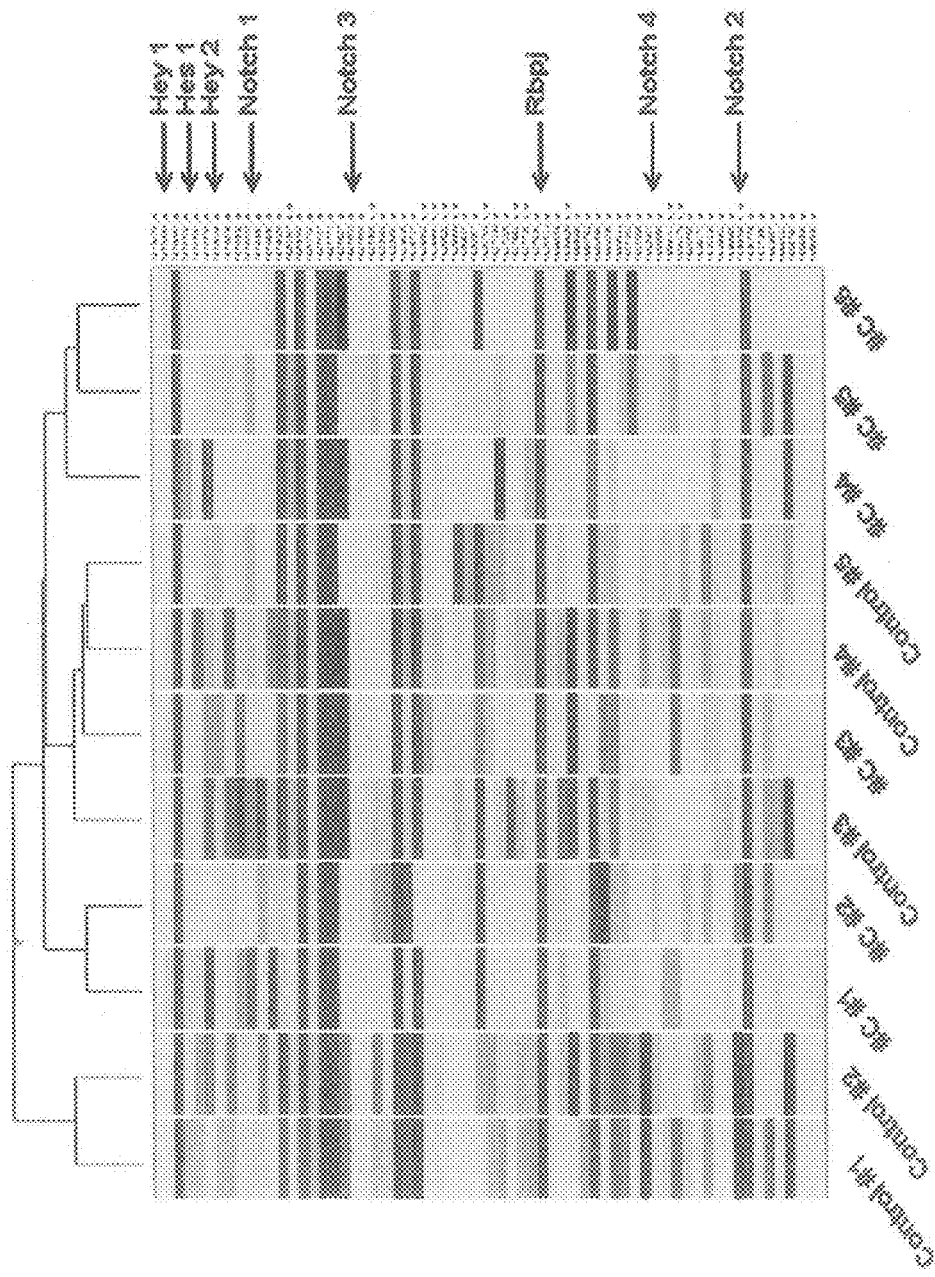

FIG. 19 shows a heatmap of the expression of 65 Notch signaling molecules in APP/PS1 mouse brains after treatment with Compound C.

DETAILED DESCRIPTION

Definitions

As used herein, the terms "administration" and "administering" refer to the act of giving a drug, prodrug, or other agent, or therapeutic treatment (e.g., compositions of the present application) to a subject in vivo, in vitro or to ex vivo cells, tissues, and organs. The compounds and compositions of the present disclosure may be given to a subject by any route of administration known in the art. Exemplary routes of administration to the human body can be through the eyes (ophthalmic), mouth (oral), skin (topical or transdermal), nose (nasal), lungs (inhalant), oral mucosa (buccal), brain, ear, rectal, vaginal, or by injection. Routes of injection may be administered intravenously, subcutaneously, intratumorally, intraperitoneally, and the like.

The term "alkyl" refers to a branched or unbranched saturated hydrocarbon group of 1 to 24 carbon atoms, and preferably, at least three or at least four carbon atoms. In some embodiments, an "alkyl" group contains 1 to 16 carbon atoms (i.e., $C_{1-16}$ alkyl), specifically, in other embodiments, the alkyl comprises 3 to 16 atoms (i.e., $C_{3-16}$ alkyl). The alkyl group may be optionally substituted with an acyl, amino, amido, azido, carboxyl, alkyl, aryl, halo, guanidinyl, oxo, sulfanyl, sulfenyl, sulfonyl, heterocyclyl or hydroxyl group. Additional examples of an alkyl group include, but are not limited to methyl, ethyl, propyl, iso-propyl, butyl, iso-butyl, secondary-butyl, tertiary-butyl, pentyl, iso-pentyl, neo-pentyl, hexyl, iso-hexyl, 3-methylpentyl, 2,3-dimethylbutyl, neo-hexyl, heptyl, octyl, nonyl, decyl, undecyl, dodecyl, tridecyl, tetradecyl, pentadecyl, and hexadecyl.

In one embodiment of a $C_3$-$C_{16}$ alkyl, the alkyl is not a substituted alkyl. In other embodiments, the substituted alkyl does not have both a carboxyl group and an amino group. In further embodiments, the $C_3$-$C_{16}$ alkyl is not a substituted alkyl having both a carboxyl group and an amino group.

The term "alkali metal" refers to metallic salts that include, but are not limited to, appropriate alkali metal salts (e.g., Group IA) salts, alkaline earth metal salts (e.g., Group IIA), and other physiologically acceptable metals. Metallic salts can be made from aluminum, calcium, lithium, magnesium, potassium, sodium, zinc or combinations thereof.

The term "alkenyl" refers to a straight or branched carbon chain containing at least one carbon-carbon double bond. In some embodiments, "alkenyl" refers to a hydrocarbon containing 1, 2, 3, 4, 5, 6, 7, 8, 9 or 10 carbon atoms (i.e., $C_{1-10}$ alkenyl). Examples of an alkenyl group include, but are not limited to, ethene, propene, butene, pentene, hexene, heptene, octene, nonene and decene. The alkenyl group may be optionally substituted with an amino, alkyl, halo, or hydroxyl group.

The term "amido" refers to either a C-amido group, such as a —CONR'R" moiety or an N amido group, such as —NR'COR" moiety, wherein R and R" may independently be hydrogen, alkyl, alkenyl, alkynyl, alkoxy, carbocyclic, heterocylic, aryl, or aralkyl. A "sulfoamido" group includes the —NR'—SO$_2$—R" moiety, wherein the R and R" may be hydrogen, alkyl, aryl, or aralkyl.

The term "alkynyl" refers to a straight or branched carbon chain comprising at least one carbon-carbon triple bond. In exemplary embodiments, "alkynyl" refers to a hydrocarbon containing 2, 3, 4, 5, 6, 7, 8, 9 or 10 carbon atoms (i.e., $C_{2-10}$ alkynyl). Examples of an alkynyl group include, but are not limited to, ethyne, propyne, butyne, pentyne, hexyne, heptyne, octyne, nonyne and decyne. The alkynyl group may be optionally substituted with an amino, alkyl, halo, or hydroxyl group.

The term "aryl" refers to a carbocyclic aromatic system comprising one, two or three rings. The rings may be attached together in a pendant manner or may be fused together. The term "aryl" encompasses aromatic groups such as phenyl, naphthyl, tetrahydronaphthyl, tetralin, indane, indene, and biphenyl. The aryl group may optionally be substituted with an amino, alkyl, halo, hydroxyl, carbocyclic, heterocyclic, or another aryl group.

A "combination" as used herein refers to a mixture of one or more components or a plurality of components. The combination may comprise, consist essentially of, or consist of compounds, compositions, components, constituents, elements, moieties, or molecules.

The term "fused" means that a second ring is present (i.e., attached or formed) by having two adjacent atoms in common (i.e., shared) with the first ring. The term "fused" is equivalent to the terms "condensed," "attached," and "bound," which may be used interchangeably.

The term "cycloalkyl" refers to a monocyclic saturated or partially saturated carbon ring, comprising a number of ring atoms. In some embodiments, "cycloalkyl" refers to a carbon ring containing 3-12 ring atoms (i.e., $C_{3-12}$ cycloalkyl). As used herein, a cycloalkyl encompasses monocyclo, bridged, spiro, fused, bicyclo and tricyclo ring structures. Examples of a cycloalkyl group include, but are not limited to, cyclopropyl, cyclobutyl, cyclopentyl, cyclopentenyl, cyclohexyl, cyclohexenyl, cycloheptyl, cycloheptenyl, norbornyl, decalin, adamantyl, and cyclooctyl. The cycloalkyl group may be optionally substituted with an amino, alkyl, halo, or hydroxyl group.

The term "aralkyl" refers to aryl-substituted alkyl moieties. Aralkyl groups may be "lower aralkyl" groups, where the aryl groups are attached to alkyl groups having one to six carbon atoms. Examples of aralkyl groups include benzyl, diphenylmethyl, triphenylmethyl, phenylethyl, and diphenylethyl. The terms "benzyl" and "phenylmethyl" are interchangeable. In some embodiments, the alkyl is a $C_3$-$C_{16}$ alkyl. In other embodiments, the alkyl is not a substituted alkyl having both a carboxyl group and an amino group.

The term "aryloxy" refers to an aryl group attached to an oxygen atom. The aryloxy group may optionally be substituted with a halo, hydroxyl, or alkyl group. Examples of such groups include, but are not limited to, phenoxy, 4-chloro-3-ethylphenoxy, 4-chloro-3-methylphenoxy, 3-chloro-4-ethylphenoxy, 3,4-dichlorophenoxy, 4-methylphenoxy, 3-trifluoromethoxyphenoxy, 3-trifluoromethylphenoxy, 4-fluorophenoxy, 3,4-dimethylphenoxy, 5-bromo-2-fluorophenoxy, 4-bromo-3-fluorophenoxy, 4-fluoro-3-methylphenoxy, 5,6,7,8-tetrahydronaphthyloxy, 3-isopropylphenoxy, 3-cyclopropylphenoxy, 3-ethylphenoxy, 4-tert-butylphenoxy, 3-pentafluoroethylphenoxy, and 3-(1,1,2,2-tetrafluoroethoxy) phenoxy.

The term "alkoxy" refers to an oxy-containing group substituted with an alkyl or cycloalkyl group. Examples of an alkoxy group include, without limitation, methoxy, ethoxy, tert-butoxy, and cyclohexyloxy. "Lower alkoxy" groups have one to six carbon atoms, and include, but are not limited to, methoxy, ethoxy, propoxy, butoxy, isopropoxy, and tert-butoxy groups.

The term "aralkoxy" refers to an oxy-containing aralkyl group attached through an oxygen atom to other groups. "Lower aralkoxy" groups are phenyl groups attached to a lower alkoxy group. Examples of a lower aralkoxy group includes, but is not limited to, benzyloxy, 1-phenylethoxy, trifluoromethoxybenzyloxy, 3-trifluoromethylbenzyloxy, 3,5-difluorobenyloxy, 3-bromobenzyloxy, 4-propylbenzyloxy, 2-fluoro-3-trifluoromethylbenzyloxy, and 2-phenylethoxy.

The term "acyl" refers to a —C(=O)R moiety, wherein R is hydrogen, alkyl, alkenyl, alkynyl, carbocyclic, heterocylic, aryl, or aralkyl. Preferably, R is hydrogen, alkyl, aryl, or aralkyl.

The term "carboxyl" refers to a —R'C(=O)OR" moiety, wherein R and R" are independently hydrogen, alkyl, alkenyl, alkynyl, carbocyclic, heterocyclic, heterocyloalkyl, aryl, ether, or aralkyl. R' can additionally be a covalent bond. A "carboxyl" includes both carboxylic acids, and carboxylic acid esters.

The term "carboxylic acid" refers to a carboxyl group in which R' is hydrogen or a salt. Carboxylic acids include, but are not limited to, formic acid, acetic acid, propionic acid, butyric acid, valeric acid, 2-methyl propionic acid, oxiranecarboxylic acid, and cyclopropane carboxylic acid.

The term "carboxylic acid ester" or "ester" refers to a carboxyl group in which R' is alkyl, alkenyl, alkynyl, carbocyclic, heterocyclic, aryl, or aralkyl. Examples of carboxylic acids include, but are not limited to, formic acid, acetic acid, propionic acid, butanoic acid, pentanoic acid, hexanoic acid, heptanoic acid, octanoic acid, nonanoic acid, decanoic acid, cyclopropanecarboxylic acid, cyclobutanecarboxylic acid, cyclopentanecarboxylic acid, cyclohexanecarboxylic acid, cycloheptanecarboxylic acid, cyclooctanecarboxylic acid, or cyclononanecarboxylic acid.

The term "carbonyl" refers to refers to a C=O moiety, also known as an "oxo" group.

The term "heterocycle" or "heterocyclyl" or "heterocyclic ring" refers to an aromatic or non-aromatic cyclic hydrocarbon with 3 to 12 carbon atoms. In exemplary embodiments, "heterocyclyl" refers to a cyclic hydrocarbon containing 4, 5, or 6 ring atoms (i.e., $C_{4-6}$ heterocyclyl). The heterocycle may optionally be substituted, saturated, or unsaturated. Typically, at least one of the ring atoms is an Oxygen (O), Nitrogen (N), Sulfur (S), Phosphorous (P), or Selenium (Se). For example, in some embodiments, a ring N atom from the heterocyclyl is the bonding atom to a —C(O) moiety to form an amide, a carbamate, or a urea. Examples of a heterocyclic group include, but are not limited to, aziridine, oxirane, thiirane, azetidine, oxetane, thietane, pyrrolidine, imidazole, tetrahydrofuran, pyran, thiopyran, thiomorpholine, thiomorpholine S-oxide, oxazoline, tetrahydrothiophene, piperidine, tetrahydropyran, thiane, imidazolidine, oxodioxolenyl, oxazolidine, thiazolidine, dioxolane, dithiolane, piperazine, oxazine, dithiane, dioxane, pyridinyl, furanyl, benzofuranyl, isobenzofuranyl, pyrrolyl, thienyl, 1,2,3-triazolyl, 1,2,4-triazolyl, indolyl, imidazolyl, thiazolyl, thiadiazolyl, pyrimidinyl, oxazolyl, triazinyl, and tetrazolyl. Exemplary heterocycles include benzimidazole, dihydrothiophene, dioxin, dioxane, dioxolane, dithiane, dithiazine, dithiazole, dithiolane, furan, indole, 3-H indazole, 3-H-indole, indolizine, isoindole, isothiazole, isoxazole, morpholine, oxazole, oxadiazole, oxathiazole, oxathiazolidine, oxazine, oxadiazine, piperazine, piperidine, purine, pyran, pyrazine, pyrazole, pyridine, pyrimidine, pyrimidine, pyridazine, pyrrole, pyrrolidine, tetrahydrofuran, tetrazine, thiadiazine, thiadiazole, thiatriazole, thiazine, thiazole, thiophene, triazine, and triazole. The heterocycle may be optionally substituted with an amino, alkyl, alkenyl, alkynyl, halo, hydroxyl, carbocyclic, thio, other heterocyclic, or aryl group.

The term "heteroaryl" refers to a cyclic hydrocarbon, where at least one of a plurality of ring atoms is an O, N, S, P or Se. The ring of the heteroaryl is characterized by delocalized [pi] electrons (aromaticity) shared among the ring members. Heteroaryl moieties as defined herein may have Carbon (C), N, S, P or Se bonding hands. For example, in some embodiments, a ring N atom from the heteroaryl is the bonding atom to a —C(O) moiety to form an amide, a carbamate, or an urea. In exemplary embodiments, "heteroaryl" refers to a cyclic comprising 5 or 6 ring atoms (i.e., $C_{5-6}$ heteroaryl). Examples of a heteroaryl group include, but are not limited to, pyrrole, furan, thiene, oxazole, thiazole, isoxazole, isothiazole, imidazole, pyrazole, oxadiazole, thiadiazole, triazole, tetrazole, pyridine, pyrimidine, pyrazine, pyridazine, and triazine.

The term "hydroxy" or "hydroxyl" refers to the substituent —OH.

The term "oxo" refers to the substituent =O.

The term "nitro" refers to $NO_2$.

The term "azido" refers to $N_3$.

The term "sulfur analog(s)" refers to an analog of a compound, wherein one or more selenium atoms have been replaced by one or more sulfur atoms.

The term "sulfanyl" refers to a —SR moiety, where R is hydrogen, alkyl, alkenyl, alkynyl, carbocyclic, heterocylic, aryl, or aralkyl.

The term "sulfenyl" refers to a —SOR' moiety, where R' is hydrogen, alkyl, alkenyl, alkynyl, carbocyclic, heterocylic, aryl, or aralkyl.

The term "sulfonyl" refers to a —SOR' moiety, where R refers to hydrogen, alkyl, alkenyl, alkynyl, carbocyclic, heterocylic, aryl, or aralkyl.

The term "ketone" refers to a moiety containing at least one carbonyl group where the carbonyl carbon is bound to two other carbon atoms. In exemplary embodiments, a "ketone" refers to a carbonyl-containing moiety containing 3, 4, 5, 6, 7, 8, 9 or 10 carbon atoms (i.e., $C_{3-10}$ ketone). Examples of a ketone group include, but are not limited to, acetone, butanone, pentanone, hexanone, heptanone, octanone, nonanone, decanone, cyclobutanone, cyclopentanone, cyclohexanone, cycloheptanone, cyclooctanone, cyclononanone and cyclodecanone.

The term "amino" refers to a primary, secondary or tertiary group having the formula, —NR'R," wherein R and R" are independently hydrogen, acyl, alkyl, alkyenyl, alkynyl, aralkyl, aryl, carboxyl, cycloalkyl, heterocyclic, or another amino group (as in the case of hydrazide). R' and R," together with the nitrogen atom to which they are attached, form a ring having 4 to 8 atoms. Thus, the term "amino," includes unsubstituted, monosubstituted (e.g., monoalkylamino or monoarylamino), and disubstituted (e.g., dialkylamino or aralkylamino) amino groups Amino groups include a —$NH_2$ moiety, methylamino, ethylamino, dimethylamino, diethylamino, methyl-ethylamino, pyrrolidin-1-yl or piperidino, morpholino, etc. Other exemplary "amino" groups forming a ring include pyrrolyl, imidazolyl, pyrazolyl, isothiazolyl, isoxazolyl, pyridyl, pyrazinyl, pyrimidinyl, pyridazinyl, indolizinyl, imidazolyl, isoindolyl, indolyl, indazolyl, purinyl, quinolizinyl. The ring containing the amino group may be optionally substituted with another amino, alkyl, alkenyl, alkynyl, halo, or hydroxyl group.

The term "amine" refers to a primary, secondary or tertiary amino group of the formula —NRR," wherein R' and R" as used in this definition are independently hydrogen, acyl, alkyl, alkyenyl, alkynyl, aralkyl, aryl, carboxyl, cycloalkyl, heterocyclic, or other amino (in the case of hydrazide) or R' and R" together with the nitrogen atom to which they are attached, form a ring having 4-8 atoms. Thus, the term "amino", as used herein, includes unsubstituted, monosubstituted (e.g., monoalkylamino or monoarylamino), and disubstituted (e.g., dialkylamino or aralkylamino) amino groups. Amino groups include —$NH_2$, methylamino, ethylamino, dimethylamino, diethylamino, methyl-ethylamino, pyrrolidin-1-yl or piperidino, morpholino, etc. Other exemplary "amino" groups forming a ring, include, but are not limited to, pyrrolyl, imidazolyl, pyrazolyl, isothiazolyl, isoxazolyl, pyridyl, pyrazinyl, pyrimidinyl, pyridazinyl, indolizinyl, imidazolyl, isoindolyl, indolyl, indazolyl, purinyl, quinolizinyl. The ring containing the amino group may be optionally substituted with another amino, alkyl, alkenyl, alkynyl, halo, or hydroxyl group.

The term "alcohol" refers to "hydroxy," hydroxyl," or any substituent comprising the —OH moiety.

The term "amino alcohol" refers to a functional group containing both an alcohol and an amine group. "Amino alcohols" also refer to amino acids having a carbon bound to an alcohol in place of the carboxylic acid group. In exemplary embodiments, an "amino alcohol" comprises an amine bound to the carbon adjacent to the alcohol-bearing carbon. In exemplary embodiments, "amino alcohol" refers to an amine and an alcohol-containing moiety containing 1, 2, 3, 4, 5, 6, 7, 8, 9, 10, 11 or 12 carbon atoms (i.e., $C_{1-12}$ amino alcohol). Examples of amino alcohols include, but are not limited to, ethanolamine, heptaminol, isoetarine, norepinephrine, propanolamine, sphingosine, methanolamine, 2-amino-4-mercaptobutan-1-ol, 2-amino-4-(methylthio)butan-1-ol, cysteinol, phenylglycinol, prolinol, 2-amino-3-phenyl-1-propanol, 2-amino-1-propanol, cyclohexylglycinol, 4-hydroxy-prolinol, leucinol, tert-leucinol, phenylalaninol, a-phenylglycinol, 2-pyrrolidinemethanol, tyrosinol, valinol, serinol, 2-dimethylaminoethanol, histidinol, isoleucinol, leucinol, methioninol, 1-methyl-2-pyrrolidinemethanol, threoninol, tryptophanol, alaninol, argininol, glycinol, glutaminol, 4-amino-5-hydroxypentanamide, 4-amino-5-hydroxypentanoic acid, 3-amino-4-hydroxybutanoic acid, lysinol, 3-amino-4-hydroxybutanamide, and 4-hydroxy-prolinol.

The term "amino acid" refers to a group containing a carboxylic acid and an amine bound to the carbon atom immediately adjacent to the carboxylate group, and includes both natural and synthetic amino acids. Examples of amino acids include, but are not limited to, arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan. In some embodiments, the carboxyl is substituted with H, a salt, ester, alkyl, or aralkyl. The amino group may also be substituted with H, acyl, alkyl, alkenyl, alkynyl, carboxyl, cycloalkyl, aralkyl, or heterocyclyl.

The term "ether" refers to the —R'—O—R" moiety, wherein R and R" are independently hydrogen, alkyl, alkenyl, alkynyl, carbocyclic, heterocyclic, aryl, or aralkyl. R' can additionally be a covalent bond attached to a carbon.

The term "halogen" refers to a fluorine, chlorine, bromine or iodine atom.

The term "halide" refers to a functional group containing an atom bound to a fluorine, chlorine, bromine or iodine atom. Exemplary embodiments disclosed herein may include "alkyl halide," "alkenyl halide," "alkynyl halide," "cycloalkyl halide," "heterocyclyl halide," or "heteroaryl halide" groups. In exemplary embodiments, "alkyl halide" refers to a moiety containing a carbon-halogen bond containing 1, 2, 3, 4, 5, 6, 7, 8, 9 or 10 carbon atoms (i.e., $C_{1-10}$ alkyl halide). Examples of an alkyl halide group include, but are not limited to, fluoromethyl, fluoroethyl, chloromethyl, chloroethyl, bromomethyl, bromoethyl, iodomethyl and iodoethyl groups. Unless otherwise indicated, any carbon-containing group referred to herein can contain one or more carbon-halogen bonds. By way of non-limiting example, a $C_1$ alkyl group can be, but is not limited to, methyl, fluoromethyl, difluoromethyl, trifluoromethyl, chloromethyl, dichloromethyl, trichloromethyl, bromomethyl, dibromomethyl, tribromomethyl, iodomethyl, diiodomethyl, triiodomethyl, chlorofluoromethyl, dichlorofluoromethyl, and difluorochloromethyl.

In the compounds described herein, heteroatoms are capable of bearing multiple different valencies. By way of non-limiting example, S, Se and N can be neutral or hold a positive charge. In addition, O can be neutral or hold a positive or negative charge.

An embodiment of the present disclosure may comprise a compound according to Formula (I):

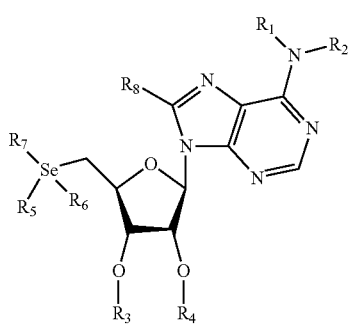

(I)

or a pharmaceutically acceptable salt, hydrate, or prodrug thereof. $R_1$ is H, acyl, alkyl, alkenyl, alkynyl, aralkyl, carboxyl, cycloalkyl, C(O)R', C(O)OR', wherein R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from oxygen or nitrogen.

$R_2$ is H, acyl, alkyl, alkenyl, alkynyl, aralkyl, carboxyl, cycloalkyl, C(O)R', C(O)OR', wherein R' is selected from alkyl, cycloalkyl, aryl, aralkyl, or heterocyclyl; or $R_1$ together with $R_2$ form a heterocyclic ring having 4 to 8 ring members with at least one heteroatom selected from oxygen or nitrogen.

$R_3$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least one heteroatom selected from oxygen or nitrogen.

$R_4$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least one heteroatom selected from oxygen or nitrogen.

$R_5$ is oxo, hydroxyl, alkyl, alkenyl, alkynyl, OR', or is absent; wherein R' is selected from alkyl, alkenyl, alkynyl, cycloalkyl, aryl, or aralkyl.

$R_6$ is oxo, hydroxyl, alkyl, alkenyl, alkynyl, OR', or is absent; wherein R' is selected from alkyl, alkenyl, alkynyl, cycloalkyl, aryl, or aralkyl.

$R_7$ is a $C_3$-$C_{16}$ alkyl, wherein the $C_3$-$C_{16}$ alkyl is not a substituted alkyl having both a carboxyl group and an amino group, alkenyl, alkynyl, ketone, amino alcohol, amino acid selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan, OR', Se—R', S—R', wherein R' for OR' is selected from the group consisting of H, alkyl, cycloalkyl, aryl, aralkyl, and heterocyclyl, wherein R' for Se—R' is selected from the group consisting of H, $C_3$-$C_{16}$ alkyl, cycloalkyl, aryl, aralkyl, and heterocyclyl, wherein R' for S—R' is selected from the group consisting of H, $C_3$-$C_{16}$ alkyl, cycloalkyl, aryl, aralkyl, and heterocyclyl; and $R_8$ is hydrogen, azido, alkyl, alkenyl, alkynyl.

Formula (I) may encompass diastereomers and enantiomers of the illustrative compounds. Enantiomers are defined as one of a pair of molecular entities which are mirror images of each other and non-superimposable. Diastereomers or diastereoisomers are defined as stereoisomers other than enantiomers. Diastereomers or diastereoisomers are stereoisomers not related as mirror images. Diastereoisomers are characterized by differences in physical properties.

The term "Compound C" refers to 5'-deoxy-5'-methylselenoadenosine, also known as (2R,4S,5 S)-2-(6-amino-9H-purin-9-yl)-5-((methylselanyl)methyl) tetrahydrofuran-3,4-diol (CAS Registry Number 5135-40-0), and includes any pharmaceutically acceptable salts thereof.

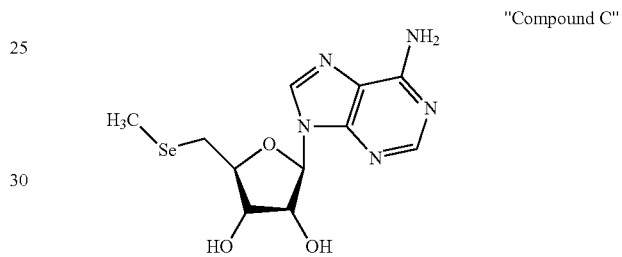

"Compound C"

The term "Compound D" refers to 5'-Selenoadenosyl homocysteine; (2R)-2-amino-4-((((2S,3S,5R)-5-(6-amino-9H-purin-9-yl)-3,4-dihydroxytetrahydrofuran-2-yl)methyl)selanyl)butanoic acid (CAS Registry Number 4053-91-2), and includes any pharmaceutically acceptable salts thereof.

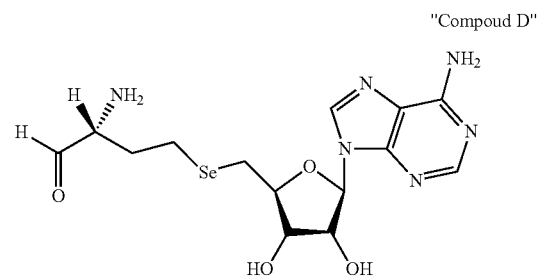

"Compound D"

The term "Compound E" refers to γ-L-glutamyl-Se-methyl-L-selenocysteine; also known as N5-(1-carboxy-2-(methylselanyl)ethyl)-L-glutamine, or any pharmaceutically acceptable salt thereof.

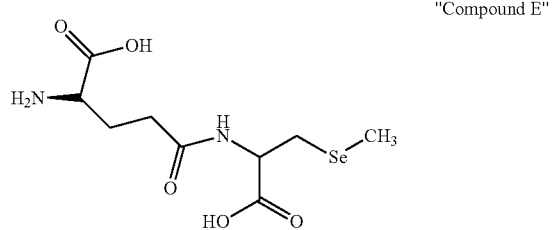

"Compound E"

The term "Compound H" refers to 5'-deoxy-5'-methylthioadenosine; 5'-S-Methyl-5'-thioadenosine (CAS Registry No. 2457-80-9), or a pharmaceutically acceptable salt thereof.

"Compound H"

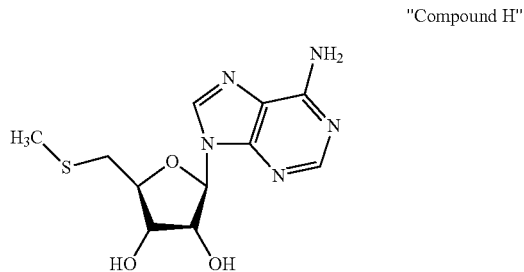

The term "Compound I" refers to S-Adenosyl-L-homocysteine, also known as (S)-5'-(S)-(3-Amino-3-carboxypropyl)-5'-thioadenosine (CAS Registry No. 979-92-0), or a pharmaceutically acceptable salt thereof.

"Compound I"

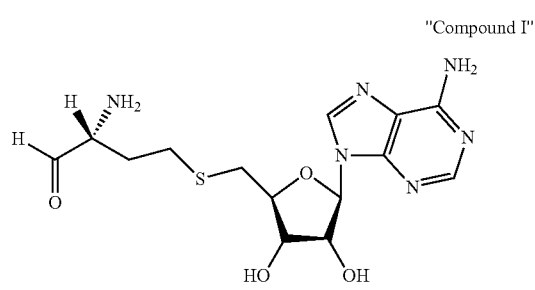

The term "Compound J" refers to γ-L-glutamyl-methyl-L-cysteine, also known as Gamma-glutamyl-methyl-cysteine, or a pharmaceutically acceptable salt thereof.

"Compound J"

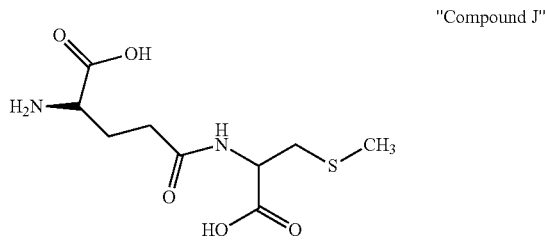

The term "Compound CDE" refers to a mixture of Compound C, Compound D and Compound E, or pharmaceutically acceptable salts thereof.

The term "Compound HIJ" refers to a mixture of Compound H, Compound I and Compound J, or pharmaceutically acceptable salts thereof.

The terms "analog" and "derivative" are interchangeable, and refer to a natural or non-natural modification of at least one position of a given molecule. For example, a derivative of a given compound or molecule may be modified either by addition of a functional group or atom, removal of a functional group or atom or change of a functional group or atom to a different functional group or atom (including, but not limited to, isotopes).

The term "comprising" refers to a composition, compound, formulation, or method that is inclusive and does not exclude additional elements or method steps. The term "comprising" also refers to a composition, compound, formulation, or method embodiments of the present disclosure that is inclusive and does not exclude additional elements or method steps.

The term "consisting of" refers to a compound, composition, formulation, or method that excludes the presence of any additional component or method steps. The term "consisting of" also refers to a compound, composition, formulation, or method of the present disclosure that excludes the presence of any additional component or method steps.

The term "consisting essentially of" refers to a composition, compound, formulation or method that is inclusive of additional elements or method steps that do not materially affect the characteristic(s) of the composition, compound, formulation or method. The term "consisting essentially of" also refers to a composition, compound, formulation or method of the present disclosure that is inclusive of additional elements or method steps that do not materially affect the characteristic(s) of the composition, compound, formulation or method.

The term "compound(s)" refers to any one or more chemical entity, moiety, pharmaceutical, drug, and the like that can be used to treat, diagnose, or prevent a disease, illness, sickness, or disorder of bodily function. A compound can be determined to be therapeutic by using the screening methods of the present application.

The term "composition(s)" refers to the combination of one or more compounds with or without another agent, such as but not limited to a carrier agent. (e.g., one or more selenium containing compounds with a carrier, inert or active, making the composition especially suitable for diagnostic or therapeutic use in vitro, in vivo, or ex vivo.

The term "component" refers to a constituent part of a compound or a composition. For example, components of a composition can include a compound, a carrier, and any other agent present in the composition.

The term "effective amount" refers to the amount of a composition or compound sufficient to effect beneficial or desired results. An effective amount can be administered in one or more applications or dosages and is not intended to be limited to a particular formulation or administration route.

The term "hydrate" refers to a compound which is associated with water in the molecular form (i.e., in which the H—OH bond is not split), and may be represented, for example, by the formula R×H$_2$O, where R is a compound disclosed herein. A given compound may form more than one hydrate including, for example, monohydrates (R×H$_2$O), dihydrates (R$_2$×H$_2$O), trihydrates (R$_3$×H$_2$O), and the like.

The term "inhibitory" or "antagonistic" refers to the property of a compound that decreases, limits, inhibits, or blocks the action or function of another compound.

The term "isolated" refers to the separation of a material from at least one other material in a mixture or from materials that are naturally associated with the material. For example, a compound synthesized synthetically is separated from a starting material or an intermediate.

A "known therapeutic compound" refers to a therapeutic compound that has been shown (e.g., through animal trials or prior experience with administration to humans) to be effective in a treatment. In other words, a known therapeutic compound is not limited to a compound known or shown to be efficacious in the treatment of disease (e.g., neurodegenerative disease).

The term "mitochondrial potential" refers to a voltage difference across the inner mitochondrial membrane maintained by the net movement of positive charges across the membrane.

The term "modulates" refers to a change in the state (e.g. activity or amount) of a compound from a known or determined state.

"Optional" or "optionally" refers to a circumstance in which the subsequently described event or circumstance may or may not occur, and that the description includes instances where said event or circumstance occurs and instances in which it does not. "Optionally" is inclusive of embodiments in which the described conditions is present and embodiments in which the described condition is not present. For example, "optionally substituted phenyl" means that the phenyl may or may not be substituted, and that the description includes both unsubstituted phenyl and phenyl wherein there is substitution.

The term "organic selenium" or "selenoorganic compound" refers to any organic compound wherein selenium replaces sulfur. Thus, organic selenium can refer to any such compound biosynthesized by yeast or to free organic selenocompounds that are chemically synthesized, such as free selenomethionine. The terms "patient" or "subject" are used interchangeably and refer to any member of Kingdom Animalia. A subject may be but not limited to a mammal, such as a human, domesticated mammal (e.g., dog or cat), or a livestock mammal (e.g., cow/cattle or pig/swine) or cells derived therefrom.

The term "ppb" as used herein refers to parts per billion and the term "ppm" as used herein refers to parts per million. Each of ppm and ppb is based on selenium for selenium-containing compounds or based on sulfur for sulfur-containing compounds, unless otherwise expressly stated herein. Examples of Selenium containing compounds are Compound C, Compound D, and Compound E. Examples of sulfur containing compounds are Compound H, Compound I, and Compound J. In order to convert ppb based on selenium to ppb of the compound containing selenium multiply the indicated ppb by the following factors: 4.35 for Compound C, 5.46 for Compound D, and 3.94 for Compound E. In order to convert ppb based on sulfur to ppb of the compound containing sulfur multiply the indicated ppb by the following factors: 9.28 for Compound H, 12.00 for Compound I, and 8.25 for Compound J.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "carrier" refers to a pharmaceutically acceptable carrier.

The phrase "pharmaceutically acceptable carrier" refers to a pharmaceutically acceptable material, composition or control, such as a liquid or solid filler, diluent, excipient, solvent or encapsulating material, involved in carrying or transporting a selenium-containing compound, analog, or derivative from one organ or portion of the body to another organ or portion of the body. A carrier must be acceptable in the sense of being compatible with the other ingredients of the formulation and not injurious to the patient or subject. Some examples of materials which may serve as pharmaceutically acceptable carriers include, but are not limited to: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleaste and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "prodrug" refers to a pharmacologically active compound. More typically, a "prodrug" refers to an inactive compound that is converted into a pharmacologically active agent by a metabolic transformation. A prodrug of a compound or composition described herein is prepared by modifying functional groups present in the compound of any of the formula above in such a way that the modifications may be cleaved in vivo to release the parent compound. A prodrug may readily undergoes in vivo chemical changes under physiological conditions (e.g., hydrolysis or enzyme catalysis) resulting in liberation of the pharmacologically active agent. Prodrugs include compounds of any of the formula described herein, wherein a hydroxy, amino, or carboxy group is bound to any group that may be cleaved in vivo to regenerate the free hydroxyl, amino or carboxy group, respectively. Examples of prodrugs include, but are not limited to, esters (e.g., acetate, formate, and benzoate derivatives) of compounds of any of the formula above or any other derivative, which upon being brought to the physiological pH or through enzyme action is converted to the active parent drug. Conventional procedures for the selection and preparation of suitable prodrug derivatives are described in the art (see, for example, Bundgaard. Design of Prodrugs. Elsevier, 1985).

The term "purified" or "substantially purified" refers to the removal of inactive or inhibitory components (e.g., contaminants) from a composition to the extent that 10% or less (e.g., 10% or less, 9% or less, 8% or less, 7% or less, 6% or less, 5% or less, 4% or less, 3% or less, 2% or less, or 1% or less) of the composition comprises inactive components, compounds, or pharmaceutically acceptable carriers.

The term "salts" can include pharmaceutically acceptable acid addition salts or addition salts of free bases. Examples of acids which may be employed to form pharmaceutically acceptable acid addition salts include, but are not limited to, salts derived from nontoxic inorganic acids such as nitric, phosphoric, sulfuric, or hydrobromic, hydroiodic, hydrofluoric, phosphorous, as well as salts derived from nontoxic organic acids such as aliphatic mono- and dicarboxylic acids, phenyl-substituted alkanoic acids, hydroxyl alkanoic acids, alkanedioic acids, aromatic acids, aliphatic and aromatic sulfonic acids, and acetic, maleic, succinic, or citric acids. Non-limiting examples of such salts include napadisylate, besylate, sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleaste, mandelate, benzoate, chlorobenzoate, methylbenzoate, dinitrobenzoate, phthalate, benzenesulfonate, toluenesulfonate, phenylacetate, citrate, lactate, maleaste, tartrate, methanesulfonate, and the like.

Also contemplated are salts of amino acids, such as, but not limited to arginate, gluconate, galacturonate, and other salts, such as, but not limited to those disclosed in Berge, et al. ("Pharmaceutical Salts", J. Pharma. Sci. 1977; 66:1-19).

The term "pharmaceutically acceptable salts" include, but is not limited to, salts well known to those skilled in the art. For example, mono-salts (e.g., alkali metal and ammonium salts) and poly-salts (e.g., di-salts or tri-salts) of the present invention. Pharmaceutically acceptable salts of compounds of the disclosure are prepared, for example, when an exchangeable group, such as hydrogen in the —OH, —NH—, or —P(=O)(OH)— moieties, is replaced with a pharmaceutically acceptable cation (e.g., a sodium, potassium, or ammonium ion) and can conveniently be prepared from a corresponding compound disclosed herein by, for example, reaction with a suitable base.

In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts. Pharmaceutically acceptable salts may be obtained using standard procedures well known in the art, for example, by reacting a sufficiently basic compound, such as an amine with a suitable acid affording a physiologically acceptable anion. Alkali metal salts (e.g., sodium, potassium or lithium) or alkaline earth metal salts (e.g., calcium) of carboxylic acids can also be made.

The terms "selenium-enriched yeast" and "selenized yeast" refer to any yeast (e.g., *Saccharomyces cerevisiae*) that is cultivated in a medium containing a selenium source, such as inorganic selenium salts. The amount of residual inorganic selenium salt in the finished product is generally quite low (e.g., less than 2%).

The term "substituted" in connection with a moiety refers to a further substituent which is attached at any acceptable location on the moiety. Unless otherwise indicated, moieties can bond through a carbon, nitrogen, oxygen, sulfur, or any other acceptable atom. Examples of substituents include, but are not limited to amines, alcohols, thiols, ethers, alkenes, alkynes, epoxides, aziridines, oxiranes, azetidines, dihydrofurans, pyrrolidines, pyrans, piperidines, aldehydes, ketones, esters, carboxylic acids, carboxylates, imines, imides, azides, azo groups, eneamines, alkyl halides, alkenyl halides, alkynyl halides, aryl halides, phosphines, phosphine oxides, phophinites, phosphonites, phosphites, phohsphonates, phosphates, sulfates, sulfoxides, sulfonyl groups, sulfoxyl groups, sulfonates, nitrates, nitrites, nitriles, nitro groups, nitroso groups, cyanates, thiocyanates, isothiocyanates, carbonates, acyl halides, peroxides, hydroperoxides, hemiacetals, hemiketals, acetals, ketals, orthoesters, orthocarbonate esters, sulfides, disulfides, sulfonic acids, sulfonic acids, thiones, thials, phosphodiesters, boronic acids, boronic esters, boronic acids and boronic esters.

The terms "treating," "treat," or "treatment" refer to a therapeutic treatment where the object is to slow down (e.g., lessen or postpone) the onset of an undesired physiological condition, to reduce symptoms of a present disorder or disease, or to obtain beneficial or desired results, such as partial or total restoration or inhibition in decline of a parameter, value, function, metric, or result that had or would become abnormal. Beneficial or desired results include, but are not limited to, alleviation of symptoms; diminishment of the extent or vigor or rate of development of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether or not it translates to immediate lessening of actual clinical symptoms, or enhancement or improvement of the condition, disorder or disease.

The term "reagent(s) capable of specifically detecting gene expression" refers to reagents capable of or sufficient to detect the expression of various genes described herein. Examples of suitable reagents include, but are not limited to, nucleic acid primers or probes capable of specifically hybridizing to mRNA or cDNA and antibodies (e.g., monoclonal or polyclonal antibodies).

The term "toxic" refers to any detrimental or harmful effects on a subject, a cell, or a tissue as compared to the same cell or tissue prior to the administration of the toxicant.

Compounds and Compositions

The present disclosure is directed to selenoorganic compounds, compositions, and methods of using the compounds and compositions. The compounds and compositions disclosed herein may inhibit β amyloid aggregation, inhibit ApoE4 expression, inhibit p38 or Tau protein phosphorylation or increase Neprilysin expression. However, the compositions, compounds and methods of the present disclosure do not adversely affect glucose metabolism in liver cells or notch signaling molecules. The compounds and compositions disclosed herein may also be used to treat or prevent Alzheimer's Disease.

One embodiment of the present disclosure is directed to a composition comprising, consisting essentially of, or consisting of a compound of Formula (I):

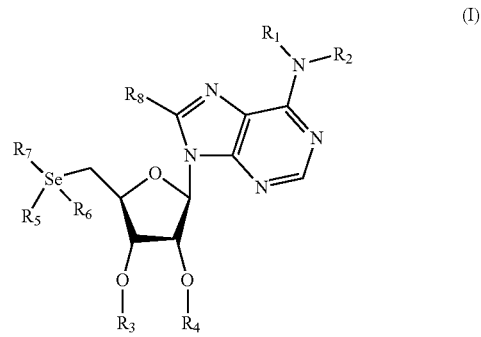

or a pharmaceutically acceptable salt, hydrate, or prodrug thereof.

$R_1$ is H, acyl, alkyl, alkenyl, alkynyl, aralkyl, carboxyl, cycloalkyl, C(O)R', C(O)OR', where R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from oxygen or nitrogen.

$R_2$ is H, acyl, alkyl, alkenyl, alkynyl, aralkyl, carboxyl, cycloalkyl, C(O)R', C(O)OR', where R' is selected from alkyl, cycloalkyl, aryl, aralkyl, or heterocyclyl; or $R_1$ together with $R_2$ form a heterocyclic ring having 4 to 8 ring members with at least one heteroatom selected from oxygen or nitrogen.

$R_3$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least one heteroatom selected from oxygen or nitrogen.

$R_4$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least one heteroatom selected from oxygen or nitrogen.

$R_5$ is oxo, hydroxyl, alkyl, alkenyl, alkynyl, OR', or is absent; where R' is selected from alkyl, alkenyl, alkynyl, cycloalkyl, aryl, or aralkyl.

$R_6$ is oxo, hydroxyl, alkyl, alkenyl, alkynyl, OR', or is absent; where R' is selected from alkyl, alkenyl, alkynyl, cycloalkyl, aryl, or aralkyl.

$R_7$ is a $C_3$-$C_{16}$ alkyl, wherein the $C_3$-$C_{16}$ alkyl is not a substituted alkyl having both a carboxyl group and an amino group, alkenyl, alkynyl, ketone, amino alcohol, amino acid selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan, OR', Se—R', S—R', where R' for OR' is selected from the group consisting of H, alkyl, cycloalkyl, aryl, aralkyl, and heterocyclyl, where R' for Se—R' is selected from the group consisting of H, $C_3$-$C_{16}$ alkyl, cycloalkyl, aryl, aralkyl, and heterocyclyl, where R' for S—R' is selected from the group consisting of H, $C_3$-$C_{16}$ alkyl, cycloalkyl, aryl, aralkyl, and heterocyclyl; and $R_8$ is hydrogen, azido, alkyl, alkenyl, alkynyl.

Another aspect of the present application provides analogs or derivatives of the biologically active selenium-containing compounds described herein (e.g., Formula (I)). Analogs and/or derivatives of the selenium-containing compounds can be prepared synthetically. For example, one embodiment Formula (I) comprises any analog, derivative or pharmaceutically acceptable salts thereof. Another embodiment of the present composition comprises a compound of Formula (I) and combinations thereof.

An additional embodiment of the compound of Formula (I) may comprise, consist essentially of, or consist of 5'-deoxy-5'-methylselenoadenosine ("Compound C"), and includes any analogs, derivatives, and/or pharmaceutically acceptable salts thereof. Another embodiment of Compound C may comprise (2R,4S,5S)-2-(6-amino-9H-purin-9-yl)-5-((methylselanyl)methyl)tetrahydrofuran-3,4-diol (CAS Registry Number 5135-40-0), and includes any analogs, derivatives, and/or pharmaceutically acceptable salts thereof.

"Compound C"

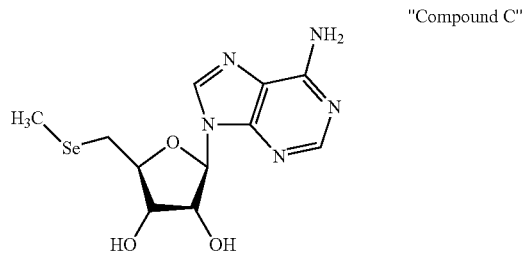

A composition of the present disclosure may comprise, consist essentially of, or consist of a compound of Formula (I), Compound C, and combinations thereof. For example, one aspect of the present application provides compositions comprising a compound selected from the group consisting of 5'-deoxy-5'-methylselenoadenosine, a compound of Formula (I), and combinations thereof. In further embodiments, one or more of these compounds can be synthetic, isolated, and/or purified.

In some embodiments, the composition comprises, consists essentially of, or consists of at least 5'-deoxy-5'-methylselenoadenosine, and one other compound. In other embodiments, the other compound is a selenium-containing compound. In further embodiments, the composition comprises a ratio of 5'-deoxy-5'-methylselenoadenosine to the other compound (e.g., a selenium-containing compound) of at least 1:1 to 100:1, 1:1 to 50:1, 1:1 to 10:1, 1:1 to 6:1, or 1:1 to 3:1.

Another embodiment of the composition of the present invention comprises, consists essentially of, or consists of 5'-Selenoadenosyl homocysteine ("Compound D"), and includes any analogs, derivatives, and/or pharmaceutically acceptable salts thereof. Another embodiment of Compound D may comprise (2R)-2-amino-4-((((2S,3S,5R)-5-(6-amino-9H-purin-9-yl)-3,4-dihydroxytetrahydrofuran-2-yl)methyl)selanyl)butanoic acid (CAS Registry Number 4053-91-2), and includes any analogs, derivatives, and/or pharmaceutically acceptable salts thereof.

"Compoud D"

A further embodiment of the composition of the present invention comprises, consists essentially of, or consists of γ-L-glutamyl-Se-methyl-L-selenocysteine ("Compound E"), and includes any analogs, derivatives, and/or pharmaceutically acceptable salts thereof. Another embodiment of Compound E may comprise N5-(1-carboxy-2-(methylselanyl)ethyl)-L-glutamine, and includes any analogs, derivatives, and/or pharmaceutically acceptable salts thereof.

"Compound E"

Additional embodiments of the composition of the present disclosure may comprise, consist essentially of, or consist of mixtures of the compounds described herein. For example, one embodiment of the present composition is "Compound CDE." Compound CDE comprises a mixture of Compound C, Compound D and Compound E, any analogs, derivatives, and/or pharmaceutically acceptable salts thereof. Compound mixtures are not limited to those described herein, and comprise any combination or mixture of Compounds C, D, or E, and combinations thereof.

In some embodiments, a composition comprises, consists essentially of, or consists of at least about 0.033% (w/v) to at least about 0.1% (w/v) of one of the compounds. For example, a composition may comprise at least 0.033% (w/v), at least 0.035% (w/v), at least 0.040% (w/v), at least 0.045% (w/v), at least 0.050% (w/v), at least 0.055% (w/v), at least 0.060% (w/v), at least 0.065% (w/v), at least 0.070% (w/v), at least 0.075% (w/v), at least 0.080% (w/v), at least 0.085% (w/v), at least 0.090% (w/v), at least 0.095% (w/v), at least 0.1% (w/v), at least about 0.033% (w/v), at least about 0.1% (w/v), or about 0.033% (w/v) to about at least 0.1% (w/v) of 5'-deoxy-5'-methylselenoadenosine, a compound according to Formula (I), and/or mixtures thereof and all percent range values in between these ranges.

In other embodiments, the composition comprises about 0.033% (w/v) to about 99.9% (w/v), about 0.033% to about 90% (w/v), about 0.033% to about 80% (w/v), about 0.033% to about 70% (w/v), about 0.033% to about 60% (w/v), about 0.033% to about 50% (w/v), about 0.033% to about 40% (w/v), about 0.033% to about 30% (w/v), about 0.033% to about 20% (w/v), about 0.033% to about 10% (w/v), about 0.033% to about 5% (w/v), or about 0.033% to about 1% (w/v) of 5'-deoxy-5'-methylselenoadenosine, one compound according to Formula (I), and/or mixtures thereof, and all percent range values in between.

In further embodiments, the composition comprises about 0.1% (w/v) to about 99.9% (w/v), about 0.1% to about 90% (w/v), about 0.1% to about 80% (w/v), about 0.1% to about 70% (w/v), about 0.1% to about 60% (w/v), about 0.1% to about 50% (w/v), about 0.1% to about 40% (w/v), about 0.1% to about 30% (w/v), about 0.1% to about 20% (w/v), about 0.1% to about 10% (w/v), about 0.1% to about 5% (w/v), or about 0.1% to about 1% (w/v) of 5'-deoxy-5'-methylselenoadenosine, one compound according to Formula (I), and/or mixtures thereof, and all percent range values in between 0.1% (w/v) to 99.9 (w/v).

In other embodiments, a composition comprises at least about 0.033% (w/v) to at least about 0.1% (w/v) of all of the compounds or a mixture of the compounds of 5'-deoxy-5'-methylselenoadenosine and one or more compounds according to Formula (I) and all percent range values in between 0.033% (w/v) and 0.1% (w/v).

In other embodiments, compositions may exclude one or more of 5'-deoxy-5'-methylthioadenosine ("Compound H"), S-Adenosyl-L-homocysteine ("Compound I"), Gamma-glutamyl-methyl-cysteine ("Compound J"), Gamma-L-glutamyl-Se-methyl-L-selenocysteine, Se-adenosylhomocysteine, or glutamyl selenocysteine, because one or more of these compounds may be unnecessary to the composition or inhibitory to other compounds in the composition.

In some embodiments, a composition is provided comprising, consisting essentially of, or consisting of a compound according to Formula (I), or a pharmaceutically acceptable salt, hydrate, or prodrug thereof, wherein $R_1$, $R_3$, $R_4$ and $R_8$ are each H; $R_2$ is H, acyl, alkyl, alkenyl, alkynyl, aralkyl, carboxyl, cycloalkyl, C(O)R', or C(O)OR', where R' is selected from alkyl, cycloalkyl, aryl, aralkyl, or heterocyclyl; $R_5$ and $R_6$ are each absent; and $R_7$ is a $C_3$-$C_{16}$ alkyl, wherein the $C_3$-$C_{16}$ alkyl is not a substituted alkyl having both a carboxyl group and an amino group, alkenyl, alkynyl, ketone, amino alcohol, amino acid selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan, OR', Se—R', S—R', where R' for OR' is selected from the group consisting of H, alkyl, cycloalkyl, aryl, aralkyl, and heterocyclyl, where R' for Se—R' is selected from the group consisting of H, $C_3$-$C_{16}$ alkyl, cycloalkyl, aryl, aralkyl, and heterocyclyl, where R' for S—R' is selected from the group consisting of H, $C_3$-$C_{16}$ alkyl, cycloalkyl, aryl, aralkyl, and heterocyclyl.

In a specific embodiment, a composition is provided comprising, consisting essentially of, or consisting of at least about 0.033% (w/v) to at least about 0.1% (w/v) of a compound, or a pharmaceutically acceptable salt, hydrate, or prodrug thereof, according to Formula (I) that is 5'-deoxy-5'-methylselenoadenosine ("Compound C"). In another embodiment, the composition excludes 5'-Selenoadenosyl homocysteine and/or Gamma-L-glutamyl-Se-methyl-L-selenocysteine. In yet further embodiments, the composition excludes one or more of 5'-deoxy-5'-methylthioadenosine, S-Adenosyl-L-homocysteine, and Gamma-glutamyl-methyl-cysteine.

In some embodiments, a composition is provided comprising, consisting essentially of, or consisting of a compound according to Formula (I), 5'-deoxy-5'-methylselenoadenosine ("Compound C"), or a pharmaceutically acceptable salt, hydrate, or prodrug thereof, wherein $R_1$, $R_3$, $R_4$ and $R_8$ are each H; $R_2$ is H, acyl, alkyl, alkenyl, alkynyl, aralkyl, carboxyl, cycloalkyl, C(O)R', C(O)OR', where R' is selected from alkyl, cycloalkyl, aryl, aralkyl, or heterocyclyl; $R_5$ and $R_6$ are each absent; and $R_7$ is alkyl or amino acid; with the proviso that 5'-selenoadenosyl methionine, dehydroxy 5'-deoxy-5'-methylselenoadenosine, ethylselenoadenosine, seleno(hydroxyl)-selenophene-(3'-deoxy-adenosine), allylselenoadenosyl homocysteine, seleno-adenosyl homocysteine, seleno-hydroxy adenosyl homocysteine, seleno adenosine, seleno-adenosyl-Se(methyl)-selenoxide, adenosyl-hydroxy selenoxide, ethyl selenoadenosine, seleno-(hydroxy)-selenophene-(3'-desoxy-adenosine), adenosyl-hydroxy selenoxide, and seleno-adenosyl-Se (methyl)-selenoxide may each be excluded from the composition.

In some embodiments of the present disclosure, a composition is provided comprising, consisting essentially of, or consisting of a compound according to Formula (I), or a pharmaceutically acceptable salt, hydrate, or prodrug thereof, $R_1$ is H, acyl, alkyl, alkenyl, alkynyl, aralkyl, carboxyl, cycloalkyl, C(O)R', C(O)OR', where R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from oxygen or nitrogen; $R_2$ is H, acyl, alkyl, alkenyl, alkynyl, aralkyl, carboxyl, cycloalkyl, C(O)R', C(O)OR', where R' is selected from alkyl, cycloalkyl, aryl, aralkyl, or heterocyclyl; or $R_1$ together with $R_2$ form a heterocyclic ring having 4 to 8 ring members with at least one heteroatom selected from oxygen or nitrogen; $R_3$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least one heteroatom selected from oxygen or nitrogen; $R_4$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least one heteroatom selected from oxygen or nitrogen; $R_5$ is oxo, hydroxyl, alkyl, alkenyl, alkynyl, OR', or is absent; where R' is selected from alkyl, alkenyl, alkynyl, cycloalkyl, aryl, or aralkyl; $R_6$ is oxo, hydroxyl, alkyl, alkenyl, alkynyl, OR', or is absent; where R' is selected from alkyl, alkenyl, alkynyl, cycloalkyl, aryl, or aralkyl; $R_7$ is an alkyl selected from the group consisting of iso-propyl, butyl, iso-butyl, secondary-butyl, tertiary-butyl, pentyl, iso-pentyl, neo-pentyl, hexyl, iso-hexyl, 3-methylpentyl, 2,3-dimethylbutyl, neo-hexyl, heptyl, octyl, nonyl, decyl, undecyl, dodecyl, tridecyl, tetradecyl, pentadecyl, and hexadecyl, alkenyl, alkynyl, ketone, amino alcohol, an amino acid selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan, OR', Se—R', where R' is selected from an alkyl selected from the group consisting of iso-propyl, butyl, iso-butyl, secondary-butyl, tertiary-butyl, pentyl, iso-pentyl, neo-pentyl, hexyl, iso-hexyl, 3-methylpentyl, 2,3-dimethylbutyl, neo-hexyl, heptyl, octyl, nonyl, decyl, undecyl, dodecyl, tridecyl, tetradecyl, pentadecyl, and hexadecyl, cycloalkyl, aryl, aralkyl, or heterocyclyl; and $R_8$ is hydrogen, azido, alkyl, alkenyl.

In some embodiments, compositions of the present disclosure comprises, consists of, or consists essentially of a compound according to Formula (I), 5'-deoxy-5'-methylselenoadenosine ("Compound C"), or a pharmaceutically acceptable salt, hydrate, or prodrug thereof, with the proviso that 5'-selenoadenosyl methionine, dehydroxy 5'-deoxy-5'-methylselenoadenosine, ethylselenoadenosine, seleno(hydroxyl)-selenophene-(3'-deoxy-adenosine), allylselenoadenosyl homocysteine, seleno-adenosyl homocysteine, seleno-hydroxy adenosyl homocysteine, seleno adenosine, seleno-adenosyl-Se(methyl)-selenoxide, adenosyl-hydroxy selenoxide, ethyl selenoadenosine, seleno-(hydroxy)-selenophene-(3'-desoxy-adenosine), adenosyl-hydroxy selnoxide, and seleno-adenosyl-Se(methyl)-selenoxide may each be excluded from the composition.

In other embodiments, a composition is provided comprising, consisting essentially of, or consisting of one or more compounds according to one or more of formulas (I), or 5'-deoxy-5'-methylselenoadenosine ("Compound C"), wherein each of the following compounds is excluded from the composition in order to minimize selenium toxicity, remove inactive or inhibitory compounds, and/or maximize the therapeutic index of the composition, wherein the excluded compounds are γ-glutamoyl selenocysteine-γ-glutamoyl cysteine, γ-glutamoylcysteine-2,3-DHP-selenocysteine, di-γ-glutamoylselenocysteine, selenoglutathione-γ-glutamoylcysteine, γ-glutamoyl selenocysteine-γ-glutamoyl cysteine, γ-glutamoylcysteine-2,3-DHP-selenocysteine, di-γ-glutamoylselenocysteine, selenoglutathione-γ-glutamoylcysteine, dehydroxy 5'-deoxy-5'-methylselenoadenosine, ethylselenoadenosine, seleno(hydroxyl)-selenophene-(3'-deoxy-adenosine), allylselenoadenosyl homocysteine, seleno-adenosyl homocysteine, seleno-hydroxy adenosyl homocysteine, seleno adenosine, seleno-adenosyl-Se(methyl)-selenoxide, adenosyl-hydroxy selenoxide, ethyl selenoadenosine, seleno-(hydroxy)-selenophene-(3'-desoxy-adenosine), adenosyl-hydroxy selenoxide, and seleno-adenosyl-Se(methyl)-selenoxide.

In some embodiments, any of the compounds described herein can be modified with a prodrug to prolong half-life. Prodrugs may also be helpful to protect the compound against oxidation, to target the compound to a tissue, or to allow the compound to pass the blood brain barrier.

In some embodiments, a prodrug comprises a selenoglycoside. Glycosides include monosaccharides, disaccharides, and oligosaccharides. Saccharides can include ribose, glucose, galactose, or mannose.

In other embodiments, a prodrug comprises a selenazolidine. These compounds provide for slow release of the compound. In yet a further embodiment, a prodrug comprises conjugation of a selenoorganic compound to a vitamin, such as Vitamin C or Vitamin E. These prodrug conjugates have improved protective effects. In yet other embodiments, a prodrug may be a cytochrome P450 activated prodrug, such as cyclic phosphates or phosphonates. Other embodiments of cytochrome P450 activated prodrugs improve bioavailability.

In some embodiments, any of the compounds of the present disclosure, including Formula (I), or 5'-deoxy-5'-methylselenoadenosine ("Compound C") can be modified to reduce oxidation of selenium. In other embodiments, the compounds can form a dimer through linkage between selenium atoms.

In some embodiments, any of the compounds of Formula (I) or 5'-deoxy-5'-methylselenoadenosine ("Compound C") can be modified by linkage to a tissue targeting agent or other agent for increasing half-life of the compound. Tissue targeting agents may include any agent known in the art, including, but not limited to, antibodies specific for binding to a tissue specific antigen, a transferrin receptor, or a prodrug.

In some embodiments, a composition of the disclosure is formulated to cross the blood brain barrier. The compositions of the invention can be combined with an implant material suitable for delivery to the brain, such as a polymeric biodegradable implant or carrier. Such polymeric carriers include, but are not limited to, polyethylene glycol, poly lactides, polyglycolides, polyorthoesters, polyvinyl pyrrolidone, and poly vinyl alcohols, and ethylene-co-vinyl acetate.

In other embodiments, the compounds can be linked to or combined with a nanoparticle carrier to deliver compositions to the brain and to provide for other tissue targeting. Other nanoparticles include phospholipids, chitosan, lactic acid, and dextran.

Microspheres and liposomes are additional carriers that may be used in the present disclosure. For example, microspheres and liposomes may include, but are not limited to, poly(lactic-co-glycolic) acid or PLGA carriers. In other embodiments, carrier delivery of compositions to the brain or other body tissues can be targeted by using liposomes or microspheres comprising an antibody, a transferrin receptor, or a prodrug as a targeting agent. Tissue targeting may also involve receptor mediated transport, such as with the insulin receptor or the transferrin receptor. These receptors can be integrated into liposomes or microspheres that also include the compositions as described herein.

Lipid prodrugs are also suitable for use with the compounds of the invention. By non-limiting example, certain lipid prodrugs are described in Hostetler et al., (1997 Biochem. Pharm. 53:1815-1822), and Hostetler et al., 1996 Antiviral Research 31:59-67), both of which are incorporated in their entirety herein by reference. Additional examples of suitable prodrug technology is described in WO 90/00555; WO 96/39831; WO 03/095665A2; U.S. Pat. Nos. 5,411,947; 5,463,092; 6,312,662; 6,716,825; and U.S. Published Patent Application Nos. 2003/0229225 and 2003/0225277 each of which is incorporated in their entirety herein by reference.

Such prodrugs may also possess the ability to target the drug compound to a particular tissue within the patient, e.g., liver, as described by Erion et al., (2004 J. Am. Chem. Soc. 126:5154-5163; Erion et al., Am. Soc. Pharm. & Exper. Ther. DOI:10.1124/jept.104.75903 (2004); WO 01/18013 A1; U.S. Pat. No. 6,752,981), each of which is incorporated in their entirety herein by reference. By way of non-limiting example, other prodrugs suitable for use with the compounds of the invention are described in WO 03/090690;

U.S. Pat. No. 6,903,081; U.S. Patent Application No. 2005/0171060A1; U.S. Patent Application No. 2002/0004594A1; and by Harris et al., (2002 Antiviral Chem & Chemo. 12: 293-300; Knaggs et al., 2000 Bioorganic & Med. Chem. Letters 10: 2075-2078) each of which is incorporated in their entirety herein by reference.

According to another aspect of the present invention, a pharmaceutical composition comprises a therapeutically-effective amount of one or more compounds of the present invention or a pharmaceutically acceptable salt, ester or prodrug thereof, together with a pharmaceutically acceptable diluent or carrier. Exemplary diluents and carriers of the present invention are described in detail in the Definitions section of this application. For example, in some embodiments, carriers can include water, physiological saline, and aqueous buffered solutions containing surfactants or stabilizing amino acids, such as histidine or glycine. In one embodiment of the present application, the pharmaceutically acceptable carrier is pharmaceutically inert.

In some embodiments of the present application, compositions and/or formulations comprising selenium can be administered to a subject alone, or in combination with other forms of selenium, drugs, small molecules, or in pharmaceutical compositions where it is mixed with excipient(s) or other pharmaceutically acceptable carriers. In other embodiments, compositions of the present application can be formulated using pharmaceutically acceptable carriers well known in the art in dosages suitable for oral administration. The carriers may enable the pharmaceutical compositions to be formulated as tablets, pills, capsules, liquids, gels, syrups, slurries, suspensions and the like, or for oral or nasal ingestion by a patient to be treated. In addition, compositions comprising one or more compounds including 5'-deoxy-5'-methylselenoadenosine, a compound of Formula (I), and combinations thereof can be administered to a subject (e.g., a patient) intravenously in a pharmaceutically acceptable carrier, such as physiological saline.

As is well known in the medical arts, dosages for any one subject may depend upon many factors, including the patient's size, body surface area, age, the particular compound to be administered, sex, time and route of administration, general health, and interaction with other drugs being concurrently administered. Depending on the target sought to be altered by treatment, pharmaceutical compositions may be formulated and administered systemically or locally.

Techniques known in the art for formulation and administration of therapeutic compounds are sufficient to administer the compounds and compositions of the present invention. The compositions of the present disclosure may be formulated for any route of administration, in particular for oral, rectal, transdermal, subcutaneous, intravenous, intramuscular or intranasal administration. Suitable routes of administration may, for example, include oral or transmucosal administration; as well as parenteral delivery, including intramuscular, subcutaneous, intramedullary, intrathecal, intraventricular, intravenous, intraperitoneal, or intranasal administration.

For injection, a composition of the present application (e.g., a selenium-containing composition) may be formulated in aqueous solutions, such as in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

The compositions may also be formulated in any conventional form, for example, as tablets, capsules, caplets, solutions, suspensions, dispersions, syrups, sprays, gels, suppositories, patches and emulsions. Compositions of the present application, particularly compositions comprising 5'-deoxy-5'-methylselenoadenosine, a compound of Formula (I), and combinations thereof, may also be added to nutritional drinks or food products (e.g., ENSURE, POWERBAR, or the like), a multi-vitamin, nutritional products, etc. to aid daily consumption.

Pharmaceutical compositions suitable for use in the present application include compositions wherein the active ingredients (e.g., 5'-deoxy-5'-methylselenoadenosine, a compound of Formula (I), and combinations thereof) are contained in an effective amount to achieve the intended purpose. For example, in a preferred embodiment, an effective amount of a pharmaceutical composition comprises an amount of a compound selected from the group consisting of 5'-deoxy-5'-methylselenoadenosine, a compound of Formula (I), and combinations thereof. Determination of effective amounts is well within the capability of those skilled in the art in light of the disclosure provided herein.

In some embodiments, pharmaceutical formulations can contain a disintegrant, gelatinized starch, and a coating. In other embodiments, disintegrants include crosslinked polyvinyl pyrrolidone, gums, starches including gelatinized starch, and cellulose products. In further embodiments, coatings include polyvinyl alcohol, cellulose derivatives, and methacrylic acid derivative.

Methods of Using Compounds and Compositions

Compounds and compositions of the present disclosure exhibit tissue specificity regarding gene expression of genes relating to biological processes and transcriptional activation/inactivation. For example, the present application relates to methods of using the compounds and compositions described herein to inhibit β amyloid aggregation, APOE4 expression, p38 or Tau protein phosphorylation, decrease BACE expression, decrease RCAN or to increase Neprilysin or Insulin Degrading Enzyme (IDE) expression. Additionally, the selenium-containing compounds and compositions of the present disclosure affect the gene expression of genes involved in biological processes, such as brain function, development, or signaling, insulin metabolism, and plaque or tangle formation. Thus, compositions and compounds may be administered alone or in combinations to an individual subject to, at risk of, or suffering from a disease or condition associated with aberration of the genes described herein. For example, the methods of the present application may find use in diagnosing or treating (e.g., prophylactically or therapeutically) a subject with a condition associated with Alzheimer's Disease.

In one embodiment of the present disclosure, a method or use for inhibiting β amyloid aggregation in a subject comprises administering an effective amount of a composition to the subject, the composition comprising at least about 0.033% (w/v) to about 0.1% (w/v) of a compound selected from the group consisting of 5'-deoxy-5'-methylselenoadenosine, a compound of Formula (I), and combinations thereof. In another embodiment, an effective amount of the composition inhibits β amyloid aggregation in neuronal cells as compared to neuronal cells not treated with the composition.

In another embodiment, a method or use for inhibiting APOE4, RCAN1, BACE and/or p38 expression in a subject comprises administering a composition to the subject, the composition comprising at least about 0.033% (w/v) to about 0.1% (w/v) of a compound selected from the group consisting of 5'-deoxy-5'-methylselenoadenosine, a compound of Formula (I), and combinations thereof. In some embodiment, an effective amount of the composition inhibits APOE4, RCAN1, BACE, and/or p38 expression in neuronal cells as compared to neuronal cells not treated with the composition.

In a further embodiment, a method or use for increasing Neprilysin or IDE expression in a subject comprises administering a composition to the subject, the composition comprising at least about 0.033% (w/v) to at least about 0.1% (w/v) of a compound selected from the group consisting of 5'-deoxy-5'-methylselenoadenosine, a compound of Formula (I), and combinations thereof. In a further embodiment, an effective amount of the composition increases Neprilysin and/or IDE expression in neuronal cells as compared to neuronal cells not treated with the composition.

In yet another embodiment, a method or use for decreasing expression of PSEN1 and/or NICASTRIN in a subject comprises administering a composition to the subject, the composition comprising at least about 0.033% (w/v) to at least about 0.1% (w/v) of a compound selected from the group consisting of 5'-deoxy-5'-methylselenoadenosine, a compound of Formula (I), and combinations thereof. In other embodiments, an effective amount of the composition decreases expression of PSEN1 and/or NICASTRIN in neuronal cells as compared to neuronal cells not treated with the composition.

In further embodiments, a method or use for decreasing expression of phosphorylated Tau (pTau) in a subject, comprises administering a composition to the subject, the composition comprising at least about 0.033% (w/v) to at least about 0.1% (w/v) of a compound selected from the group consisting of 5'-deoxy-5'-methylselenoadenosine, a compound of Formula (I), and combinations thereof. In still other embodiments, an effective amount of the composition decreases expression of pTau in neuronal cells as compared to neuronal cells not treated with the composition.

In further embodiments, a method or use for decreasing expression of Beta-secretase (BACE) in a subject comprises administering a composition to one or more neuronal cells, the composition comprising at least about 0.033% (w/v) to at least about 0.1% (w/v) of a compound selected from the group consisting of 5'-deoxy-5'-methylselenoadenosine, a compound of Formula (I), and combinations thereof. In still other embodiments, an effective amount of the composition decreases expression of BACE in neuronal cells as compared to neuronal cells not treated with the composition.

In further embodiments, a method or use for increasing expression Insulin-Degrading Enzyme (IDE) in a subject comprises administering a composition to one or more neuronal cells, the composition comprising at least about 0.033% (w/v) to at least about 0.1% (w/v) of a compound selected from the group consisting of 5'-deoxy-5'-methylselenoadenosine, a compound of Formula (I), and combinations thereof. In still other embodiments, an effective amount of the composition decreases expression of IDE in neuronal cells as compared to neuronal cells not treated with the composition.

In further embodiments, a method or use for decreasing expression of Regulator of Calcineurin 1 (RCAN1) in a subject comprises administering a composition to one or more neuronal cells, the composition comprising at least about 0.033% (w/v) to at least about 0.1% (w/v) of a compound selected from the group consisting of 5'-deoxy-5'-methylselenoadenosine, a compound of Formula (I), and combinations thereof. In still other embodiments, an effective amount of the composition decreases expression of RCAN1 in neuronal cells as compared to neuronal cells not treated with the composition. In yet other embodiments, an effective amount of the composition decreases expression of RCAN2 and RCAN3 in neuronal cells as compared to neuronal cells not treated with the composition.

In additional embodiments, a method or use for increasing expression of Glucose-6-Phosphatase (G6PC) in a subject comprises administering a composition to one or more neuronal cells, the composition comprising at least about 0.033% (w/v) to at least about 0.1% (w/v) of a compound selected from the group consisting of 5'-deoxy-5'-methylselenoadenosine, a compound of Formula (I), and combinations thereof. In other embodiments, an effective amount of the composition increases expression of G6PC in neuronal cells as compared to neuronal cells not treated with the composition, and does not increase expression of G6PC in liver cells.

In some embodiments, a method or use for decreasing expression of phosphorylated FOXO3 and/or phosphorylated FOXO4 in a subject comprises administering a composition to the neuronal cells of the subject, the composition comprising at least about 0.033% (w/v) to at least about 0.1% (w/v) of a compound selected from the group consisting of 5'-deoxy-5'-methylselenoadenosine, a compound of Formula (I), and combinations thereof. In other embodiments, an effective amount of the composition decreases expression of phosphorylated FOXO3 or phosphorylated FOXO4 in neuronal cells as compared to neuronal cells not treated with the composition.

In further embodiments, a method or use for decreasing expression of PPARG in a subject, comprises administering a composition to the subject, the composition comprising at least about 0.033% (w/v) to at least about 0.1% (w/v) of a compound selected from the group consisting of 5'-deoxy-5'-methylselenoadenosine, a compound of Formula (I), and combinations thereof. In other embodiments, an effective amount of the composition decreases expression of PPARG in neuronal cells as compared to neuronal cells not treated with the composition.

In further various embodiments, a method or use for decreasing expression of one or more of UCP 1-5, INSR, IGF1R, GSK3B, insoluble FA-soluble Aβ1-42 or MAPK 11-14 in a subject comprising administering a composition to one or more neuronal cells of a subject, the composition comprising at least about 0.033% (w/v) to at least about 0.1% (w/v) of a compound selected from the group consisting of 5'-deoxy-5'-methylselenoadenosine, a compound of Formula (I), and combinations thereof. In other embodiments, an effective amount of the composition increases expression of one or more of UCP 1-5, INSR, IGF1R, GSK3B, insoluble FA-soluble Aβ1-42 or MAPK 11-14 in neuronal cells as compared to neuronal cells not treated with the composition.

In further various embodiments, a method or use for increasing expression of one or more of Isl1, ZIC 1-5, Foxp2, Tac1, PenK, Dlx5, Rarb, Gpr88, PGC1a or Pde10a in one or more neuronal cells of a subject, comprises administering a composition to the one or more neuronal cells, the composition comprising at least about 0.033% (w/v) to at least about 0.1% (w/v) of a compound selected from the group consisting of 5'-deoxy-5'-methylselenoadenosine, a compound of Formula (I), and combinations thereof. In other embodiments, an effective amount of the composition increases expression of one or more of Isl1, Zic 1-5, Foxp2, Tac1, PenK, Dlx5, Rarb, Gpr88, or Pde10a in neuronal cells as compared to neuronal cells not treated with the composition.

In further embodiments, a method or use for assessing cell viability in a subject comprising administering a composition to the subject, the composition comprising at least about 0.033% (w/v) to at least about 0.1% (w/v) of a compound selected from the group consisting of 5'-deoxy-5'-methylselenoadenosine, a compound of Formula (I), and combinations thereof. In other embodiments, an effective amount of the composition has no inhibitory effect on NOTCH signaling in neuronal cells as compared to neuronal cells not treated with the composition and/or is not toxic to the cells or subject.

In additional embodiments, a method or use for treating Alzheimer's Disease in a subject comprises administering a composition to the subject, the composition comprising at least about 0.033% (w/v) to at least about 0.1% (w/v) of a compound selected from the group consisting of 5'-deoxy-5'-methylselenoadenosine, a compound of Formula (I) and combinations thereof. In other embodiments, any of the methods described herein can employ a composition that excludes 5'-Selenoadenosyl homocysteine and/or Gamma-L-glutamyl-Se-methyl-L-selenocysteine.

Methods of determining gene expression in a cell of a subject are known to those of skill in the art, and may include hybridization with primers and/or probes, such as on an array or by PCR methods. Arrays and/or primers for determining gene expression are commercially available. Primers and arrays or microarrays may be readily designed using publicly available sequences for the genes described herein, such as p38, APOE4, BACE, IDE RCAN and Neprilysin. For example, Exemplary sequences for p38 are found at NM_139013.2, GI:194578904, Gene ID.1432; APOE4 are found at NM_001302689.1, GI:705044062, Gene ID. 348; Neprilysin are found at NM_000902.3, GI:116256328, Gene ID.4311; BACE are found at NM_001207048.1 GI:333440465, Gene ID.23621; RCAN are found at NM_004414.6, GI:557786106, Gene ID. 1827; and IDE are found at NM_001165946.1, GI:260099675, Gene ID.3416.

Modulation of gene expression in neuronal cells can be determined as described herein using a number of assays on a sample taken from a subject treated in accord with the compositions described herein. In embodiments, a subject is an animal, preferably, an animal that serves as a model for a disease state.

In other embodiments, the effective amount of the compounds and compositions of the present disclosure is an amount effective to ameliorate symptoms of disease or a disorder (e.g., Alzheimer's Disease) or to modulate gene expression as described herein without being toxic to the cells. In addition, the composition comprising the compounds described herein do not adversely affect glucose metabolism in liver cells.

Prior therapeutic candidates for treatment, prevention, or diagnosis of Alzheimer's Disease have had an adverse effect on NOTCH gene expression. However, the compositions and/or compounds do not affect the expression of one or more of the NOTCH genes. In addition, the compositions and/or compounds as described do not exhibit toxicity, do not inhibit mitochondrial potential, and/or do not increase expression of PSEN1 and/or NICASTRIN as measured in neuronal cells in vitro.

As is well known in the medical or research arts, dosages for any one subject may depend upon many factors, including, but not limited to, the patient's size, body surface area, age, the particular compound to be administered, sex, timing, and route of administration, general health, and interaction with other drugs being concurrently administered. In embodiments, the dose of the present composition may be adjusted depending on efficacy or the presence of overt signs of selenium toxicosis are observed in the subject. Selenium toxicosis may be indicated by symptoms including, but not limited to, garlicky breath, hair loss, or flaky nails.

In some embodiments, the dose of the present composition is administered at least once daily for a period of time to achieve a steady state of elemental selenium in the blood. In embodiments, the dose is administered daily for at least 60 or 90 days. In yet other embodiments, the dose of the present composition may be administered while the subject is experiencing symptoms of a disease or disorder.

EXAMPLES

The following examples provide illustrative examples or embodiments of the compositions, compounds, and methods of the present disclosure. Illustrative embodiments of the compounds, composition, and methods of the present disclosure are provided herein by way of examples. While the concepts and technology of the present disclosure are susceptible to various modifications and alternative forms, specific embodiments thereof have been shown by way of example in the figures and will be described here in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

It will be appreciated that the technology described herein has broad applications. The foregoing embodiments were chosen and described in order to illustrate principles of the technology as well as some practical applications. While certain embodiments have been described and/or exemplified herein, it is contemplated that considerable variation and modification thereof are possible.

Example 1: Synthesis and Characterization of 5'-deoxy-5'-methylselenoadenosine ("Compound C")

The synthesis scheme and methodology to produce Compound C was:

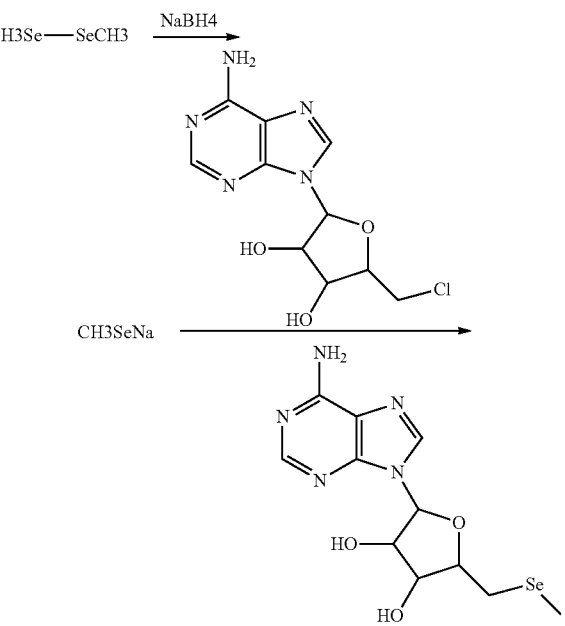

Sodium borohydride (227 mg, 6.0 mM, under Ar°) was placed in a 200 mL round-bottom flask containing 20 mL of anhydrous ethyl alcohol, equipped in a magnetic stirrer and located in an ice cooling bath. Dimethyldiselenide (190 uL, 376 mg, 2.0 mM), was added to the flask with cooling, stirring and under Ar flow. After formation of a yellowish solution, solid 5'-chloro-5'-deoxyadenosine (1,143 g, 4.0 mM) was added. 100 mL of ethyl alcohol was added to dissolve the precipitate. The mixture was stirred at room temperature for the following four days. Mass Spectrometry was used to monitor the approximately 75% conversion that was accomplished after five days. The solvents were evaporated, and 3.22 g of the product (with approximately 20% of starting material (SM)) was collected and purified by the reverse phase (C-8) preparative chromatography. A yield of 1.1 g of pure product was collected, which had its molecular weight confirmed by mass spectrometry.

Example 2: Synthesis and Characterization of Se-Adenosyl-L-homocysteine ("Compound D")

The synthesis scheme and methodology to produce Compound D is shown below:

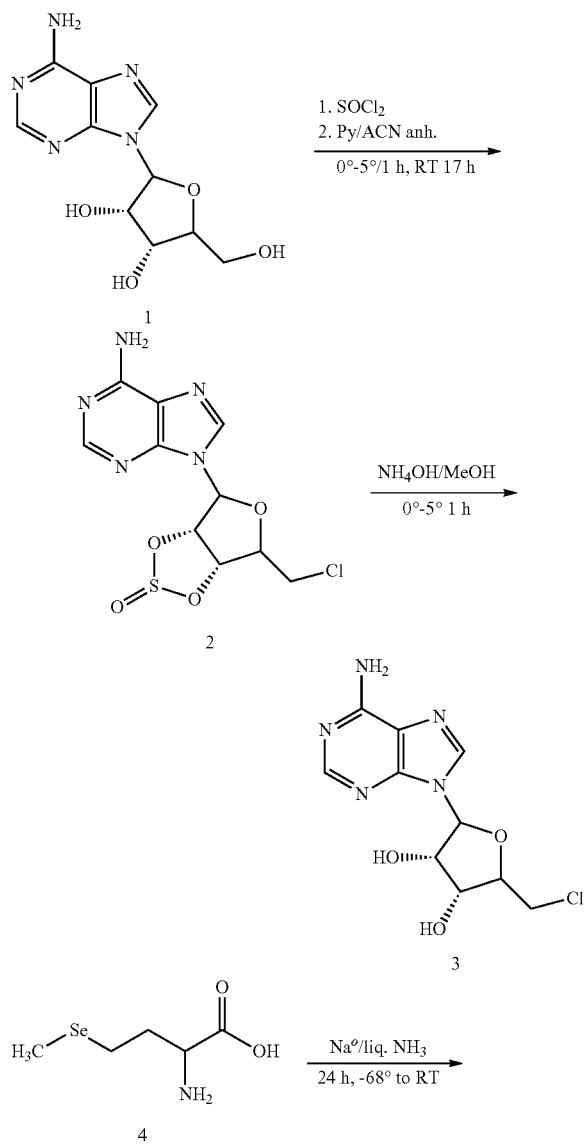

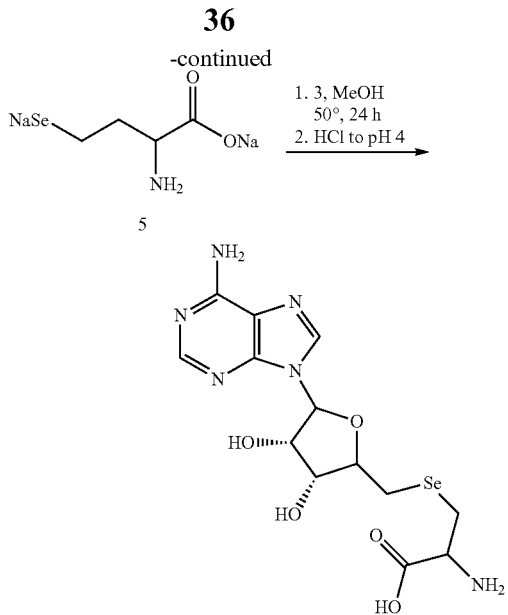

5'-Chloro-5'-deoxyadenosine (639-62)

Eighty-nine (89) grams (0.366 mole, 1 eq.) adenosine, 59.3 mL (58, 1.833 mole, 2 eq.) anhydrous pyridine and 1 L anhydrous acetonitrile was placed in an oven dried, 2 L, 4 neck flask, equipped in a dropping funnel, a stirrer, gas inlet/outlet and a thermometer. The reaction set was placed in an ice/salt bath and agitation was initiated. When the temperature of the solution dropped below 3° C., thionyl chloride was added slowly. The temperature of the reaction mixture was maintained below 5° C. during thionyl chloride addition and for 4 h more (at this time the solution is yellow with white-yellow precipitate on the bottom). The reaction was left overnight at ambient temperature.

The next morning the voluminous precipitate was filtered off using sintered glass filter and washed on the filter with 300 ML volume of dry acetonitrile. During this time, the precipitate color changed into white. The wet precipitate was then transferred back into the 2 L reaction flask containing a mixture of 800 ML of methanol and 160 ML of water. Eighty milliliters (80 ML) of concentrated ammonium hydroxide solution was added drop-by-drop to the reaction flask with mechanical stirring and cooling with a water bath. The mixture was agitated for 45 min at ambient temperature and a white precipitate formed, which was separated from the liquid by vacuum filtration.

The filtrate was concentrated to dryness using a vacuum rotary-evaporator while the precipitate was crystallized from approximately 560 ML hot water. The precipitate was cooled in an ice-water bath, and the first crop of the crystals was filtered off and freeze-dried. The filtrate was used as a solvent in the crystallization of solids, which resulted from the rotary evaporation of the first filtrate to obtain the second crop of the product. The second crop of the product was also freeze-dried for two days. Both crops of crystals were finally dried for two days over phosphorous pentoxide in a vacuum dessicator. Eighty-four (84) grams of white crystals, with a 80.5% yield are obtained. MS (286-M+H), mp. 187° C. Selenoadenosylhomocysteine (655-40).

L-selenomethionine (9.806 gram, 50 mM, 1 eq.) was charged into a 2 L, three-neck flask equipped in a thermometer, a large cooling finger (with bubble-meter at the outlet), ammonia gas inlet (reaching bottom of the flask) and a magnetic stirring bar and placed in a 2.5 L duar vessel containing CO$_2$-Acetone cooling bath. Ar° was passed through the flask before adding solid CO$_2$ to the acetone bath and the cooling finger. When the temperature inside the flask drops below −35° C. the flow of anhydrous ammonia (gas) was started and when liquid ammonia levels reached the volume of 800 ML the gas flow was stopped.

Small pieces of metallic sodium were added to a well stirred solution until blue-violet coloration of the solution persists for approximately 30 sec. A total of 2.645 gram (115 mM, 2.3 eq.) of sodium was added within 45 min. Agitation and cooling was maintained for 30 min more. At this time all of the components were in the solution. Anhydrous 5'-chloro-5'-deoxyadenosine (14.856 gram, 52 mM, 1.04 eq.) was added in a single portion and the reaction mixture was left with stirring and very slow Ar° flow overnight.

The next morning, 350 ML of anhydrous methanol was added to the white solids which were present in the flask. The flask was placed in an oil bath, a reflux condenser was installed, Ar° gas flow was maintained, and an oil bath was heated to 50° C. for the subsequent 24 hours. One milliliter (1 ML) of the solution was acidified to pH 3.5 with a few drops of 0.1N HCl, and the sample was analyzed for the presence of substrates using mass spectrometry.

If below 5%, the mixture can be acidified with 1N HCl to pH 3.5, filtered from salts, concentrated to dryness using vacuum rotary-evaporator and the crude product can be purified by crystallization from water-ethanol mixture. The first crop of Selenoadenosylhomocysteine crystals yielded 15.98 gram of product with a 74% yield. Yet, approximately 95% of the product was clean, and could be used in biological studies without further purification.

Example 3: Synthesis and Characterization of Gamma-glutamyl-methylselenocysteine ("Compound E")

The synthesis scheme and methodology to produce Compound E is shown below:

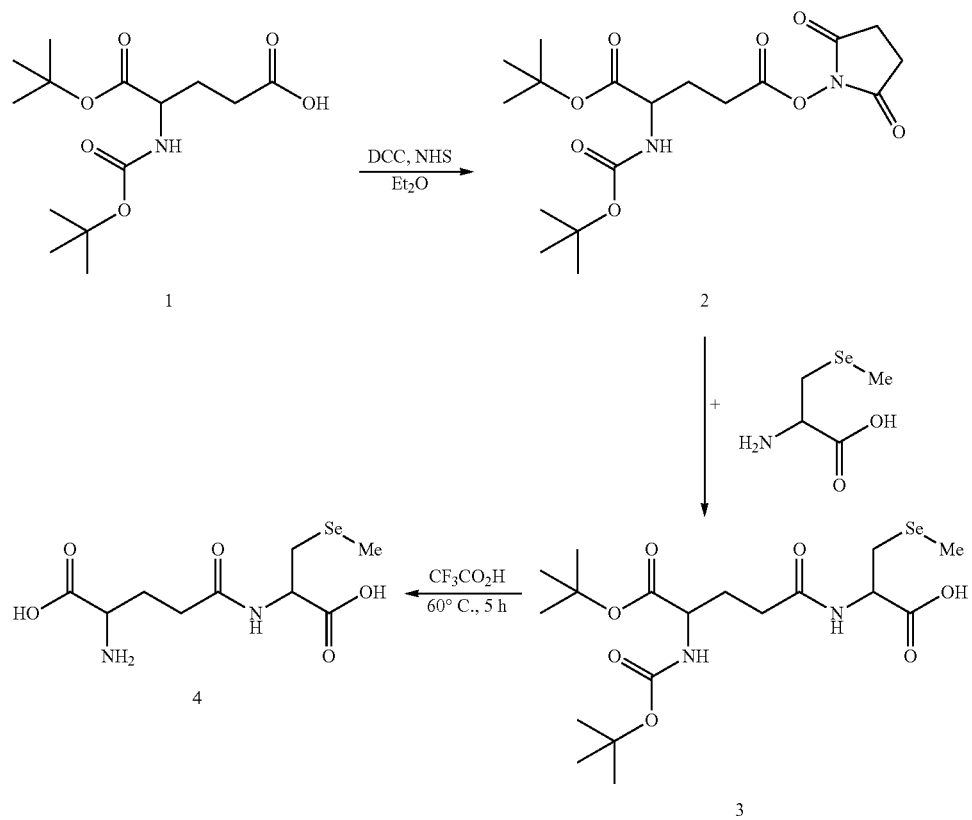

Synthesis of N-Boc-(O-tBu)-L-Glu-OSe (655-90)

N-Boc-(O-tBu)-L-Glu-OH (303 mg, 1.0 Mmol), N-hydroxysuccinimide (121 mg, 1.05 Mmol) and dicyclohexyl carbodiimide (227 mg, 1.1 Mmol) were suspended/dissolved in 15 ML of anhydrous ethyl ether and 10 uL of dimethylethylbenzylamine was added from a syringe into the reaction mixture. Stirring at ambient temperature (22° C.) was maintained for 48 h. The mixture was filtered and the precipitate was washed 10×10 mL of ethyl ether. The filtrate was concentrated and dried under high vacuum yielding white crystalline product (570 mg, ~90% yield). MS (M+Na$^+$)=423.17.

Synthesis of N-Boc-(O-tBu)-L-Glu-MeSe-Cys-OH (655-90)

N-Boc-(O-tBu)-L-Glu-OSe (570 mg, 0.9 Mmol), methylselenocysteine (175 mg, 0.8 Mmol), triethylamine (152 mg, 209 µL, 1.5 Mmol) were added into a mixture of 6 mL of 1,4-Dioxane and 2 mL of water. Magnetic stirring of the reaction mixture was maintained for 100 h. After this time 1.21N HCl (1.65 mL) was added and the post-reaction mixture was extracted with three rounds (3×) of 20 mL of ethyl ether. The extract was concentrated to dryness using a vacuum rotary-evaporator yielding 649 mg of waxy product that was submitted to preparative HPLC. Two hundred eighty-three milligrams (283 mg) of the product were collected having a 75.6% yield. Mass spectrum confirmed the molecular weight of the product, and the presence of a single Se atom in it. Calculated mass for $C_{18}H_{32}N_2O_7Se=468.42$; These results found 469.24 m/e (M+H±) and 491.24 m/e (M+Na+).

Synthesis of Y-Glutamyl-methylselenocysteine (655-92)

A mixture of 283 mg (0.6 Mmol) of N-Boc-(O-tBu)-L-Glu-MeSe-Cys-OH, 2 mL of thioanisol, and 5 mL of trifluoroacetic acid were heated with magnetic stirring in an oil bath for 6 hours and at 63° C. The mixture was left over night at ambient temperature (22° C.). The reaction mixture was added drop-by-drop into 20 ML of a vigorously stirred ethyl ether. The precipitate that formed was washed with two rounds (2×) of 20 MLmL of ethyl ether. The product yielded 138.3 mg of creamy precipitate, which was then purified by preparative HPLC.

Example 4

Synthetic individual selenoorganic compounds were tested in cell culture (in vitro) for effects on mitochondrial function, cell survival or viability, and gene expression in the examples described herein. In particular, the cells tested were human IMR-32 neuronal cells.
Cell Lines and Compounds Human neuroblast IMR-32 cells were purchased from American Type Culture Collection (ATCC, Manassas, Va.). All cells were cultured or amplified using culture media recommended by ATCC.

Compound C (5'-deoxy-5'-methylselenoadenosine), Compound D (Se-Adenosyl-L-homocysteine)), and Compound E (Gamma-glutamyl-methylselenocysteine)), and their sulfur analogs, Compound H (5'-deoxy-5'-methylthioadenosine), Compound I (S-Adenosyl-L-homocysteine), and Compound J (Gamma-glutamyl-methyl-cysteine) were either synthesized or obtained from commercial sources (where available). The purities of all tested compounds were verified to be greater than or equal to (>) 99% as determined by mass spectrometry.

The ppb values shown in these examples herein refer to ppb of selenium in selenium containing compounds or ppb of sulfur in sulfur containing compounds in order to ensure equivalent amounts of selenium or sulfur were being tested in the experiments.

In order to convert ppb based on selenium to ppb of the compound, the % of Se in a compound is calculated by dividing the atomic weight of selenium by the molecular weight of the compound and multiplying the dividend by 100. In order to convert ppb based on sulfur to ppb of the compound the % of S in a compound is calculated by dividing the atomic weight of sulfur by the molecular weight of the compound and multiplying the dividend by 100.

For example, dividing the atomic weight of Selenium of 78.96 by the molecular weight of Compound C of 344 and multiplying the result by 100, results in a % of selenium in Compound C of 23%. Likewise, for Compound D, dividing the atomic weight of Selenium of 78.96 by the molecular weight of Compound D of 432 and multiplying the result by 100, results in a % of selenium in Compound D of 18%. For Compound E, dividing the atomic weight of Selenium of 78.96 by the molecular weight of Compound E of 311 and multiplying the result by 100, results in a % of selenium in Compound E of 25%.

These % Se values are used to derive factors for converting ppb of selenium to ppb of the compound. These factors are: 4.35 for Compound C, 5.46 for Compound D, and 3.94 for Compound E. In order to convert ppb based on selenium to ppb of the compound multiply the indicated ppb of selenium by the factor for each compound as shown in the Table below. For example, 150 ppb of Compound C in the experiments below refers to 150 ppb of selenium and is equivalent to 653 ppb of Compound C.

For the sulfur compounds, dividing the atomic weight of Sulfur of 32 by the molecular weight of Compound H of 297 and multiplying the result by 100, results in a % of sulfur in Compound H of 11%. Likewise, for Compound I, dividing the atomic weight of Sulfur of 32 by the molecular weight of Compound I of 384 and multiplying the result by 100, results in a % of sulfur in Compound I of 8%. For Compound J, dividing the atomic weight of Sulfur of 32 by the molecular weight of Compound J of 264 and multiplying the result by 100, results in a % of sulfur in Compound J of 12%.

These % S values are used to derive factors for converting ppb of sulfur to ppb of the compound. These factors are: 9.28 for Compound H, 12.00 for Compound I, and 8.25 for Compound J. In order to convert ppb based on sulfur to ppb of the compound multiply the indicated ppb of sulfur by the factor for each compound as shown in the Table below. For example, 150 ppb of Compound H as described in the experiments below refers to 150 ppb of sulfur and is equivalent to 1392 ppb of Compound H.

| ppb Selenium Delivered by the Compound | Equivalent ppb Compound C | Equivalent ppb Compound D | Equivalent ppb Compound E |
|---|---|---|---|
| 100 | 435 | 546 | 394 |
| 150 | 653 | 819 | 591 |
| 200 | 870 | 1092 | 788 |
| 300 | 1305 | 1638 | 1182 |
| 450 | 1958 | 2457 | 1773 |
| 600 | 2610 | 3276 | 2364 |
| 900 | 3915 | 4914 | 3546 |

| ppb Sulfur Delivered by the Compound | Equivalent ppb Compound H | Equivalent ppb Compound I | Equivalent ppb Compound J |
|---|---|---|---|
| 100 | 928 | 1200 | 825 |
| 150 | 1392 | 1800 | 1238 |
| 200 | 1856 | 2400 | 1650 |
| 300 | 2784 | 3600 | 2475 |
| 450 | 4176 | 5400 | 3712 |
| 600 | 5568 | 7200 | 4950 |
| 900 | 8352 | 10800 | 7425 |

Generation of Control and FOXO4 Knockdown (KD) IMR-32 Cells

IMR-32 cells were cultured on 12-well plates for 24 hours and then incubated with FOXO4 siRNA lentiviruses (SC-29650V, Santa Cruz) or control siRNA lentiviruses (sc-108080, Santa Cruz) in the presence of Polybrene (5 μg/ml, Santa Cruz) for 24 hours according to the manufacturer's protocol. These lentiviral siRNA-transfected cells were amplified in normal media for 3 days and then incubated with puromycin for 9-14 days to obtain the stable Control KD (stably transfected with the control siRNAs) and FOXO4KD (stably transfected with Foxo4 siRNAs) cells. These control and Foxo4 KD cells were subjected to cell survival, mitochondrial potential and RNA analysis.

Cell Viability Assay and Cell Survival Studies of FOXO4 KD Cells

Cell viability in cultured IMR-32 cells was determined using Promega's CellTiter96® AQueous One Solution Cell Proliferation Assay kits, according to the manufacturer's protocol and instructions. In brief, IMR-32 cells were seeded on 96-well clear plates (VWR) at a density of $2 \times 10^4$ cells/well, and treated with control or compounds of the present invention for 24 hours, 28 hours, and/or 72 hours.

The cultured cells were then incubated with AQueous One solution (100 ul/per well) at 37° C. for 1 hour. The absorbance at OD490 nm in each sample was determined by a Bio-Tek microplate reader. Cell viability in cultured cells were determined by the subtraction of OD490 nm in cultured cells with the OD490 nm in plain culture media without seeding of cells (control). Eight samples per each treatment were examined for the above analysis.

Cell survival analysis in prolonged culture of control lentiviral knockdown cells and in FOXO4 knockdown (KD) cells was determined by seeding equal number of control and FOXO4KD cells on the culture dishes followed by splitting cells at the same ratio every 4 days between control and FOXO4KD cells for the following 48 days of culture. The morphology of these cells during the culture time period was monitored and captured using an inverted phase-contrast microscope (Zeiss, Germany).

Quantitative Analysis of Mitochondrial Potential in FOXO4 Knockdown (KD) IMR-32 Cells The mitochondrial potential per cell in control lentiviral KD IMR-32 or IMR-32 FOXO4 knockdown (KD) cells was determined using the Bio-TeK Synergy HT Multi-Mode fluorescence microplate reader with the following modifications. To improve the attachment of IMR-32 cells to culture dishes, cell culture plates were precoated with 0.1% gelatin (Sigma, St. Louis, Mo.).

Equal number of IMR-32 cells ($2 \times 10^4$ cells/well), control KD or FOXO4KD cells were seeded on gelatin-coated Corning 96-well dark-walled cell culture plates (VWR, Radnor, Pa.), cultured in Eagle's minimum essential medium (EMEM, ATCC) containing 10% fetal bovine serum (FBS) for 24 hours, and then treated with control (0 ppb) or 75 ppb or 150 ppb of Compound C (diluted in culture media either in the presence or absence of FBS) for 6 hours and 24 hours. To reduce cell dislodgment, Mitotracker Orange and Hoechst 33342 fluorescent dyes (diluted in culture media) were directly added to each well after control or compound treatments were added. After dye incubation, cell culture media was carefully replaced with 1×PBS buffer for the quantitation analysis of fluorescence on the microplate reader. Eight samples per each treatment were examined for the above analysis, and the experiments were repeated at least five times. Data are presented as mean±sem of eight samples.

RNA Isolation and Real-Time PCR Analysis

Human IMR-32 cells were seeded on gelatinized 6-well ($6.5 \times 10^5$ cells/well) or 24-well ($1.3 \times 10^5$ cells/well) plates. Cells were treated with control (0 ppb) or various compounds for 6 hours or 24 hours. Total RNA from these cells was isolated using Trizol (Invitrogen) according to the manufacturer's protocol, and then incubated with DNase I to remove any potential contaminated genomic DNA. Then RNA samples were subjected to real-time PCR analysis using the Applied-Bioscience's RT kit and predesigned Taqman probes (Invitrogen), as described previously (Lan et al EMBO J 2003). The mRNA levels of UCP1, UCP2, UCP3, SLC25A27 (UCP4), SLC25A14 (UCP5), PSEN1, Nicastrin, GSK3B, MAPK11-14, PPARG, APOE, RCAN1, RCAN1.1, G6PC, INSR, IGF1R and FOXO4 were measured. Three to six samples were analyzed in each treatment group. Data were normalized by Actin B (ACTB) or Glyceraldehyde Phosphate Dehydrogenase (GAPDH) mRNA levels in each sample and are presented as mean±SEM of 3-6 samples.

Protein Preparation and Western Blot Analysis

IMR-32 cells were seeded on 6-well plates and then treated with control and various compounds for 6 hours and 24 hours, as described above. After treatments, cells were rinsed with ice-cold PBS and lysed in ice-cold RIPA buffer containing complete proteinase and phosphatase inhibitors (Thermo-Fisher Scientific, Waltham, Mass.) on ice for 30 min Cell lysates were collected using a cell scraper and transfer pipette and then centrifuged at 12000×g for 30 min at 4° C. to remove the DNA pellet and obtain the protein extract. Protein levels in the supernatant of these cell lysates were determined using the Pierce Micro-BCA protein assay kit (Thermo Scientific-Piece Biotechnology, Rockford, Ill.) according to the manufacturer's protocol For Western blot analysis, five micrograms of total proteins from control (0 ppb)- and compound(s)-treated cells were subjected to SDS-PAGE gel separation and then transferred to PVDF membranes, as described previously (Reddy, Liu et al. 2008 Science). Membranes were blocked in a phosphate-buffered saline (PBS) containing 5% (w/v) of bovine serum albumin (Sigma, St. Louis, Mo.) and incubated with specific primary antibodies followed by the incubation with HRP-conjugated anti-mouse or anti-rabbit secondary antibodies (1:5000 dilution, Cell Signaling Inc.). All primary antibodies except PGC1a (Abcam, Cambridge, Mass.), G6pc (Santa Cruz, Dallas, Tex.) and Actb (Li-Cor, Lincoln, Nebr.) were purchased from Cell Signaling Inc., Beverly, Mass.

Positive signals on the membrane blots were detected using Amersham's enhanced chemiluminescence (ECL) Western Blotting Prime Detection reagents (GE healthcare Lifescience, Pittsburgh, Pa.). Images of these luminescence signals on the membrane blots were captured using the LI-COR Odyssey Fc Image system (Lincoln, Nebr.). The same membrane blot was stripped and re-blotted with another antibody as described in the GE WB ECL-prime-detection protocol (GE Healthcare Lifescience, Pittsburgh, Pa.). Protein band densities in the Western blots were determined using the Li—COR Image studio software or NIH ImageJ software, and then normalized by ACTB protein level in each sample. Data are presented as mean±SEM of three samples per each group.

Statistical Analysis

If applicable, a student's T-test was performed to determine the statistical difference between two groups. A p-value less than 0.05 was considered significant.

Results and Discussion

Effects of Compound C, Compound D, and Compound E on the Cell Survival of IMR-32 Cells Cell viability assays were performed on cells after treatment with various compounds (150 ppb selenium compounds and equal dilution of their sulfur analog) for 24 hours, and 72 hours. Treatment of all compounds for the tested time points did not cause a significant decrease of viable IMR-32 cells (see FIGS. 1A-1B; Mean±SEM, n=8. The * in FIG. 1B refers to P<0.05 when compared to control or its sulfur analog group. The @ in FIG. 1B refers to P<0.05 when compared to its sulfur analog group). In fact, there was a small, but significant increase of cell viability in cells after selenium Compound C treatments for 72 hours (see FIG. 1B).

These data suggest that selenium compounds did not have a toxic effect on the survival of IMR-32 cells, but instead, Compound C had a small but significant beneficial effect on IMR-32 neuronal cell survival.

Compound C, a Mitochondrial (MT) Enhancer and Modulator of the Expression of PGC1a and UCPs Key for MT Function in Human IMR-32 Cells Mitochondrial (MT) dysfunction and dysregulated glucose metabolism are associated with the onset of Alzheimer's Disease (AD). Likewise, as AD progresses, there is strong evidence that Aβ and Tau protein species precipitate further mitochondrial decline. To investigate if Compound C can regulate MT function in neuronal cells, human IMR-32 cells were treated with two doses of Compound C (75 ppb and 150 ppb) for 6 hours and 24 hours, and then subjected to mitochondrial assays using a Mitotracker Orange dye (Invitrogen, Grand Island, N.Y.) according to the manufacturer's protocol.

As shown in FIGS. 2A-C, treatment of Compound C at both doses in IMR-32 cells for 6 hours remarkably enhanced their MT potential (as indicated by the red fluorescence intensities) when compared to control cells. Quantitative analysis showed there was a significant increase of MT potential in IMR-32 cells after treatment with Compound C at 75 ppb and 150 ppb for 6 hours and 24 hours. (FIGS. 2D-2E). Data shown in FIG. 2D (6 hours) and 2E (24 hours) were normalized by the fluorescence intensities of stained cell nuclei. A significant p value <0.05 was obtained between the control group (0 ppb) and the group treated with Compound C.

Together, the findings demonstrate that Compound C is a stimulator of mitochondrial potential in neuronal IMR-32 cells.

Peroxisome Proliferator-Activated Receptor Gamma Coactivator 1-alpha (PGC-1α) is a potent transcriptional activator that regulates genes involved in energy metabolism. PGC-1α is also the chief regulator of mitochondrial biogenesis and growth. PGC-1α provides a direct link between external stimuli, such as exercise, and the regulation of mitochondrial biogenesis. PGC-1α also performs a diversity of functions by teaming with different transcription factors to co-activate genes. In the context of neuronal-specific mitochondrial activity and AD progression, it is of interest to note that PGC-1α expression decreases in the Alzheimer's Disease brain as function of dementia.

The PGC-1α protein levels in IMR-32 cells treated with Compound C, Compound D, and Compound E was examined FIG. 2F shows an increase in PGC-1α protein in IMR-32 cells treated with Compound C, Compound D, or Compound E by Western blot. FIG. 2G is a bar graph showing an increase of the normalized PGC-1α protein levels in IMR-32 cells treated with Compound C, Compound D, or Compound E. The symbol "b" as compared to "a" in FIG. 2G indicates the expression amounts were significant between those two groups with a p value <0.05.

PGC-1α protein levels were markedly elevated after 24 hour treatment with all three compounds (see FIGS. 2F-G). Thus, it was concluded that Compound C, Compound D, and Compound E were PGC-1α upregulators. This data provides evidence that synthetic organoselenium (selenoorganic) compounds, especially Compound C, have the ability to significantly increase mitochondrial activity in neuronal cells.

Another candidate family of genes which have the ability to increase or decrease mitochondrial activity is Uncoupling Proteins or UCPs. In particular, UCP2 and UCP3 are genes are involved in the regulation of MT potential. Lower levels of expressions of UCP genes are associated with increased MT activity The elevated MT potential observed in IMR-32 cells in response to Compound C prompted testing as to whether there is differential mRNA expression of the UCP genes in response to compound treatment (see FIGS. 2H-2K).

The relative mRNA expression of all five UCP genes (UCP 1-5) in normal IMR-32 cells was assessed (see FIG. 2H). It was determined that the expression level of UCP2 was highest, followed by UCP5, and then UCP3, UCP1 and UCP4 (SLC23A27) mRNA expression levels were almost undetectable in IMR-32 cells (FIG. 2H).

Treatment with 150 ppb of Compound C, Compound D, and Compound E of IMR-32 occurred for 6 hours (see FIG. 2I-2K; A number inside the bars refer to the number of replicates used for that group.). Compound C caused a significant decrease of UCP2 and UCP3 mRNA expression, and a trend towards decreased UCP5 (SLC25A14) expression in IMR-32 cells (see FIGS. 2I-K). Compound D also significantly inhibited UCP3, but did not inhibit UCP2 or UCP5 mRNA gene expression (see FIGS. 2I-K). Compound E did not have any effect on the gene expression of UCP2, UCP3, or UCP5 genes (FIG. 2I-K). These results suggest that the downregulation of relative mRNA expression of UCP2 and UCP3 by Compound C may offer another explanation for the enhanced MT potential observed in IMR-32 cells in response to this compound.

Together, the results show that both 75 ppb and 150 ppb of Compound C increased mitochondrial potential in IMR neuronal cells, and that Compound C is not only a PGC-1α upregulator, but also a UCP2, and UCP3 downregulator. Compound D is also a PGC-1α upregulator and UCP3 downregulator, while Compound E is a PGC-1α upregulator, but has no effect on UCP expression. Based on these results, Compound C is likely to have the most beneficial effect on MT function in IMR-32 cells.

Organoselenium compounds, especially Compound C, have the ability to significantly increase mitochondrial activity in neuronal cells. Mechanistically, modulation of UCPs may offer one explanation for this increase and present evidence that the expression of other proteins, such as PGC1α, associated with mitochondrial function and biogenesis, may also be favorably affected by these compounds. Any agent which can increase mitochondrial function in diverse tissues will be extremely valuable as an intervention for conditions tracing their origins to mitochondrial decline.

Example 5

Compound C, a Modulator of the Expression of Genes Relating to AD Pathogenesis

Compound C, a Compound to Inhibit the Expression of the Gamma-Secretase Complex Genes PSEN1 and Nicastrin in IMR-32 Cells A key pathological feature of AD is amyloid plaques which occur between neurons and which contribute to brain atrophy and cell death. The mechanisms involved in the production of amyloid plaques are complicated but chiefly rely on the action of an enzyme called beta-secretase (BACE) which acts in concert with a multi-enzyme complex called gamma-secretase. Together, in AD, these enzymes act to aberrantly process a brain protein called amyloid precursor protein (APP). The resulting product is an abnormal amyloid beta peptide which clumps together to form plaques.

As stated, the gamma-secretase enzyme is actually a multimeric complex composed of many members such as Presenilin-1 (PSEN1 or PS1), NICASTRIN, APH-1 (Anterior Pharynx Defective 1) and PEN2 (Presenilin Enhancer 2). While all these components are important for the correct functioning of gamma-secretase, two components in particular have become the focus for pipeline therapeutic drugs, PSEN1 and NICASTRIN.

PSEN1 is the actual catalytic component of the gamma-secretase—the component that physically cleaves the amyloid precursor protein. Furthermore the gene for PSEN1 is the most frequently mutated gene in familial AD. Relative to PSEN2, PSEN1 is much more abundant and is functionally better defined. In IMR-32 cells, the expression level of PSEN1 was almost 8-fold higher than PSEN2 (which was barely detectable by sensitive QRT-PCR analysis, data not shown). NICASTRIN is of interest, not because it is catalytic but because it binds to and orients APP so that Presenilin can cleave it. PSEN1 and NICASTRIN are, therefore, the targets of greatest interest for gamma-secretase-focused AD interventions.

RNA samples were extracted, purified, and subjected to real-time PCR analysis using Applied-Bioscience's RT kit and Taqman probes (Invitrogen) as described previously in Example 4. Protein samples were also prepared from cell lysates and western blot analysis was performed as previously described in Example 4. Data are presented as mean±SEM of 3 protein samples and 4 RNA samples per group. The relative mRNA and protein expression levels of PSEN1 and NICASTRIN, were measured. All primary antibodies were purchased from Cell Signaling Inc., Beverly, Mass.

As shown in FIG. 3A, PSEN1 and NICASTRIN, but not PEN2 proteins, were reduced in IMR-32 cells after 24 hours of treatment with 150 ppb of Compound C. Quantitative analysis showed that there was a significant reduction of PSEN1 and NICASTRIN protein levels only by Compound C (see FIGS. 3B and 3C). However, Compounds D and E also elicited a trend towards reduced NICASTRIN protein expression (FIG. 3C).

Consistent with attenuated PSEN1 protein expression, PSEN1 mRNA expression was significantly reduced by Compound C at both 6 hours and 24 hours after treatment (see FIGS. 3D-3F). To confirm this result, IMR-32 cells were also treated with 0 ppb (control), 75 ppb, and 150 ppb of Compound C. Significant dose-dependent decreases in PSEN1 mRNA expression levels were observed after treatment with both concentrations of Compound C for 24 hours (see FIG. 3F). Thus, Compound C can downregulate PSEN1 expression not only at the mRNA level, but also at the protein level.

Similarly, Compound C treatment also caused a trend towards reduced NICASTRIN mRNA expression in IMR-32 cells after 6 hours treatment (see FIG. 3G). More importantly, a significant decrease in NICASTRIN mRNA expression in IMR-32 cells after 24 hours of treatment was also observed (FIG. 3H). Dose-response studies further confirmed that Compound C at the 150 ppb dose after 24 hour treatment can significantly inhibit Nicastrin expression (FIG. 3I). Data are presented as mean±SEM of 4 samples. In FIGS. 3B-I, different letters in the bar graphs means a significant difference between those two groups (p value <0.05).

In contrast, Compound D and Compound E did not inhibit PSEN1 or NICASTRIN expression, but instead stimulated PSEN1 and NICASTRIN mRNA expression in IMR-32 cells after 24 hours treatment (see FIGS. 3E and 3H). PSEN2 expression was examined and no downregulation by selenium Compound C, Compound D or Compound E was observed (data not shown).

These results indicate that Compound C targets expression of gamma-secretase complex components, such as PSEN1 and NICASTRIN, known to be responsible for plaque formation in AD.

Compound C, a Neuronal Cell-Specific GSK3B Downregulator and Tau Phosphorylation Inhibitor in IMR-32 Cells The second main pathology, in addition to amyloid plaques in AD is caused by Neurofibrillary Tangles or NFTs. Tangle formation in AD is caused by hyperphosphorylation of a protein called Tau, which may be effected by the Glycogen Synthase Kinase 3-Beta (GSK3B) gene.

To determine whether selenium Compound C, Compound D or Compound E can potentially contribute to diminished tangle formation in AD, the phosphorylation of two AD biomarkers, pTau S396 (Serine 396) and pTauS400/T403/5404 (Serine 400, Threonine 403, and Serine 404), as well as the Total Tau protein levels was assessed in IMR-32 cells. Phosphorylation of Tau at the indicated amino acid sites has been associated with destabilization of the Tau protein and the eventual formation of tangles. For this purpose, cells were treated with 150 ppb of Compound C, Compound D, or Compound E for 6 hours and 24 hours, and then subjected to Western blot analysis (see FIG. 4A). Mean±SEM, n=3.

After 6 hours of compound treatment, protein levels of all tested Tau protein species were unaffected (data not shown). However, after 24 hours of treatment, protein levels of pTau 5400/T403/5404 were significantly downregulated in IMR-32 cells by Compound C (FIG. 4A). Quantitative analysis showed that Compound C did not affect total Tau protein level (FIG. 4D), but significantly inhibited the phosphorylation of Tau at 5400/T403/5404 (FIG. 4C), although not at S396 (FIG. 4B). Compound D had no effect on Tau phosphorylation at all tested serine/threonine residues, or on total Tau protein level (FIG. 4A-D), while both the phosphorylation of Tau at S396 and 5400/T403/5404, and total Tau protein were significantly down-regulated by Compound E (FIG. 4A-D). Analysis of the ratio of total pTau at both S396 and S400/T403/S404 to total Tau proteins showed that only Compound C, but not Compound D, significantly attenuated total phosphorylation of Tau protein in IMR-32, even though there was a trend towards reduced Tau phosphorylation at all tested serine/threonine residues by compound E (FIG. 4E). In FIGS. 4B-4E, different letters in the bar graphs means a significant difference between those two groups (p value <0.05).

This data demonstrate that Compound C can markedly inhibit Tau phosphorylation, but does not affect total Tau protein levels in IMR-32 cell. Compound D was not observed to have any effect on the Tau phosphorylation process. However, Compound E may also play a role in the regulation of Tau phosphorylation, but the effect of this compound is likely through the downregulation of Total Tau protein in IMR-32 cells.

Given that hyperphosphorylation of Tau is a cause of tangle formation in AD, our data suggest that Compound C inhibits Tau hyperphosphorylation. Thus, Compound C may be of therapeutic value in preventing NFT formation.

Downregulation of Tau phosphorylation by Compound C was assessed in order to determine if this effect in IMR-32 cells was due to GSK3B, the key kinase for Tau phosphorylation in AD. Western blot analysis was performed to examine GSK3A/B and pGSK3A/B protein levels. As shown in FIG. 4A, GSK3A and phosphorylated GSK3B proteins were not affected by any of the three compounds used to treat IMR-32 cells. While phosphorylated GSK3A was barely detected by the antibodies in these cells (data not shown). However, total GSK3B protein levels were visibly decreased in IMR-32 cells after treatment with Compound C for 24 hours (see FIG. 4A). This same trend was not observed for IMR-32 cells treated with Compounds D and E (see FIG. 4A).

Quantitative analysis demonstrated a statistically significant decrease of GSK3B protein levels in response to Compound C treatment. However, no significant difference was observed with GSK3B protein levels in IMR-32 cells treated with Compounds D and E (see FIG. 4F). In FIGS. 4F-4H, different letters in the bar graphs means a significant difference between those two groups (p value <0.05).

To confirm that GSK3B expression is inhibited by Compound C, quantitative RT-PCR was performed to examine its mRNA level. As shown in FIG. 4G, GSK3B mRNA levels were significantly decreased in IMR-32 cells after treatment with Compound C for 6 hours. In contrast, Compound D and E treatments for 6 hours did not significantly inhibit GSK3B mRNA expression in IMR-32 cells (see FIG. 4G).

To further confirm that Compound C can indeed inhibit GSK3B expression, IMR-32 cells were treated with 75 ppb and 150 ppb of Compound C for 24 hours. As shown in FIG. 4H, GSK3B mRNA levels were significantly downregulated by treatment with both doses of Compound C. Together, these data suggest that Compound C can inhibit GSK3B expression at both the mRNA and protein levels. Additionally, this data demonstrates that downregulation of GSK3B expression by Compound C is likely to be a partial reason for the reduced Tau phosphorylation observed in IMR-32 cells.

Compound C: A Downregulator of p38 (Key for Tau Phosphorylation and Inflammation in AD) in IMR-32 Cells P38 mitogen-activated protein kinase is another Tau protein-phosphorylating kinase which contributes to Tau aggregation and NFT formation. In addition, p38 kinase is involved in the production of proinflammatory cytokines which cause inflammation in AD brains. Thus, p38 inhibitors or downregulators hold the potential to be developed as novel AD therapeutics against AD Tau hyperphosphorylation and inflammation.

IMR-32 cells were treated with selenium Compound C, Compound D, or Compound E for 6 hours and 24 hours, and subjected to Western blot analysis of total p38 proteins using a specific p38 antibody that recognized all four isoforms of p38 (i.e., α, β, γ and δ) (see FIG. 5A). P38 α, β, γ, and δ isoforms are encoded by MAPK14, MAPK11, MAPK12, and MAPK13 genes, respectively. After 6 hours of compound treatment, Total p38 protein levels were not affected by any of the three selenium compounds in IMR-32 cells (data not shown). However, total p38 protein levels were visibly decreased in IMR-32 cells after treatment with Compound C or Compound D for 24 hours. The same effect was not observed for Compound E (see FIG. 5A).

Quantitative analysis demonstrated that there was a statistically significant decrease in Total p38 protein levels in IMR-32 cells treated with Compound C or Compound D, but not Compound E (see FIG. 5B). Thus, Compound C and Compound D are novel downregulators of p38 protein expression that may affect Tau hyperphosphorylation. Mean±SEM, n=3. In FIG. 5B, different letters in the bar graphs means a significant difference between those two groups (p value <0.05).

Compound C: A Downregulator of RCAN1 a Key Protein Involved in Tau Hyperphosphorylation in AD Pathogenesis, MT Function and Anxiety Regulators of Calcineurin (RCAN) genes are inhibitors of phosphatase calcineurin, a calcium/calmodulin-dependent serine/threonine phosphatase. Of the three RCAN genes (i.e., RCAN1, RCAN2 and RCAN3) in mammals, it is documented that RCAN1 is highly expressed in AD brains and can stimulate Tau hyperphosphorylation in AD tangle formation (see reviews in Smith et al, ACS Chem Neurosci, 2012; 3:857-872). In addition, RCAN1 also regulates mitochondrial function and increases susceptibility to oxidative stress in neuronal cells (Peiris et al, Oxidative Medicine and Cellular Longevity, 2014). Recent studies have revealed that RCAN1 is an anxiety stimulator in the brain (Hoeffer et al, J Neuroscience, 2013 • 33:16930-16944).

The relative mRNA expression levels of RCAN 1-3 genes were assessed in normal IMR-32 cells by QRT-PCR. The Taqman probe used for these experiments recognized all isoforms of each RCAN gene. As shown in FIG. 6A, RCAN1 was highly expressed in IMR-32 cells, RCAN3 transcripts were barely detected, and RCAN2 transcripts were not detected at all by their specific Taqman PCR probes. These results suggest that RCAN1 is the major RCAN gene expressed in IMR-32 cells.

The ability of selenium compounds to regulate RCAN1 expression in IMR-32 cells was also assessed. IMR-32 cells were treated with selenium Compounds C, D, or E for 6 hours and 24 hours. The protein was extracted from cell lysates and subjected to Western blot analysis using a specific RCAN1 antibody that recognizes both RCAN1.1 and 1.4 protein isoforms.

It was found that a single 38 kDa band (i.e., RCAN1.1 protein), but no 28 kDa RCAN1.4 protein band, was detected by this antibody (data not shown). Again, this data indicated that RCAN1.1 is likely the major isoform of RCAN1 proteins expressed in IMR-32 cells. At 6 hours treatment, the three selenium compounds did not significantly alter RCAN1.1 protein levels (data not shown). However, at 24 hours treatment, Compounds C and Compound D (but not Compound E) caused a decrease of RCAN1.1 protein expression in IMR-32 cells (see FIG. 6B).

Quantitative analysis showed that the decrease of RCAN1.1 protein levels in IMR-32 cells after Compound C or Compound D treatment was significant when compared to control cells (see FIG. 6C). Data were normalized by ACTB protein level in each samples, and are presented. Mean±SEM, n=3. In FIG. 6C, different letters in the bar graphs means a significant difference between those two groups (p value <0.05). Further confirming the quantitative data, a dose-dependent decrease of RCAN1, more specifically, RCAN1.1 mRNA expression was also observed in IMR-32 cells that were stably transfected with control siRNA lentiviruses and treated with Compound C (see FIGS. 14B-14C).

These results indicate that Compound C and Compound D are downregulators of RCAN1 (more specifically RCAN1.1) at both the mRNA and protein level, and thus may inhibit Tau hyperphosphorylation in AD brains, improve MT function against oxidative stress, and ameliorate anxiety.

Compound C: A Downregulator of the Major Late-Onset AD Risk Factor APOE4 Protein Likely Through the Inhibition of the Expression of its Upstream Transcriptional Factor PPARG It is well documented that the APOE4 allele (encoded from the APOE gene) is a major late-onset AD risk factor. PPARG is a transcription factor that can induce APOE transcription. Thus, it is possible that selenium compounds such as Compound C may downregulate PPARG protein expression, eventually leading to inhibition of the expression of the late-onset AD risk factor APOE4.

To explore this possibility, IMR-32 cells were treated with 150 ppb Compound C, Compound D or Compound E (150 ppb) for 6 hours and 24 hours, and then subjected to Western blot and QRT-PCR analyses. As shown in FIG. 7A-B, PPARG protein expression was markedly attenuated by Compound C or D after 6 hours of treatment. In agreement with these observations, PPARG mRNA levels were also significantly lower in IMR-32 cells after treatment with Compound C or Compound D for 6 hours (FIG. 7C). Therefore, Compound C and Compound D are downregulators of PPARG in IMR-32 cells at both mRNA and protein levels.

More importantly, the protein levels of APOE4, a late-onset risk factor for AD, were markedly decreased in IMR-32 cells after treatment with Compound C for 24 hours (FIG. 7D-E), but not for 6 hour (data not shown). In agreement with reduced APOE4 protein expression in IMR-32 cells after Compound C treatment for 24 hour, APOE mRNA levels were also significantly decreased when compared to control group (FIG. 7F). Compound D did not affect APOE4 protein expression (FIG. 7D-E) even though it did cause a decrease in PPARG expression (FIG. 7A-C), indicating that there exists an unknown, Compound D-specific target factor(s) which may compromise PPARG-mediated APOE expression. Data suggests that Compound C is a downregulator of the late-onset risk factor APOE4.

It should be emphasized that the downregulation of PPARG proteins by Compound C occurred at 6 hours of treatment (FIG. 7A-B) while APOE4 protein downregulation by Compound C occurred at a later point of time (FIG. 7D-E). Based on the above findings, it is likely that Compound C first inhibits PPARG expression and subsequently attenuates the expression of APOE4 protein in IMR-32 cells. Regardless, the data provide evidence that Compound C likely will have beneficial effects against late-onset AD via the downregulation of APOE4 protein expression.

Compound C, an Enhancer of Gluconeogenesis (Likely Through Modulation of Insulin/IGF Receptors) in IMR-32 Cells There has been a rapid growth in the literature supporting the idea that AD originates from impaired glucose import and defective energy metabolism in the brain (reviewed by de la Monte and Wands, 2008). Extensive disturbances in brain insulin and Insulin-like Growth Factor (IGF)-signaling mechanisms can account for a number of the molecular, biochemical, and histopathological effects seen in AD. Glucose-6-Phosphatase Catalytic subunit (G6PC) is a key FOXO target for gluconeogenesis in the liver. FOXO phosphorylation is modulated by Insulin/INSR (Insulin Receptor) and IGF1/IGF1R (Insulin like Growth Factor Receptor) signaling.

Although the importance of gluconeogenesis (new glucose production) as a source of energy for neuronal cells is not clear, several studies in the literature report gluconeogenic capability in many brain areas. It is well known to those skilled in the art that G6PC is the critical control point for regulating gluconeogenesis in tissues. It has been reported that lower brain glucose metabolism is present before the onset of clinically-measurable cognitive decline in two groups of people at risk of Alzheimer's disease (AD)—carriers of ApoE4, and in those with a maternal family history of AD, and that brain hypometabolism likely precedes and contributes to the neuropathological cascade leading to cognitive decline in AD (Cunnane et al, Nutrition, 2011; 27:3-20). Thus, it is possible that selenium compounds may play a role in regulating Glucose-6-phosphatase, catalytic subunit (G6Pc) expression to improve glucose production against hypometabolism in some AD patients.

Thus, IMR-32 cells were treated with 150 ppb of Compound C, Compound D or Compound E for 24 hours, and then subjected to Western blot analysis as described herein. As shown in FIG. 8A, G6Pc protein levels were visibly increased in IMR-32 cells treated with Compound C.

Quantitative analysis showed there was about a 3-fold increase of G6Pc protein expression levels after treatment with Compound C. A similar increase was not observed in cells treated with Compounds D or E (see FIG. 8B). Mean±SEM, n=3. In FIG. 8B, different letters in the bar graphs means a significant difference between those two groups (p value <0.05).

To examine whether or not Compound C can regulate INSR/IGF1R signaling in IMR-32 cells, QRT-PCR analysis was performed to measure INSR and IGF1R mRNA levels. As shown in FIGS. 8C and 8D, INSR and IGF1R mRNA expression levels, respectively, were downregulated by both doses of Compound C after 24 hours of treatment. Mean±SEM, n=4. The * refers to a p value <0.05 when compared to the control group (0 ppb).

These results indicate that Compound C can likely modulate Insulin/IGF1 signaling and G6Pc expression to enhance gluconeogenesis in brain cells which may be beneficial for the survival of brain cells in AD.

Example 6

Compound C, a FOXO4 Activator in IMR-32 Cells

The Forkhead Box class 0 gene (FOXO) proteins are a family of key nuclear transcription factors having diverse roles in cell proliferation, differentiation, and longevity. They partially control key functions in the cell, such as gluconeogenesis (glucose production from non-carbohydrate substrates). Their entry into the cell nucleus is controlled by phosphorylation; phosphorylated FOXO is excluded from the nucleus while dephosphorylated FOXO can enter. Accordingly, Compound C, Compound D and Compound E were studied to determine if they could influence the expression of these potent signaling factors. Of the three main FOXO proteins, abundant FOXO4 protein was present in IMR-32 cells, while FOXO1 and FOXO3 proteins were barely detectable by their specific antibodies (data not shown).

Treatment with Compound C, Compound D, or Compound E for 6 hours caused a decrease in the phosphorylation of FOXO4 (pFOXO4) in IMR-32 cells (see FIGS. 9A and 9B). After 24 hours of treatment, decreased pFOXO4 Threonine 28 (T28) levels were observed in cells treated with Compound C and Compound E, but not Compound D-treated IMR-32 cells. (see FIGS. 9A, and 9C).

Quantitative analysis showed that the decrease in pFOXO4 levels in IMR-32 cells by Compound C, Compound D, and Compound E during the 6 hours treatment, and by Compound C and Compound E for the 24 hour treatment, was statistically significant (see FIGS. 9B-9C). Mean±SEM, n=3. In FIG. 9B-9C, different letters in the bar graphs means a significant difference between those two groups (p value <0.05).

It is important to note that none of the individual compound treatments brought about any change in total FOXO levels (see FIG. 9A), but rather changed the control of FOXO4 by causing its dephosphorylation. Reduced FOXO4 phosphorylation was unlikely due to the downregulation of AKT phosphorylation, as pAKT protein levels were not visibly decreased in Compound C-, Compound D-, or Compound E-treated cells (see FIG. 9A).

It is well characterized that dephosphorylation of FOXOs, such as FOXO4 at the T28 (threonine 28) site, leads to nuclear localization of FOXO proteins. This result suggests that the compounds described herein likely will enhance nuclear FOXO4 action. This data suggest that Compound C and Compound E are FOXO4 activators, while Compound D can also regulate FOXO4 via dephosphorylation.

Expression of phosphorylated FOXO1/3/4 in a non-neuronal mouse AML-12 liver cell line was examined Tests were performed at the same time and under the same experimental conditions as the human IMR-32 cells. It was found that treatment of Compound C at 150 ppb for 6 hours and 24 hours did not affect the phosphorylation of FOXO3 in AML-12 cells while pFOXO4 protein was barely detected under these experimental conditions (data not shown).

Certain FOXO proteins in the nucleus can lead to a potent activation of gluconeogenesis (glucose production through the stimulation of G6Pc expression). While such a situation would be undesirable in, say, the liver of a diabetic subject, it could be viewed as extremely favorable in the situation of a subject in early stage AD—where glucose import into the neuron is impaired and, consequently, the brain cell is starved of its primary fuel source. An enhanced ability to produce glucose from the carbon skeletons of other molecules would be very beneficial in such circumstances. Enhanced expression of G6Pc (FIG. 8A), a well-characterized FOXO target, further supports the notion that Compound C is a FOXO4 activator in IMR-32 cells and that it increases gluconeogenesis in these cells.

FOXO4, a Critical Molecule for Cell Survival in IMR-32 Cells

FOXO4 was the most abundant protein of the three FOXO family members expressed in IMR-32 cells (data not shown), and its phosphorylation was inhibited by three selenium compounds as shown in FIGS. 9A-9C. To gain insights into the function of FOXO4 in IMR-32 cells, stable FOXO4 knock-down (KD) cells using FOXO4-specific siRNA lentiviruses were generated. After short-term selection with puromycin (to select the positively transfected FOXO4 siRNAs) in transfected IMR-32 cells, a portion of these transfected cells was subjected to QRTPCR analysis of FOXO4.

As shown in FIG. 10A, FOXO4 mRNA levels were reduced almost 4-fold in FOXO4 KD cells. These results confirm that FOXO4 KD cells had successfully been generated. Mean±SEM, n=4. The * refers to a p value <0.05 when compared to the control group (0 ppb).

Continued culture of these FOXO4 KD cells in puromycin-containing media resulted in noticeable cell death following 4 weeks of culture. In fact, after 48 days of continuous culture, the majority of these FOXO4 KD cells were dead, while control cells (stably transfected with control siRNA lentiviruses) remained healthy (see FIG. 10B-10C).

These results suggest that prolonged culture of FOXO4 KD cells caused a progressive loss of cell viability and that FOXO4 is required to maintain the viability of IMR-32 cells.

These results establish the cellular importance of FOXO4 in the cell survival of human neuronal cells. The above discovered inhibition of FOXO4 phosphorylation by Compound C likely will lead to increased FOXO levels in the nuclei and overall improvements in brain cell survival.

FOXO4 is an Essential Molecule for Compound C to Stimulate MT Potential, and to Inhibit the Expression of Genes Relating to AD Pathogenesis Compound C is a MT stimulator that can enhance MT potential in IMR-32 cells (FIGS. 2A-2K). This is likely due to the stimulation of PGC1a and/or downregulation of UCPs by Compound C (FIGS. 2A-2K). In addition, Compound C also inhibits FOXO4 phosphorylation (FIGS. 9A-9C). Bioinformatic analysis showed that one or more FOXO binding motif(s) is present in the promoter of PGC1α and UCP2 genes (data not shown). It is possible that Compound C may act via inhibition of FOXO4 phosphorylation to enhance MT function. FOXO4KD cells and normal control KD cells were cultured in serum-containing media, treated with two doses (75 ppb and 150 ppb) of Compound C for 6 hours, and subjected to MT potential assays.

Compound C treatment significantly enhanced MT potential in normal control cells cultured with serum (see FIG. 11A). However, in FOXO4KD cells, there was no significant effect on MT potential following Compound C treatment (see FIG. 11A). To exclude the possibility that unknown factors in sera may affect the action of Compound C in cultured IMR-32 cells, cells were cultured in serum-free media for 24 hours, treated with Compound C (diluted in serum-free media) for 6 hours, and then subjected to MT analysis. Data were normalized by the fluorescence intensities of stained cell nuclei. Mean±SEM, n=8. The * refers to a p value <0.05 when compared to the control lentiviral KD cells group (0 ppb).

As shown in FIG. 11B, MT potential in normal control cells cultured without serum was also significantly stimulated by Compound C, albeit to a lesser degree than normal cells cultured in serum-containing media. More importantly, there was no significant increase of MT potential in FOXO4KD cells after either dose of Compound C treatments. These results demonstrate that FOXO4 is involved in the stimulation by Compound C of MT potential in IMR-32 cells. These results demonstrate that FOXO4 is required for Compound C to stimulate MT potential likely through the upregulation of PGC1a and downregulation of UCP proteins in IMR-32 cells.

FOXO4 is Essential for Compound C in IMR-32 Cells to Inhibit the Expression of NICASTRIN, GSK3B and APOE: Key Genes for Early and Late-Onset AD Expression of genes such as Nicastrin and GSK3B (FIGS. 3A, 3C, 3G-3I, 4A, 4F-4H) which are associated with early-onset AD pathogenesis was attenuated by Compound C. Also Compound C caused a decrease of phosphorylation of FOXO4 (FIGS. 9A-9C), likely leading to a significant increase of nuclear FOXO4 and altered gene transcription. Bioinformatic studies revealed that one FOXO binding motif is present in the Nicastrin gene promoter and five FOXO binding motif(s) are present in the human GSK3B (but not the mouse Gsk3b promoter). Therefore, GSK3B and Nicastrin likely are two direct downstream target genes of FOXO4 in neuronal cells in humans. FOXO4 knockdown KD cells and control cells were treated with Compound C (75 ppb and 150 ppb) for 24 hours and subjected to QRT-PCR analysis of these two early-onset AD genes key for plaque and tangle formation.

As shown in FIG. 12A, Nicastrin expression was inhibited by Compound C in control cells, but not significantly altered in FOXO4KD cells. Similarly, GSK3B expression was attenuated by Compound C in control cells but not in FOXO4KD cells (FIG. 12B). Therefore, the results suggest that FOXO4 is essential for Compound C to downregulate the expression of these two key early-onset genes in IMR-32 cells. It should be noted that there is no FOXO binding motif on the mouse Gsk3b promoter.

Protein levels of APOE4 (a late-onset AD risk factor) and its potential upstream transcription regulator PPARG were downregulated by Compound C in IMR-32 cells (FIGS. 7A-7F). The downregulation of PPARG proteins by Compound C occurred at 6 hour treatment (FIG. 7A-B) when reduced FOXO4 phosphorylation was also observed (FIGS. 9B-9C) while APOE4 protein downregulation by Compound C occurred at a later point of time (FIG. 7D-E). Bioinformatic analysis showed that the human APOE promoter does not contain FOXO binding sites but has five PPARG binding motifs (data not shown). Furthermore, sixteen FOXO binding motifs are presented in the PPARG promoter region. PPARG is a transcription factor that can induce APOE transcription. In non-brain cells, it has also been reported that FOXOs can inhibit PPARG transcription. Thus, it is possible that selenium compounds such as Compound C, through inhibition of FOXO phosphorylation, may downregulate PPARG protein expression, subsequently leading to inhibition of the expression of a major late-onset risk factor APOE4.

To further investigate whether Compound C can regulate transcription of PPARG and its downstream target APOE in a dose-dependent manner, and whether FOXO4 is required for Compound C to regulate transcription of these two genes, normal control cells and FOXO4 KD cells were treated with two doses of Compound C for 24 hours, and subjected to QRT-PCR analysis. As shown in FIG. 12C-D, PPARG and APOE mRNA levels in control normal cells were attenuated in IMR-32 cells after treatments with both doses (75 ppb and 150 ppb) of Compound C. These results are consistent with their reduced protein expression observed in Compound C-treated IMR-32 cells (FIGS. 7B, 7E), which confirms that Compound C can regulate the expression of PPARG and its potential downstream target and the key late-onset AD risk gene APOE. In FOXO4KD cells, unlike control cells, PPARG or APOE expression was not significantly altered by Compound C treatment (FIG. 12C-D). Compound C can inhibit both PPARG and APOE transcription and that FOXO4 is essential for Compound C action in this process.

Compound C may target FOXO4 to downregulate PPARG expression, and subsequently, inhibit APOE mRNA and APOE4 protein expression. The latter event is likely PPARG-dependent. Regardless, these data suggest that Compound C acts through FOXO4 to control the expression of PPARG and APOE4 protein.

FOXO4 is Essential for Compound C in IMR-32 Cells to Inhibit the Expression of all Four p38-Coding Genes: Key Genes for Tauopathy and Inflammation in AD In addition to GSK3B, p38 kinases play a role in Tau phosphorylation and NFT formation. Furthermore, it has been reported that Aβ plaques cause activation of p38, resulting in enhanced cytokine production and inflammation in AD. Thus, inhibition of p38 activity or downregulation of p38 expression may be beneficial against AD pathogenesis and inflammation.

As previously shown, treatment with Compound C caused a significant decrease in total p38 protein in IMR-32 cells (see FIG. 5B). In mammals, MAPK 14, 11, 12, and 13 genes encode for p38-α, -β, -γ and -δ protein isoforms, respectively. The reduced p38 protein levels in Compound C-treated IMR-32 cells (FIG. 5B) could be due to the inhibition of one or more MAPK gene(s). In addition, bioinformatic analysis revealed that there are eight consensus PPARG and one FOXO binding motifs on the MAPK11 promoter, four consensus PPARG and one FOXO binding motifs on the MAPK12 promoter, and two consensus PPARG motifs on the MAPK13 promoter. Several non-consensus FOXO binding motifs (with 1- or 2-mismatched nucleotide(s)) are also present on the MAPK13 and MAPK14 gene promoters (data not shown). Therefore, it is possible that Compound C may inhibit the transcription of one or more MAPK genes resulting in reduced levels of p38 total protein. This effect may be dependent on FOXO and/or its target PPARG in IMR-32 cells (as discussed above).

Normal control cells and FOXO4KD cells were incubated with two doses of Compound C for 24 hours, and subjected to QRT-PCR analysis of the MAPK11-14 genes. The relative mRNA expression of all four MAPK genes in normal control IMR-32 cells was assessed. As shown in FIG. 13A, the genes having the highest to lowest relative expression in IMR-32 cells is as follows: MAPK14 had the highest mRNA levels, followed by MAPK12, MAPK11, and MAPK13. Data in Compound C-treated control and FOXO4 KD cells were normalized by their levels in control and FOXO4KD cells, respectively. Mean±SEM of indicated number of samples in the bar graphs. The * in FIGS. 13B-13E refers to a $P<0.05$ when compared to control cells with vehicle treatment (0 ppb).

Compound C was tested to see if it could regulate the transcription of these four genes. Normal control KD cells were treated with 75 ppb and 150 ppb Compound C for 24 hours (see FIGS. 13B-13E). A significant decrease of MAPK11 and MAPK12 mRNA levels were observed in the control cells treated with 75 ppb of Compound C, and a trend towards decreased MAPK13 and MAPK14 mRNA levels.

In addition, the mRNA levels of all four MAPK genes were significantly decreased in control cells after treatment with Compound C at the 150 ppb dose (see FIG. 13B-13E). These results confirm that Compound C can indeed inhibit the expression of all four MAPK genes, at both mRNA and protein levels. These results are also consistent with the observation of reduced total p38 protein levels in Compound C-treated IMR-32 cells (see FIG. 5B).

Finally, the role of FOXO4 in Compound C-mediated inhibition of MAPK gene expression was investigated. As shown in FIGS. 13B-E, none of the mRNA levels of the four MAPK genes in FOXO4KD cells were significantly altered by Compound C treatments at 75 ppb and 150 ppb doses. Therefore, inhibition of the expression of all four MAPK genes in IMR-32 cells by Compound C is dependent on FOXO4. FOXO4 is essential for Compound C to downregulate the expression of all four MAPK genes in IMR-32 cells, leading to a significant decrease in total protein levels and the potential for reduced tangle formation and inflammation in AD brain as a result.

FOXO4 is Essential for Compound C in IMR-32 Cells to Inhibit the Expression of RCAN1: A Key Gene for Tauopathy, MT Function and Anxiety RCAN1 plays critical roles not only in Tau phosphorylation and MT function, but also in the expression of anxiety in the brain. In mammals, there are two RCAN1 protein isoforms, RCAN1.1 and RCAN1.4 encoded from its respective transcript (see FIG. 14A). The transcription of RCAN1.4 is controlled by NFAT transcriptional factors, the regulators of RCAN1.1 transcription remain largely unknown.

Previous studies described herein demonstrated that RCAN1.1 protein levels were significantly downregulated by Compound C in IMR-32 cells (see FIG. 6B). These results also revealed that Compound C can target FOXO4 in IMR-32 cells (see FIGS. 9A-9C). Bioinformatic studies also confirmed that the gene transcripts RCAN1.1 and RCAN1.4 differ in that RCAN1.1 promoter comprises a conserved FOXO binding motif, but the RCAN1.4 promoter does not (see FIG. 14A). Therefore, it is possible that Compound C may inhibit the transcription of RCAN1.1 in a FOXO4-dependent manner, resulting in a decrease of RCAN1.1 protein that could affect Tau phosphorylation, MT dysfunction, and anxiety.

To investigate whether Compound C can regulate transcription of RCAN1 in a dose-dependent and FOXO4-dependent manner, normal control cells and FOXO4 KD cells were treated with two doses of Compound C for 24 hours, and subjected to QRT-PCR analysis. First a specific RCAN1 Taqman probe that can recognize all RCAN1 mRNA isoforms was used to determine if Compound C can regulate the transcription of RCAN1. It was found that total RCAN1 mRNA levels in control normal cells were significantly attenuated in IMR-32 cells after treatments with both doses of Compound C (FIG. 14B). However, in FOXO4KD cells, unlike control cells, total RCAN1 mRNA levels were not significantly altered by Compound C treatment (FIG. 14B). These results suggest that Compound C can inhibit the transcription of RCAN1 in a dose-dependent and FOXO4-dependent manner.

To further determine whether Compound C can regulate the transcription of RCAN1.1 mRNA, the above Compound C-treated RNA samples were subjected to QRT-PCR using a specific RCAN1.1 mRNA Taqman probe. As shown in FIG. 14C, RCAN1.1 mRNA expression was inhibited by Compound C at the dose of 150 ppb, which is consistent with reduced RCAN1 protein expression observed in Compound C-treated IMR-32 cells (FIG. 6C). Similar to total RCAN1 mRNA, RCAN1.1 mRNA expression in FOXO4KD cells was not significantly affected by Compound C (FIG. 14C). In addition, we also performed QRT-PCR using a specific RCAN1.4 mRNA probe on the above RNA samples, and did not detect RCAN1.4 transcripts, which is consistent with the lack of 28 kDa RCAN1.4 protein expression in normal IMR-32 cells by Western blots (data not shown).

Together the results demonstrate that Compound C can inhibit RCAN1, more specifically, RCAN1.1 expression in a dose-dependent manner, and that FOXO4 is essential for Compound C to downregulate the expression of RCAN1 in IMR-32 cells, leading to a decrease in RCAN proteins and the potential for reduced tangle formation and improved MT function in AD subjects together with a general potential for reduced anxiety or depression in treated subjects suffering from these disorders.

In short, FOXO4 is an important molecule for Compound C not only in the stimulation of MT function (indicated by MT potential, FIGS. 11A-11B) but also in the inhibition of the expression of a variety of genes such as Nicastrin, GSK3B, APOE, MAPK11-14 and RCAN1.1 (FIGS. 12A-12D, 13A-13E, 14A-14C) key for AD pathogenesis and inflammation. The enhanced MT function brought about by Compound C is likely mediated through the stimulation of PGC1a and the inhibition of UCP2/3 in a FOXO4-dependent manner, as these MT genes are known to be FOXO target genes in other tissues. As FOXO4 is an important molecule for human neuronal cell survival (FIGS. 10A-10C), Compound C has therapeutic potential for the treatment of AD and AD-associated MT disorders due to its unique ability to enhance MT function and to inhibit AD pathogenesis.

Discussion

The results indicate that Compound C has potential as a preventative or treatment for Alzheimer's disease (AD). For the purpose of this discussion we describe AD as either "early-onset", i.e. due to mutations in genes controlling plaque formation, or the much more common "late-onset" AD, e.g. such as the type associated with the risk factor APOE4 allele. Compound D and Compound E may also have a role to play against AD processes by, for example, attenuating p38, RCAN1 and/or Tau protein expression or phosphorylation.

It was found that FOXO4 is required for maintaining the viability of IMR-32 cells (FIG. 10B-10C) and is essential for Compound C to enhance MT potential (FIGS. 11A-11B). The latter is likely mediated through the FOXO4-dependent stimulation of PGC1a, and inhibition of UCP2 and UCP3 in IMR-32 cells, considering that these MT functional genes are known to be FOXO target genes in other tissues. Besides, FOXO4 may also be required for Compound C to enhance glucose production in the brain cells, since G6Pc is an established FOXO target gene in the process of gluconeogenesis. In addition, a number of other genes associated with late-onset AD (Acta Neuropathol. 2012; 124(3): 305-323) such as ATXN1, GAB2, ABCA7, BIN1 and CR1 also contain one or more FOXO-binding motifs in their gene promoter regions (data not shown). As such, Compound C may also directly or indirectly influence the expression of these genes through the FOXO transcription factor family, especially FOXO4.

Example 7

Compound C, was tested in the APP/PS1 mouse model of AD. Effects of feeding Compound C to mice on β amyloid plaque deposition and gene expression in the brain were measured.

Materials and Methods

Animals

Male APPΔNLh/ΔNLh×PS1P246 L/246 L knock-in model mice of Alzheimer's disease (abbreviated APP/PS1) were genotyped using standard primers for human APP (Amyloid Precursor Protein) and human PS1 (PSEN1). These APP/PS1 mice starting at the age of 6 months, were fed either a control diet containing normal levels of selenium (0.3 ppm from plant and inorganic selenium salt sources) or an experimental diet containing Compound C (the control diet to which was added 1 ppm Se from Compound C) for 6 months.

At 12 months of age, the mice were euthanized and the brains quickly removed, the cerebellum isolated and the hemispheres snap-frozen in liquid nitrogen and then stored at −80° C. for further immunohistochemistry (IHC), protein and RNA analysis. All procedures conducted on these animal studies were pre-approved by the University of Kentucky IACUC committee.

IHC Analysis of Amyloid Deposits in the Brains of APP/PS1 Mice

Frozen brain tissues were sectioned using a Leica-CM1900 cryostat (Leica Microsystems Inc., Bannockburn, Ill.), as described previously (Zhang et al, 2008. Biochem Biophys Res Commun). These frozen brain sections were subjected to immunohistochemistry staining of Aβ plaques using a specific polyclonal antibody against Aβ1-42 (Abcam) and the Rabbit ImmunoCruz Staining System (Santa Cruz Biotechnology, Santa Cruz, Calif.) according to the manufacturer's protocol. Sections from at least 3 animals per control or Compound C-treatment group were examined.

ELISA Analysis of Insoluble [Formic Acid (FA)-Soluble] Aβ1-42 Levels in the Brains of APP/PS1 Mice Frozen hemispheres of control- and Compound C-treated APP/PS1 mice were weighed and homogenized in PBS buffer. Insoluble Aβ fractions (formic acid (FA)-soluble fractions) were extracted from the homogenates using standard serial extraction protocols as described previously (Lovell et al, Free Radic Biol Med 2009; 46:1527-33) Insoluble $A\beta_{1-42}$ levels (in the FA soluble fraction) were determined using standard sandwich ELISAs (Invitrogen), according to the manufacturer's procedure.

Western Blot Analysis

Frozen hemispheres of control- and Compound C-treated APP/PS1 mice were weighed and homogenized in PBS buffer, and then subsequently extracted with RIPA buffer (Sigma) containing complete proteinase and phosphatase inhibitors (Fisher Scientific). Protein levels in the samples were determined by micro-BCA protein analysis according to the manufacturer's protocol. Aliquots (20 to 25 µg) of protein were separated on 4-20% SDS-PAGE gels, transferred to nitrocellulose or PVDF membranes, and probed with specific antibodies against BACE1 (Cell Signaling), Neprilysin, Insulin Degrading Enzyme (IDE) (Abcam), phosphorylated-p38 (Cell Signaling), Ionized Calcium binder Adaptor Molecule 1 (Iba-1) (Abcam), phosphorylated Foxo3 (Cell Signaling), phosphorylated Foxo4 (Cell Signaling) and Actb (Cell signaling), as reported previously (Reddy, Liu et al. 2008 Science). Positive signals on the membrane blots were detected using Amersham's enhanced chemiluminescence Western Blotting Prime Detection reagents (GE healthcare Lifescience, Pittsburgh, Pa.). Images of these luminescence signals on the membrane blots were captured using the LI-COR Odyssey Fc Image system (Lincoln, Nebr.). Protein band densities in Western blots were determined using NIH Image J software, and then normalized by Actb levels in each samples to obtain the protein levels.

Total RNA Extraction

Approximately 10 mg brain sample was homogenized with a Qiagen TissueRuptor (Qiagen, Valencia, Calif.) and total RNA was extracted using an RNeasy Mini kit (Qiagen), following the protocol recommended by the company. To remove contaminating DNA, on-column DNA digestion with RNase-Free DNase (Qiagen) was performed. Integrity and purity of isolated RNA was assessed using a NanoDrop ND-1000 spectrophotometer (Thermo Scientific, Wilmington, Del.) and further confirmed with an Agilent 2100 Bioanalyzer System (Agilent Technologies, Santa Clara, Calif.).

Microarray Procedures cRNA preparation, hybridization and scanning were performed following the standard protocols recommended by Affymetrix (Santa Clara, Calif.). Briefly, purified RNA was used for biotin-labeled cRNA synthesis using the Affymetrix GeneChip Expression 3'-Amplification One-Cycle Target Labeling Kit (Affymetrix), according to the manufacturer's recommended procedures. Labeled cRNA was hybridized to mouse genome MG-430_2.0 GeneChip arrays (Affymetrix) for 17 hours at 45° C., followed by washing, streptavidin-phycoerythrin (SAPS) staining and finally scanning in an GeneChip Scanner 3000 7G (Affymetrix). Probe signal intensities were analyzed using an Affymetrix MASS algorithm scaled to the default trimmed mean signal intensity (SI) of 500. A total of 11 mouse gene expression profiles, five from control-treated and six from Compound C-supplemented animals were obtained.

Microarray Data Analysis

GeneSpring GX 13.0 (Agilent) software was used to validate and normalize microarray data and to perform statistical and gene expression pattern analyses. Briefly, normalization was done by first scaling the intensity of probesets of the arrays to a mean target intensity of 500, followed by baseline transformation to median of all samples. Background corrections were done by MASS based on the Perfect Match (PM) and Mis-Match (MM) probe design of the microarray. To minimize the possibility of misleading findings, probe sets with low signal intensity and those which were labeled as 'Absent' by the MASS algorithm across samples were excluded from further analysis. The differentially expressed genes by age or diets were filtered using the volcano plot method where genes with P<0.05 and corresponding signal intensity fold change (FC) >1.2 or FC<−1.2 were deemed to be significantly different.

Ingenuity Pathways Analysis (IPA) Analysis of Microarray Data

To dissect the biological themes represented by altered transcription profiles, genes significantly regulated by Compound C were further grouped into networks, functions and canonical pathways using Ingenuity Pathways Analysis software (IPA, Ingenuity Systems, Redwood City, Calif.). Downstream effects analysis was performed to predict the effect of gene expression changes in the dataset on biological processes and disease or on toxicological functions. Fischer's exact test was used to determine the significance of the association between the genes and the given network, biological function or canonical pathway.

QRT-PCR Analysis

RNA samples were subjected to real-time PCR analysis using the Applied-Bioscience's RT kit and predesigned Taqman probes (Invitrogen), as described previously (Lan et al EMBO J 2003). Three to six samples were analyzed in each group. Data were normalized by Actin B (Actb) levels in each sample, and are presented as mean±SEM of 3-6 samples.

Statistical Analysis

If applicable, a Student's t-test was performed to determine the statistical difference between two groups. P values less than 0.05 were considered significant.

Results and Discussion:

Attenuated Amyloid Plaque Deposits in APP/PS1 Mice, an Alzheimer's Disease Mouse Model, Following Compound C Treatment This example was to test whether Compound C will provide protective effects against amyloid pathology in vivo by reducing the levels of plaque-specific beta amyloid and/or by modulating molecular mechanisms associated with amyloid plaque formation and/or degradation. For this purpose, the APPΔNLh/ΔNLh×PS1P246 L/246 L knock-in mouse model of amyloidosis (APP/PS1) was employed.

Male mice were genotyped using standard primers for human APP (Amyloid Precursor Protein) and human PS1 (PSEN1). APP/PS1 mice develop small numbers of amyloid deposits without neurites by 6 month of age with increased deposition or aggregation over the next nine months. The recalcitrant amyloid protein at the center of amyloid plaques is referred to as Formic Acid (FA)-soluble (FA-soluble Aβ1-42), since it is resistant to solubilization by buffers, such as PBS or SDS, but can be fully solubilized in 70% FA solution. Quantification of FA soluble (aggregated) Aβ1-42 as a function of age in mice maintained on a control diet shows a significant increase in levels of FA-soluble $A\beta_{1-42}$ beginning at 6 month of age with pronounced increases evident at 12 month of age. Thus, this model recapitulates many of the features of Aβ pathology in AD with an age related increase in aggregated AP.

APP/PS1 mice were fed either a control diet (N=10) containing normal levels of selenium (e.g., 0.3 ppm from plant and inorganic selenium salt sources) or an experimental diet (N=11) containing Compound C (the control diet to which was added 1 ppm Se from Compound C) from 6 to 12 months of age.

Following treatment, mouse brain tissues were dissected, frozen, sectioned, and then subjected to immunohistochemistry (IHC) staining (see FIGS. 15A-15D). As shown in FIG. 15A, there were many Aβ plaque deposits (indicated by strong staining of Aβ1-42) present in the cortical regions of APP/PS1 mice after feeding with the control diet. However, much fewer and/or weaker-staining amyloid plaque deposits were presented in the brain cortex of APP/PS1 mice after Compound C treatment (FIG. 15B). As shown in FIG. 15C, there were also many Aβ plaque deposits (indicated by strong staining of Aβ1-42) present in the hippocampal regions of APP/PS1 mice after feeding with the control diet. However, much fewer and/or weaker-staining amyloid plaque deposits were presented in the brain hippocampus of APP/PS1 mice after Compound C treatment (FIG. 15D).

To further confirm this observation, brain tissues were homogenized and extracted with FA to obtain FA-soluble fractions, and these FA-soluble fractions of each animal tissue was subjected to Enzyme-Linked Immunosorbent Assay (ELISA) to determine the levels of insoluble Aβ1-42 which represents the recalcitrant amyloid protein at the center of amyloid plaques. As shown in FIG. 15E, FA-soluble Aβ1-42 levels were significantly reduced (about 30% reduction) in the brains of APP/PS1 mice after the treatments of Compound C when compared to control mice. Therefore, Compound C can inhibit the plaque load and Aβ1-42 deposition in the brains of APP/PS1 mice.

To further investigate the molecular mechanism of Compound C in the inhibition of plaque deposition and Aβ1-42 levels, Western blot analysis was performed and the levels of several proteins responsible for Aβ production and degradation (for instance, BACE1 (beta-secretase) for plaque formation, Neprilysin and IDE (insulin degrading enzyme) for plaque degradation) were determined. As shown in FIG. 15F, BACE-1 protein levels were decreased in the brains of APP/PS1 mice fed with the Compound C diet. In contrast, IDE and Neprilysin protein levels were elevated in the brains of Compound C-treated APP/PS1 mice. Since BACE1 is critical for Aβ formation, and IDE and Neprilysin for AP degradation, the results suggest that Compound C inhibits Aβ production and stimulates Aβ clearance in APP/PS1 mouse brains.

To further investigate if Compound C can enhance Neprilysin expression at the mRNA level, we performed microarray analysis and found that Neprilysin (Mme) RNA levels were elevated in APP/PS1 mouse brains (about 2-fold increase by microarray, see Table 3). To confirm this, quantitative RT-PCR was performed to examine Neprilysin mRNA expression in Compound C-treated APP/PS1 mice. As shown in FIG. 15G, and Neprilysin mRNA levels were increased (about 1.6 fold) in the brains of APP/PS1 mice after Compound C treatment when compared to control mice. Together, the results suggest that Compound C stimulates Neprilysin expression at both mRNA and protein levels and this stimulation may promote Aβ clearance.

Based on the studies in human IMR32 cells described earlier, Compound C can regulate p38 kinase activity in the brain to inhibit Tau hyperphosphorylation and subsequent tangle formation, together with Aβ1-42-induced inflammation. Thus, Western blot analysis was performed to examine the protein levels of phosphorylated-p38 (the active form of p38) and Iba-1, a marker of neuroinflammation (microglial activation) in the brains of control- and Compound C-treated APP/PS1 mice. As shown in FIG. 15H, both phosphorylated-p38 and Iba-1 protein levels were decreased in Compound C-treated APP/PS1 mice. Since p38 is critical for Tau hyperphosphorylation in tangle formation in AD, Compound C likely will inhibit Tau hyperphosphorylation in vivo. In addition, Compound C may likely play a role against Aβ1-42-induced neuroinflammation in APP/PS1 mice.

The studies in-vivo demonstrated that Compound C can inhibit plaque deposition in APP/PS1 mouse brains. One action of Compound C in this process is to inhibit Aβ1-42 production through the downregulation of BACE. In addition, Compound C is a stimulator of IDE, and Neprilysin for Aβ clearance. The results also indicate that Compound C likely plays a role in the inactivation of p38.

Microarray and IPA Analyses of Global RNA Expression Profile in the Cortex of Compound C-Treated APP/PS1 Mice Predict the Effects of Compound C Against AD and Other Neurodegenerative Diseases To further investigate the molecular mechanism of Compound C against AD pathogenesis in the brain and to gain information about the role of Compound C in other neurodegenerative disorders or diseases, microarray analysis on RNA samples from the brains of APP/PS1 mice after feeding with control diet (n=5) or Compound C diet (n=6), from 6 to 12 months of age was performed.

Compound C treatments regulated the expression of 2217 genes in the brains of APP/PS1 mice (with a fold change of more than 1.2). This accounts for approximately 10% of all genes included in this microarray. Unsupervised hierarchical clustering (based on both arrays and genes) of these altered gene transcripts were then performed using GeneSpring 13.0 software (Agilent Technologies, Inc.) to determine the expression difference among individual mouse samples of control and Compound C groups.

As shown in FIG. 16, the expression profiles of all 5 control mice were clustered into one group without dramatic difference among each mouse within the control group. Similarly, the expression profiles of all 6 Compound C-treated mice were clustered together. Also, there was no obvious difference among individual mice in the Compound C treatment group. This clustering analysis showed that the expression profiles of control animals were separated from those of Compound C-treated animals. Therefore, the results provide molecular evidence that the oral administration route of Compound C was appropriate for studying the transcriptional effects of this compound in the brains of APP/PS1 mice with minimal variation of their RNA expression profile among each mouse after Compound C treatment.

To better understand the biological themes represented by altered transcription profiles, 2217 genes significantly regulated by Compound C were further grouped into networks, functions and canonical pathways using Ingenuity Pathways Analysis software (IPA, Ingenuity Systems, Redwood City, Calif.). Association analysis demonstrated that a significant portion of Compound C regulated genes are functionally important in neurological functions and disorders. The top three diseases/disorders that are significantly linked to the altered genes by IPA analysis are listed in Table 1. Of the 2217 Compound C-regulated genes, 491, 316 and 160 genes were identified to be functionally connected to neurological diseases, psychological disorders and hereditary disorders, respectively.

TABLE 1

Top three diseases/disorders and biological functions by IPA analysis*

| Functional categories | P-value range[a] | # of molecules |
|---|---|---|
| 1. Neurological Disease | 8.01E−03-3.08E−13 | 491 |
| 2. Psychological Disorders | 7.66E−03-3.08E−13 | 316 |
| 3. Hereditary Disorders | 8.01E−03-3.78E−10 | 160 |

*This analysis is based on IPA's downstream effects analysis which aims to predict the effect of gene expression changes in experiment dataset on biological functions, diseases and disorders.
[a]The p-value of overlap is a measure of the likelihood that the association between a set of genes in the dataset and a related function is due to random association. It was calculated by the Fisher's Exact Test.

Downstream effects analysis aiming to predict the impact of gene expression changes on the biological processes and diseases indicate that Compound C-regulated transcription changes are associated with many major neurodegenerative diseases and related biological processes. As shown in Table 2, Compound C-related transcription changes are functionally pointing to a decreased risk of neuronal disorders, such as loss of neurieis, neurodegeneration of central nervous system or brain, neurodegeneration of brain, disorder of basal ganglia, cell death of cortical neurons and cerebral cortex cells.

In addition, this IPA analysis also predicted Compound C will enhance the survival of neurons (see Table 2). Furthermore, these analyses showed the strong association of Compound C with spatial learning, cognition and brain coordination which is related to general nervous system development (Table 2). Furthermore, these IPA analyses demonstrated a significant connection between Compound C and several major neurological diseases such as Alzheimer's Disease, Parkinson's Disease, Huntington's Disease, even though there was no prediction of activation status of Compound C in these diseases. This could be due to the large number of genes and the functional complexity of those genes involved in the development of these diseases, and the number of altered genes by Compound C revealed in our microarray may not be enough for IPA program to make the prediction of activation status. The results demonstrated that Compound C likely will improve neuronal survival, inhibit neurodegeneration and regulate learning, cognition and coordination which will be beneficial for the treatment of a whole range of neurological disorders.

TABLE 2

Top functional associations between Compound C-regulated genes and neurological diseases, psychotic disorders or behaviors by IPA analysis*

| Disease/disorder subcategory | Diseases or functions annotation | p-Value[a] | Predicted Activation[b] | z-score[c] | Genes regulated |
|---|---|---|---|---|---|
| Neural degeneration, cell survival and cell death | Loss of neurites | 3.51E−03 | Decreased | −2.744 | 9 |
| | Neurodegeneration of central nervous system | 7.55E−04 | Decreased | −2.041 | 23 |
| | Neurodegeneration of brain | 1.41E−03 | Decreased | −2.356 | 22 |
| | Degeneration of brain | 8.21E−04 | Decreased | −2.284 | 25 |
| | Disorder of basal ganglia | 3.08E−13 | Decreased | −2.194 | 161 |
| | Cell death of cortical neurons | 3.94E−04 | Decreased | −2.268 | 33 |
| | Cell death of cerebral cortex cells | 4.30E−03 | Decreased | −2.049 | 38 |
| | Cell viability of neurons | 3.79E−03 | Increased | 2.171 | 37 |
| Cognition, learning behavior and nervous system Development and function | Spatial learning | 3.23E−04 | Not determined | | 35 |
| | Cognition | 7.16E−07 | Not determined | | 89 |
| | Coordination | 3.06E−03 | Not determined | | 37 |
| Major psychological Disorders/neurological diseases | Schizophrenia | 8.51E−10 | Not determined | | 101 |
| | Huntington's Disease | 3.78E−10 | Not determined | | 121 |
| | Parkinson's disease | 6.05E−06 | Not determined | | 47 |
| | Tauopathy | 1.40E−04 | Not determined | | 88 |
| | Alzheimer's disease | 2.25E−04 | Not determined | | 83 |

*This analysis is based on IPA's downstream effects analysis which aims to predict the effect of gene expression changes in experiment dataset on biological processes and disease or on toxicological functions.
[a]The p-value of overlap is a measure of the likelihood that the association between a set of genes in the dataset and a related function is due to random association. It was calculated by the Fisher's Exact Test.
[b]The predicted direction of change for the function, based on the regulation z-score.
[c]A value calculated by the IPA and used to predict the direction of change for the function. Increased predictions are made if z-score is ≥2. Decreased predictions are made if the value is ≤−2. IPA does not make a prediction for the process or disease if z-score between 2 and −2.

Expression Studies of Several Key Genes Against AD and Other Neurodegenerative Diseases A further search of gene markers that are associated to neural development, and the pathologies of Alzheimer's diseases and other neurodegenerative diseases, it was found that the expression of many of those genes dramatically changed in the brain of Compound C-treated APP/PS1 mice. A partial list of these genes is shown in Table 3 (below)

TABLE 3

Gene markers Associated to Neural Development, and the Pathologies of Alzheimer's Diseases or other Neurodegenerative Diseases

| Symbol | Fold Change [a] | Entrez Gene Name |
|---|---|---|
| Mme | 2.02 | membrane metallo-endopeptidase |
| ZIC1 | 3.25 | Zic family member 1 |
| Zic3 | 2.28 | Zic family member 3 |
| Zic4 | 1.75 | Zic family member 4 |
| Zic5 | 1.53 | Zic family member 5 |
| Foxp2 | 2.52 | Forkhead box P2 |
| Drd1 | 4.22 | dopamine receptor D1 |
| Tac1 | 3.36 | tachykinin 1 |
| Sez6 | 1.33 | seizure related gene 6 |
| Penk | 4.068 | proenkephalin |
| Dlx5 | 2.09 | distal-less homeobox 5 |
| Rarb | 4.03 | retinoic acid receptor, beta |
| Meis2 | 2.04 | Meis homeobox 2 |
| Ddx5 | 1.26 | DEAD (Asp-Glu-Ala-Asp) box polypeptide 5 |
| Gpr88 | 6.47 | G protein-coupled receptor 88 |
| Pde10a | 2.91 | phosphodiesterase 10A |
| Akap5 | 1.589 | A kinase (PRKA) anchor protein 5 |
| Isl1 | 11.32 | ISL1 transcription factor, LIM/homeodomain |
| Gpr6 | 9.07 | G protein-coupled receptor 6 |
| Prkcd | 1.813 | protein kinase C, delta |
| Htr2c | 1.797 | 5-hydroxytryptamine (serotonin) receptor 2C, G protein-coupled |
| Gad2 | 1.69 | glutamate decarboxylase 2 (pancreatic islets and brain, 65 kDa) |
| Scarb1 | 1.56 | scavenger receptor class B, member 1 |
| Prkar2b | 1.439 | protein kinase, cAMP-dependent, regulatory, type II, beta |
| Grm4 | 1.418 | glutamate receptor, metabotropic 4 |
| Gabrg1 | 1.375 | gamma-aminobutyric acid (GABA) A receptor, gamma 1 |
| Gabra2 | 1.275 | gamma-aminobutyric acid (GABA) A receptor, alpha 2 |
| Sox2 | 1.274 | SRY (sex determining region Y)-box 2 |
| Sod1 | 1.274 | superoxide dismutase 1, soluble |
| Prdx1 | 1.272 | peroxiredoxin 1 |
| Bcl2 | 1.246 | B-cell CLL/lymphoma 2 |
| Scp2 | 1.204 | sterol carrier protein 2 |
| Pak1 | −1.201 | p21 protein (Cdc42/Rac)-activated kinase 1 |
| Mapt | −1.21 | microtubule-associated protein TAU |
| App | −1.22 | amyloid beta (A4) precursor protein |
| Prnp | −1.256 | prion protein |
| Mapk8 | −1.289 | mitogen-activated protein kinase 8 |
| Apbb1 | −1.293 | amyloid beta (A4) precursor protein-binding, family B, member 1 (Fe65) |
| Prkacb | −1.396 | protein kinase, cAMP-dependent, catalytic, beta |
| Gabra1 | −1.407 | gamma-aminobutyric acid (GABA) A receptor, alpha 1 |
| Sorl1 | −1.41 | sortilin-related receptor, L(DLR class) A repeats containing |
| Nrxn1 | −1.444 | neurexin 1 |
| Rims1 | −1.459 | regulating synaptic membrane exocytosis 1 |
| Cnr1 | −1.492 | cannabinoid receptor 1 (brain) |
| Camk2a | −1.67 | calcium/calmodulin-dependent protein kinase II alpha |

Note:
Function associations are based on Ingenuity knowledge Base (Ingenuity Systems, Redwood City, CA).

Several important genes listed in Table 3 are associated with AD pathologies. For instance, Neprilysin (MME) for plaque clearance, Mapt for tangle formation and APP for Aβ production were significantly altered by Compound C. In addition, genes such as Apbp1, Nrxn1, Sorl1, Camk2a are also involved in AD pathogenesis. It is worth mentioning that Neprilysin (MME) expression was increased by 2-fold by microarray analysis. Mme-knockout mice have both Alzheimer's-like behavioral impairment and significant Aβ deposition in the brain, providing strong evidence for this gene's association with the Alzheimer's disease process. Consistent with the enhanced Neprilysin (MME) mRNA expression revealed by the microarray analysis (Table 3), Neprilysin (MME) expression was indeed significantly elevated (1.6 fold increase) in Compound C-treated APP/PS1 mice by QRT-PCR. (FIG. 15G) Together, this data shows that Compound C is a novel MME enhancer to improve the Aβ clearance against AD.

Zic family genes are critical for brain development and are known to be the genes responsible for Dandy-Walker Malformation in which about 50% of patients have mental retardation and motor defects (Grinberg I et al, NATURE GENETICS VOLUME 36; 2004). There are five Zic family genes (Zic 1, 2, 3, 4 and 5) in mouse and human genomes. Microarray results showed that the expressions of 4 of the Zic genes were significantly elevated in the brains of Compound C-treated mice (Table 3). To validate this, we first examined the relative expression of all five Zic genes in normal mouse brains, and found that all five genes were expressed in the brain with the expression pattern of Zic1>Zic2>Zic3>Zic4>Zic5 (FIG. 17A). Consistent with microarray analysis (Table 3), QRT-PCR analysis confirmed that expression of Zic1, Zic2, Zic3, Zic4 and Zic5 were significantly elevated in the brains of APP/PS1 mice after Compound C treatment (FIG. 17B). Therefore, Compound C may regulate Zic family genes to maintain normal brain development, coordination and mental functions.

Foxp2 is a well-characterized language or speech gene (Lai C S, Fisher S E, Hurst J A, Vargha-Khadem F, Monaco A P. 2001, Nature 413:519-523). Drd1a is a receptor of dopamine which is critical in brain development, learning, behavior such as anxiety and depression (J Neurosci 2010 30:12288-300). It has reported that dopamine receptors are reduced in the temporal lobe of AD patients (J Alzheimer's Dis, 2010; 20:455-75). Tac1 (Tachykinin) is a pain gene and is also associated with Parkinson's disease. Sez6 is a seizure-related gene. Penk is involved in the development of Parkinson's disease. All other genes such as Dlx5, Rarb, Meis Ddx5, Gpr88, Pde10a, Isl1 and Akap5 are important for brain development and neuronal functions. Microarray analysis showed that expression of all these genes were significantly elevated in APP/PS1 mouse brains after Compound C treatments (Table 3). Consistent with this observation, QRT-PCR analysis demonstrated that their expressions were indeed significantly elevated in the brains of Compound C-treated APP/PS1 mice (FIG. 17C).

Taken together, our QRT-PCR results for all tested genes were consistent with microarray data, indicating that Compound C can indeed regulate the expression of a number of genes involved in AD pathogenesis. Also, Compound C may have other beneficial effects in AD by improving the expression of key genes for coordination, language speaking, behavior as well as normal brain development.

Compound C Functions as a Novel Foxo3 and Foxo4 Modulator In Vivo to Inhibit their Phosphorylation in the Brains of APP/PS1 Mice The increase in expression of Neprilysin (MME) and all of the above listed genes, key for neural function, in Compound C-treated APP/PS1 mice (FIG. 15F-G and FIGS. 17A-17C) led us to hypothesize that Compound C may regulate a transcription factor to control expression of the genes either directly or indirectly. In human IMR32 cells, we found that Compound C can inhibit FOXO4 phosphorylation (FIGS. 9A-9C), strongly suggesting an increase of nuclear FOXO to control the expression of many genes key for AD pathogenesis, learning, memory and/or behavior. Promoter analysis of Neprilysin and all the above validated genes (FIGS. 17A-17C) by Compound C in APP/PS1 mouse brains revealed the presence of one or more consensus Foxo binding motif(s) in their promoter except Penk (sabiosciences.com/chipqpersearch.php?app=TFBS). It is possible that Compound C can also regulate Foxo protein phosphorylation in vivo to control the expression of some of the above genes in mice.

To test this hypothesis, the expression of the Foxo 1, 3 and 4 genes in the microarray studies described earlier was examined, and no significant change in their mRNA levels in the brains of Compound C-treated APP/PS1 mice was observed (data not shown), indicating that compound C has no effect on controlling the overall mRNA levels from these genes.

To investigate if Compound C can control the phosphorylation of Foxo protein in APP/PS1 mice, Western blot analysis was performed on the brain protein samples collected from the mice fed with control or Compound C diets, using specific antibodies for phosphorylated Foxo. As shown in FIG. 18A, less abundant phosphorylated Foxo3 at threonine 32 (pFoxo3) and phosphorylated Foxo4 at threonine 28 (pFoxo4) proteins were detected in the brains of APP/PS1 mice after Compound C treatment, while no clear phosphorylated Foxo1 at threonine 24 was detected by Western blot analysis (data not shown).

Quantitative analysis showed that there was a significant decrease in pFoxo3 in the brains of APP/PS1 mice after Compound C treatments (FIG. 18B). Similarly, pFoxo4 levels in Compound C-treated APP/PS1 mice were also significantly decreased when compared to control mice (FIG. 18C), which is in agreement with the observation in human neuronal IMR32 cells. Since Neprilysin and all of the above validated genes (listed in FIGS. 17A-17C, and key for neuronal development, behavior and other neural functions) contain one or more FOXO binding motif(s) in their promoter, Compound C likely will inhibit FOXO3/4 phosphorylation, resulting in increased nuclear FOXO3/4 to inhibit or stimulate expression of these genes. Regardless, the results suggest that Compound C is a novel FOXO4 modulator not only in human neuroblast cells but also in-vivo in the brain of these AD model mice.

Example 8

Compound C Effects on the Expression of the Notch Signaling Molecules in Human IMR32 Cells and APP/PS1 Mouse Brains Notch signaling is critical for neural development, cognitive function, learning and memory in the brains. Clinical trials of several gamma-secretase inhibitors and modulators for the treatment of Alzheimer's Disease failed due to their inhibition of notch signaling, resulting in toxic effect on cognition in the AD patients (Bruno P. Imbimbo, and Giuseppe A. M. Giardina. Current Topics in Medicinal Chemistry, 2011, 11, 1555-1570). Our in vitro studies in human IMR-32 cells showed that one action of Compound C is to attenuate the expression of gamma-secretase complex genes, PSEN1 and NICASTRIN. Therefore, the expression of the key Notch signaling molecules was explored in vitro and in vivo to determine if Compound C has any inhibitory toxic effect on the Notch signaling.

Compound C Effects on the Expression of Notch Signaling Molecules in IMR32 Cells QRT-PCR analysis of several Notch signaling molecules was performed in IMR-32 cells to test if Compound C is toxic to the Notch signaling in vitro. In brief, IMR-32 cells were treated with a water control and 150 ppb Compound C in 10% FBS containing MEM media for 6 hours, 24 hours, and 48 hours. Cells were subjected to QRT-PCR analysis of Notch signaling and related molecules listed in Table 4 (below). These molecules were selected based on the IPA GO search.

As shown in Table 4, treatment of Compound C for all tested time points did not significantly inhibit the expression of all tested genes except a trend of increased expression of RBPJ, a key downstream transcription factor for the Notch signaling, at 6 hour of treatment. These results indicate that Compound C is not toxic on the expression of Notch signaling, and does not likely have toxic effects on cognitive function.

TABLE 4

Effects of Compound #C on the expression of the key NOTCH signaling molecules in IMR-32 cells as determined by quantitative RT-PCR analysis (mean ± sem).

| Gene | 6 hours treatment | | 24 hours treatment | | 48 hours treatment | |
|---|---|---|---|---|---|---|
| | Control | #C | Control | #C | control | #C |
| NOTCH 1 | 100 ± 17 (3) | 94 ± 7 (4) | 100 ± 10 (4) | 89 ± 10 (3) | 100 ± 4 (6) | 90 ± 9 (3) |
| NOTCH 2 | 100 ± 14 (4) | 95 ± 16 (4) | 100 ± 10 (5) | 103 ± 27 (3) | 100 ± 12 (6) | 94 ± 40 (3) |
| NOTCH 3 | 100 ± 16 (3) | 95 ± 7 (4) | 100 ± 11 (5) | 105 ± 14 (3) | 100 ± 7 (6) | 81 ± 23 (4) |
| NOTCH 4 | Undetected | | Undetected | | Not determined | |
| RBPJ | 100 ± 15 (4) | 144 ± 12 (4)* | 100 ± 11 (5) | 119 ± 37 (3) | 100 ± 7 (6) | 97 ± 7 (4) |
| HER2 | 100 ± 9 (3) | 96 ± 4 (4) | 100 ± 8 (5) | 100 ± 11 (3) | 100 ± 13 (6) | 106 ± 23 (3) |
| HES1 | 100 ± 21 (4) | 101 ± 6 (4) | 100 ± 10 (5) | 102 ± 18 (3) | 100 ± 5 (6) | 115 ± 9 (4) |
| HEY1 | 100 ± 11 (4) | 120 ± 9 (4) | 100 ± 7 (5) | 121 ± 10 (3) | 100 ± 9 (6) | 115 ± 11 (3) |
| NFKB1 | 100 ± 12 (3) | 112 ± 7 (4) | 100 ± 15 (5) | 106 ± 11 (3) | 100 ± 6 (6) | 109 ± 12 (4) |
| NFKB2 | 100 ± 15 (4) | 103 ± 7 (4) | 100 ± 15 (5) | 85 ± 28 (3) | 100 ± 9 (6) | 97 ± 14 (4) |

Notes:
The relative mRNA expression of NOTCH1/NOTCH2/NOTCH3 in IMR-32 cells is 100/1/1000.
*P = 0.059 when compared to the control group that were treated with water control at 6 hours.

Effects of Compound C on the Expression Profiles of 65 Notch Signaling Molecules in APP/PS1 Mice To further investigate potential toxic effects of compound on the Notch signaling, microarray analysis was performed. Expression of Notch signaling molecules in the brains of Compound C-treated APP/PS1 mice was analyzed. In brief, APP/PS1 mice at the age of 6 months were fed with control diet (n=5) and Compound C diet (n=6) for 6 months. Brain tissues were collected and subjected to microarray analysis. The transcription profiles of 65 Notch receptor signaling (based GO search) related genes were pulled out from the original microarray datasets, and then subjected to unsupervised hierarchical clustering analysis based on arrays (animals) using GeneSpring 13.0 software (Agilent Technologies, Inc.), to generate the heatmap of these gene expression (see FIG. 19).

In the heatmap, gene expression levels (normalized by Actb) were shown in color intensity that reflect the expression changes compared to mean value of each gene, where blue, red or yellow colors represent decreased, increased or no change in the level of expression intensity, respectively. The dendogram on the top reflects the extent of similarity of expression profiles between animals.

As shown in FIG. 19, related transcription profiles of these genes failed to be separated by dietary treatments. In other words, the expression profile of these Notch signaling molecules of 5 control and 6 Compound C-treated mice failed to be clustered into a control and a Compound C treatment group, respectively. Expression levels of Notch 1-4, RBPJ, and other molecules such as Hey1, Hes1 and Hey2 (listed in the right side of the heatmap) did not have obvious change across all tested 5 control and 6 Compound C treated animals. In addition, there was no significant decrease of the Notch signaling in APP/PS1 mice after Compound C treatment by IPA analysis (data not shown). These results indicate that Compound C does not have a toxic effect in inhibiting the expression of Notch signaling molecules in APP/PS1 mice.

Based on the above studies in human IMR-32 cells and APP/PS1 mice, it can be concluded that Compound C does not have inhibitory effects on Notch signaling.

Example 9

Effects of Selenium Compound Preparations, as Opposed to Extracts of Selenium Enriched Yeast, on Neuronal Cell Survival Extracts of selenium-enriched yeast, produced by water or chemical solvent extraction, contain, in addition to mixtures of small selenium compounds, many sulfur-bearing compounds and other unidentified components which may be toxic to cells or act in an opposing biological manner to the synthetic selenium compounds. Among the principal components present in these extracts are the sulfur analogs of the selenium compounds described in this application.

Materials and Methods
Cell Viability Analysis

For primary neurons, dissociated primary cortical neuron cultures were established from E-18 rat embryos as previously described (Lovell et al., Free Radic. Biol. Med. 2000; Lovell et al., Neurobiol. Aging 2001). Studies were carried out on cells 7 days in culture by switching to Locke's solution consisting of 1 mL of 154 mM NaCl, 5.6 mM KCl, 2.3 mM $CaCl_2$, 1.0 mM $MgCl_2$, 3.6 mM $NaHCO_3$, 10 mM glucose, 5 mM HEPES (pH 7.2) with 10 mg/L gentamicin sulfate. Primary neurons were treated for 24 hours in Locke's solution with the indicated selenium and sulfur compounds in Table 5. Cell counts were performed to measure cell survival/toxicity.

Statistical Analysis

If applicable, a Student's t-test was performed to determine the statistical difference between two groups. A P value less than 0.05 was considered significant.

Results and Discussion

The effects of the selenium and sulfur compounds, identified as components of water extracts of selenium-enriched yeast, on neuronal cell survival was also tested. Primary neurons isolated from fetal rat brain were incubated with chemically synthesized individual selenium and sulfur compounds that were identified as components of water extracts of selenium-enriched yeast (Table 5). In this case, the elemental concentration of each compound identified in Table 5 was 150 ppb and, where mixtures were used, the 150 ppb treatment was made up of 30 ppb of the element from each of the five compounds in question.

TABLE 5

The list of selenium compounds and their sulfur analogs

| | Selenium Compounds | | Sulfur Analogs |
|---|---|---|---|
| A | L-Methylselenocysteine | F | L-Methylcysteine |
| B | L-Selenomethionine | G | L-methionine |
| C | Methylselenoadenosine | H | Methylthioadenosine |
| D | Selenoadenosyl homocysteine | I | Adenosyl homocysteine |
| E | gamma-glutamyl-methylseleno-cysteine | J | gamma-glutamyl-methyl-cysteine |
| K | Mixture of above A-E | L | Mixture of above F-J |

Based on cell counts (Table 6) it was determined that treatment with 150 ppb selenium from any of the tested compounds and their mixture effectively maintained neuron survival (no significant difference compared to control). However, survival rates were significantly lower for neurons treated with the sulfur Compound I and Compound J and lowest of all for neurons treated with the sulfur compound mixture, L.

TABLE 6

Effects of selenium and sulfur compounds on the cell survival of primary fetal rat neurons after treated with 150 ppb selenium or sulfur compound(s) for 24 hours

| Selenium compound | Viable Cell Number (Mean ± SEM, n = 6) | Sulfur compound | Viable Cell Number (Mean + SEM, n = 6) |
|---|---|---|---|
| Control | 100 ± 1.57 | | |
| A | 94.45 ± 1.72 | F | 96.48 ± 3.89 |
| B | 90.59 ± 6.82 | G | 103.84 ± 4.98 |
| C | 101.1 ± 4.22 | H | 100.24 ± 9.45 |
| D | 96.08 ± 3.89 * | I | 82.08 ± 3.407 ** |
| E | 95.69 ± 10.53 * | J | 83.76 ± 2.775 ** |
| K (a mixture of A-E) | 103.99 ± 7.4 * | L (a mixture of F-J) | 74.83 ± 6.14 ** |

\* $P < 0.05$ selenium compared to sulfur analog
\*\* $P < 0.05$ compared to Control (water vehicle) group All publications and patents mentioned in the present application are herein incorporated by reference. Various modification and variation of the described methods and compositions of the present application will be apparent to those skilled in the art without departing from the scope and spirit of the present application. Although the present application has been described in connection with specific preferred embodiments, it should be understood that the present application as claimed should not be unduly limited to such specific embodiments. Indeed, various modifications of the described modes for carrying out the present application that are obvious to those skilled in the relevant fields are intended to be within the scope of the following claims.

The invention claimed is:

1. A method for inhibiting β amyloid aggregation in a subject in need thereof comprising:
administering a composition to a subject, the composition comprising at least 0.1% (w/v) of 5'-deoxy-5'-methylselenoadenosine, or a pharmaceutically acceptable salt thereof; and a carrier.

2. A method for inhibiting ApoE4 expression in a subject in need thereof comprising:
administering a composition to a subject, the composition comprising at least 0.1% (w/v) of 5'-deoxy-5'-methylselenoadenosine, or a pharmaceutically acceptable salt thereof; and a carrier.

3. A method of decreasing p38 phosphorylation in a subject in need thereof comprising:
administering a composition to a subject, the composition comprising at least 0.1% (w/v) of 5'-deoxy-5'-methylselenoadenosine, or a pharmaceutically acceptable salt thereof; and a carrier.

4. A method of increasing neprilysin expression in a subject in need thereof comprising:
administering a composition to a subject, the composition comprising at least 0.1% (w/v) of 5'-deoxy-5'-methylselenoadenosine, or a pharmaceutically acceptable salt thereof; and a carrier.

5. A method of decreasing beta-secretase (BACE) expression in a subject in need thereof comprising:
administering a composition to a subject, the composition comprising at least 0.1% (w/v) of 5'-deoxy-5'-methylselenoadenosine, or a pharmaceutically acceptable salt thereof; and a carrier.

6. A method of increasing insulin-degrading enzyme (IDE) expression in a subject in need thereof comprising:
administering a composition to a subject, the composition comprising at least 0.1% (w/v) of 5'-deoxy-5'-methylselenoadenosine, or a pharmaceutically acceptable salt thereof; and a carrier.

7. A method for inhibiting β amyloid aggregation in a subject in need thereof comprising:
administering a composition to a subject, the composition comprising at least 0.033% (w/v) of 5'-deoxy-5'-methylselenoadenosine, or a pharmaceutically acceptable salt thereof; and a carrier.

8. A method of decreasing phosphorylated tau (pTau) expression in a subject in need thereof comprising:
administering a composition to a subject, the composition comprising at least 0.1% (w/v) of 5'-deoxy-5'-methylselenoadenosine, or a pharmaceutically acceptable salt thereof; and a carrier.

* * * * *